US009457045B2

(12) United States Patent
Gleave et al.

(10) Patent No.: US 9,457,045 B2
(45) Date of Patent: Oct. 4, 2016

(54) COMBINATION OF ANTI-CLUSTERIN OLIGONUCLEOTIDE WITH HSP90 INHIBITOR FOR THE TREATMENT OF PROSTATE CANCER

(75) Inventors: Martin E. Gleave, Vancouver (CA); Amina Zoubeidi, West Vancouver (CA); François Lamoureux, Breze (FR)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 14/005,186

(22) PCT Filed: Mar. 12, 2012

(86) PCT No.: PCT/IB2012/000696
§ 371 (c)(1),
(2), (4) Date: Nov. 22, 2013

(87) PCT Pub. No.: WO2012/123823
PCT Pub. Date: Sep. 20, 2012

(65) Prior Publication Data
US 2014/0080895 A1 Mar. 20, 2014

Related U.S. Application Data

(60) Provisional application No. 61/453,102, filed on Mar. 15, 2011.

(51) Int. Cl.
| C12N 15/11 | (2006.01) |
| A61K 31/713 | (2006.01) |
| A61K 31/4162 | (2006.01) |
| A61K 31/7088 | (2006.01) |
| A61K 45/06 | (2006.01) |
| A61K 31/416 | (2006.01) |
| C07H 21/04 | (2006.01) |

(52) U.S. Cl.
CPC ........... *A61K 31/713* (2013.01); *A61K 31/416* (2013.01); *A61K 31/4162* (2013.01); *A61K 31/7088* (2013.01); *A61K 45/06* (2013.01)

(58) Field of Classification Search
None
See application file for complete search history.

(56) References Cited

U.S. PATENT DOCUMENTS

| 6,383,808 B1 | 5/2002 | Monia et al. |
| 6,900,187 B2 | 5/2005 | Gleave et al. |
| 7,285,541 B2 | 10/2007 | Gleave et al. |
| 7,368,436 B2 | 5/2008 | Gleave et al. |
| 7,534,773 B1 | 5/2009 | Gleave et al. |
| 7,569,551 B2 | 8/2009 | Gleave et al. |
| 7,592,323 B1 | 9/2009 | Gleave et al. |
| 7,732,422 B2 | 6/2010 | Gleave et al. |
| 7,928,135 B2 | 4/2011 | Huang et al. |
| 8,173,615 B2 | 5/2012 | Gleave et al. |
| 8,361,981 B2 | 1/2013 | Gleave et al. |
| 8,536,149 B2 | 9/2013 | Gleave et al. |
| 8,710,020 B2 | 4/2014 | Gleave et al. |
| 2002/0128220 A1 | 9/2002 | Gleave |
| 2003/0166591 A1* | 9/2003 | Gleave ............... A61K 31/00 514/44 R |
| 2008/0014198 A1 | 1/2008 | Gleave et al. |
| 2008/0119425 A1 | 5/2008 | Gleave et al. |
| 2009/0258089 A1 | 10/2009 | Gleave et al. |
| 2011/0021603 A1 | 1/2011 | Gleave et al. |
| 2011/0142827 A1 | 6/2011 | Gleave et al. |
| 2012/0322850 A1 | 12/2012 | Gleave et al. |
| 2013/0017272 A1 | 1/2013 | Duksin et al. |
| 2013/0143944 A1 | 6/2013 | Gleave et al. |
| 2013/0310440 A1 | 11/2013 | Duksin et al. |
| 2014/0088178 A1 | 3/2014 | Gleave et al. |
| 2014/0100261 A1 | 4/2014 | Gleave et al. |

FOREIGN PATENT DOCUMENTS

| WO | WO 00/49937 | 8/2000 |
| WO | WO 03/072591 | 9/2003 |
| WO | WO 2004/018675 | 3/2004 |
| WO | WO 2005/094899 A1 | 10/2005 |
| WO | WO 2006/056054 | 6/2006 |

(Continued)

OTHER PUBLICATIONS

Lamoureux et al., The novel HSP90 inhibitor, PF-04929113, inhibits AR activity and osteoclastogenesis and delays castrate-resistant LNCaP prostate cancer tumor growth, Abstract #4512, Apr. 2010, Proceedings of the American Association for Cancer Research Annual Meeting, vol. 51, pp. 1094-1095.*

(Continued)

*Primary Examiner* — Dana Shin
(74) *Attorney, Agent, or Firm* — Larson & Anderson, LLC

(57) ABSTRACT

The present invention provides a method for treating a mammalian subject affected by prostate cancer comprising i) an oligonucleotide which reduces clusterin expression and ii) a Heat Shock Protein 90 (Hsp90) inhibitor each in an amount that when in combination with the other is effective to treat the mammalian subject. The present invention also provides pharmaceutical compositions comprising an amount of an oligonucleotide which reduces clusterin expression, and a Hsp90 inhibitor for use in treating a mammalian subject affected by prostate cancer. Also provided are oligonucleotides which reduce clusterin expression for use in combination with a Hsp90 inhibitor in treating a mammalian subject affected by prostate cancer, and a composition for treating a mammalian subject affected by prostate cancer comprising i) an oligonucleotide which reduces clusterin expression and ii) a Hsp90 inhibitor each in an amount that when in combination with the other is effective to treat the mammalian subject.

15 Claims, 25 Drawing Sheets

(56) References Cited

FOREIGN PATENT DOCUMENTS

| WO | 2006/124904 A2 | 11/2006 |
|---|---|---|
| WO | 2011060328 A1 | 5/2011 |
| WO | WO 2012/123820 | 9/2012 |
| WO | WO 2012/123823 | 9/2012 |
| WO | WO 2012/156817 | 11/2012 |
| WO | WO 2013/173757 | 11/2013 |

OTHER PUBLICATIONS

Zoubeidi et al., Cooperative interactions between androgen receptor (AR) and heat-shock protein 27 facilitate AR transcriptional activity, 2007, Cancer Research, vol. 67, pp. 10455-10465.*

Bellmunt et al., "Novel approaches with targeted therapies in bladder cancer," Critical Reviews in Oncology/Hematology 46:S85-S104 (2003).

Huang et al., "Discovery of Novel 2-Aminobenzamide Inhibitors of Heat Shock Protein 90 as Potent, Selective and Orally Active Antitumor Agents," Journal of Medicinal Chemistry 52:4288-4305 (2009).

Zoubeidi et al., "Targeting the Cytoprotective Chaperone Clusterin as a Strategy to Increase the Anticancer Activity of the HSP90 inhibitor 17-allylamino-demethoxy geldanamycin," Journa of Urology 179(4) : Supplement 225 (2008).

Lamoureux et al. (2011). A Novel HSP90 Inhibitor Delays Castrate-Resistant Prostate Cancer without Altering Serum PSA Levels and Inhibits Osteoclastogenesis. Clinical Cancer Research, 17(8), 2301-2313.

Zoubeidi et al. (2010). Targeting the Cytoprotective Chaperone, Clusterin, for Treatment of Advanced Cancer. Clinical Cancer Research, 16(4), 1088-1093.

Lamoureux et al. (2011). CLU inhibition using OGX-011 as an adjuvant therapeutic strategy for HSP90 inhibition in prostate cancer. In 'Genitourinary Cancer' Abstracts of the 2011 ASCO Annual Meeting, Vancouver, BC, Canada. Journal of Clinical Oncology, 29(Suppl. 15), Abstract 4573.

Notification of Transmittal of the International Search Report and the Written Opinion of the International Searching Authority, or the Declaration, including an International Search Report and Written Opinion of the International Searching Authority, mailed Jul. 18, 2012 in connection with PCT International Application No. PCT/IB2012/000696, filed Mar. 12, 2012.

Notification Concerning Transmittal of International Preliminary Report on Patentability (Chapter I of the Patent Cooperation Treaty), including an International Preliminary Report on Patentability and Written Opinion of the International Searching Authority, mailed Sep. 26, 2013 by The International Bureau of WIPO in connection with PCT International Application No. PCT/IB2012/000696, filed Mar. 12, 2012.

Tran et al., Development of a Second-Generation Antiandrogen for Treatment of Advanced Prostate Cancer, Science, 2009, pp. 787-790, vol. 324(5928).

Wong et al., Molecular characterization of human TRPM-2/clusterin, a gene associated with sperm maturation, apoptosis and neurodegeneration, Eur. J. Biochem, 1994, pp. 917-925, vol. 221(3).

Young, J. C., et al., Polypeptide release by Hsp90 involves ATP hydrolysis and is enhanced by the co-chaperone p23, EMBO J, 2000, pp. 5930-5940, vol. 19.

Scher, H. I. et al., Antitumour activity of MDV3100 in castration-resistant prostate cancer: a phase 1-2 study, Lancet, 2010, pp. 1437-1446, vol. 375, No. 9724.

Culig, Z., Androgen Receptor Cross-talk with Cell Signalling Pathways, Growth Factors, 2004, pp. 179-184, vol. 22.

Gleave, M. et al., Knock-down of the Cytoprotective Gene, Clusterin, to Enhance Hormone and Chemosensitivity in Prostate and Other Cancers, Ann N Y Acad Sci, 2005, pp. 1-15, vol. 1058.

Gleave, M. et al., Antisense Therapy for Cancer, Nat Rev Cancer, 2005, pp. 468-479, vol. 5.

Miyake, H., et al., Synergistic Chemsensitization and Inhibition of Tumor Growth and Metastasis by the Antisense Oligodeoxynucleotide Targeting Clusterin Gene in a Human Bladder Cancer Model1, Clinical Cancer Research, 2001, pp. 4245-4252, vol. 7.

Whitesell, L. et al., HSP90 and The Chaperoning of Cancer, Nature Reviews Cancer, 2005, pp. 761-772, vol. 5.

Zellweger, T. et al., Overexpression of the cytoprotective protein clusterin decreases radiosensitivity in the human LNCaP prostate tumour model, BJU Int., 2003, pp. 463-469, vol. 92.

Chou, TC et al., Quantitative analysis of dose-effect relationships: the combined effects of multiple drugs or enzyme inhibitors, Adv Enzyme Regul., 1984, pp. 27-55, vol. 22.

Georget, V. et al., Mechanism of Antiandrogen Action: Key Role of Hsp90 in Conformational Change and Transcriptional Activity of the Androgen Receptor, Biochemistry, 2002, pp. 11824-11831, vol. 41.

Glaze, E. R. et al., Preclinical toxicity of a geldanamycin analog, 17-(dimethylaminoethylamino)-17-demethoxygeldanamycin (17-DMAG) in rats and dogs: potential clinical relevance, Cancer Chemother Pharmacol, 2005, pp. 637-647.

Kamal, A., et al., A high-affinity conformation of Hsp90 confers tumour selectivity on Hsp90 inhibitors, Nature, 2003, pp. 407-410, vol. 425.

Kim, J. et al., Prostate specific antigen gene regulation by androgen receptor, J Cell Biochem, 2004, pp. 233-241, vol. 93.

Leung, S.Y., et al., Polymeric micellar paclitaxel phosphorylates Bcl-2 and induces apoptotic regression of androgen-independent LNCaP prostate tumors, Prostate, 2000, pp. 156-163, vol. 44.

Miyake, H. et al., Acquisition of resistance to Fas-mediated apoptosis by overexpression of clusterin in human renal-cell carcinoma cells, Mol Urol, 2001, pp. 105-111, vol. 5, Abstract only.

Yagoda, et al., Cytotoxic chemotherapy for advance hormone-resistant prostate cancer, Cancer, 1993, 71 (Supp. 3): 1098119.

Bagatell, R. et al., Induction of a heat shock factor 1-dependent stress response alters the cytotoxic activity of hsp90-binding agents, Clin Cancer Res., 2000, pp. 3312-3318, vol. 6.

Banerji, U. et al., Biomarkers in early clinical trials: the committed and the skeptics, Clin Cancer Res, 2008, p. 2512, No. 14.

Carthew, R.W., Gene silencing by double-stranded RNA, Current Opinion in Cell Biology, 2001, pp. 244-248, vol. 13.

Cervantes-Gomez F. et al., Transcription inhibition of heat shock proteins: a strategy for combinatin of 17-allylamino-17demethoxygeldanamycin and actinomysin d, Cancer Res., 2009, pp. 3947-3954, vol. 69.

Chandarlapaty, S. et al., SNX2112, a synthetic heat shock protein 90 inhibitor, has potent antitumor activity against HER kinasedependent cancers, Clin Cancer Res., 2008, pp. 240-248, vol. 14.

Chi, KN, et al., A phase I study of OGX-011, a 2'-methoxyethyl phosphorothioate antisense to clusterin, in combination with docetaxel in patients with advanced cancer, Clin Cancer Res., 2008, pp. 833-839, vol. 14.

Chi, KN, et al., Randomized phase II study of docetaxel and prednisone with or without OGX-011 in patients with metastatic castration resistant prostate cancer, J. Clin. Oncol., 2010, pp. 4247-4254, vol. 28.

Chi et al., A phase I pharmacokinetic (PK) and pharmacodynamic (PD) study of custirsen, a 2'-Methoxyethyl antisense Oligonucleotide to Clusterin, in Patients with Localized Prostate Cancer, Journal of the National Cancer Institute, 2005, pp. 1287-1296, vol. 97(17).

Chi et al., A phase I pharmacokinetic (PK) and pharmacodynamic (PD) study of custirsen, a 2'methoxyethyl phosphorothioate antisense to clusterin, in patients with prostate cancer prior to radical prostatectomy, Journal of Clinical Oncology, 2004, ASCO Annual Meeting Proceedings, p. 3033 vol. 22, No. 14S.

Chiosis, G. et al., 17AAG: low target binding affinity and potent cell activity—finding an explanation, Mol. Cancer Ther., 2003, pp. 123-129, vol. 2.

Dai, C. et al., Heat shock factor 1 is a powerful multifaceted modifier of carcinogenesis, Cell, 2007, pp. 1005-1018, vol. 130.

Eccles, S.A., et al., NVP-AUY922: a novel heat shock protein 90 inhibitor active against xenograft tumor growth, angiogenesis, and metastasis, Cancer Res, 2008, pp. 2850-2860, vol. 68.

(56) References Cited

OTHER PUBLICATIONS

Egorin et al., Metabolism of 17-(Allyamino)-17-dementhoxygeldanamycin(NSC 330507) by Murine and Human Hepatic Preparations, Cancer Research, 1998, pp. 2385-2396, vol. 58.

Elbashir et al., Duplexes of 21-nucleotide RNAs mediate RNA interference in cultured mammalian cells, Nature, 2001, pp. 494-498, vol. 411.

Fire et al., Potnt and specific genetic interference by double-stranded RNA in Caenorhabditis elegans, Nature, 1998, pp. 806-811, vol. 391.

Gleave, M. E. et al., Prostate cancer: 9. Treatment of advance disease, CMAJ, 1999, pp. 225-232, vol. 160.

Gleave M, et al., Progression to androgen independence is delayed by adjuvant treatment with antisense Bcl-2 oligodeoxynucleotides after castration in the LNCaP prostate tumor model, Clin. Cancer Res., 1999, pp. 2891-2898, vol. 5.

Guo, F. et al., Abrogation of heat shck protein 70 induction as a strategy to increase antileukemia activity of heat shock protein 90 inhibitor 17-allylamino-demethoxy geldanamycin, Cancer Res., 2005, pp. 10536-10544, vol. 65.

Humphreys, D. T. et al., Clusterin has chaperone-like activity similar to that of small heat shock proteins, J. Biol. Chem., 1999, pp. 6875-6881, vol. 274.

Jemal, A., et al., Cancer statistics, CA Cancer J. Clin., 2006, pp. 106-130, vol. 56.

July, L. V. et al., Nucleotide-based therapies targeting clusterin chemosensitize human lung adenocarcinoma cells both n vitro and in vivo., Mol. Cancer Ther., 2004, pp. 223-232, vol. 3.

July, L. V. et al, Clusterin expression is significantly enhanced in prostate cancer cells following androgen withdrawal therapy, Prostate, 2002, pp. 179-188, vol. 50.

Knudsen, K. E. et al., Starving the addiction: new opportunities for durable suppression of AR signaling in prostate cancer, Clin. Cancer Res., 2009, pp. 4792-4798, vol. 15.

Koga et al., Inhibition of Cancer Invasion and Metastasis by Targeting the Molecular Chaperone Heat-shock Protein 90, Anticancer Research, 2009, pp. 797-808, vol. 29.

Krajewska et al., Immunohistochemical analysis of bcl-2, bax, bcl-x, and mcl-1 expression in prostate cancers, Am. J. Pathol, 1996, pp. 1567-1576, vol. 148.

Kyprianou, N. et al., Programmed cell death during regression of PC-82 human prostate cancer following androgen ablation, Cancer Res., 1990, pp. 3748-3753, vol. 50.

Kyprianou, N. et al., Programmed cell death during regression of the MCF-7 human breast cancer following estrogen ablation, Cancer Res., 1991, pp. 162-166, vol. 51.

Lassi et al., Update on castrate-resistant prostate cancer: 2010, Current Opinion in Oncology, 2010, pp. 263-267, vol. 22.

Magklara, A. et al., Characterization of androgen receptor and nuclear receptor co-regulator expression in human breast cancer cell lines exhibiting differential regulation of kallikreins 2 and 3, Int. J. Cancer, 2002, pp. 507-514, vol. 100.

McDonnell et al., Expression of the proto-oncogene bcl-2 in the prostate and its association with the emergence of androgen-independent prostate cancer, Cancer Res., 1992, pp. 6940-6944, vol. 52.

Miyake, H. et al., Antisense oligodeoxynucleotide therapy targeting clusterin gene for prostate cancer: Vancouver experience from discovery to clinic, International Journal of Urology, 2005, pp. 785-794, vol. 12.

Miyake, H. et al., Overexpression of insulin-like growth factor binding protein-5 helps accelerate progression to androgen-independence in the human prostate LNCaP tumor model through activation of phosphatidylinositol 3'-kinase pathway, Endocrinology, 2000, pp. 2257-2265, vol. 141.

Miyake, H. et al., Testosterone-repressed prostate message-2 is an antiapoptotic gene involved in progression to androgen independence in prostate cancer, Cancer Res., 2000, pp. 170-176, vol. 60.

Miyake, H. et al., Antisense Bcl-2 oligodeoxynucleotides inhibit progression to androgen-independence after castration in the Shionogi tumor model, Cancer Res., 1999, pp. 4030-4034, vol. 59.

Miyake, H. et al., Acquisition of chemoresistant phenotype by overexpression of the antiapoptotic gene testosterone-repressed prostate message-2 in prostate cancer xenograft models, Cancer Res., 2000, pp. 2547-2554, vol. 60.

Miyake, H. et al., Antisense TRPM-2 oligodeoxynucleotides chemosensitize human androgen-independent PC-3 prostate cancer cells both in vitro and in vivo., 2000, Clin. Cancer Res., pp. 1655-1663, vol. 6.

Oh et al., Management of hormone refractory prostate cancer: current standards ad future prospects, J. Urol., 1998, pp. 1220-1229, vol. 160(4).

Okawa, Y. et al., SNX-2112, a selective hsp90 inhibitor, potently inhibits tumor cell growth, angiogenesis, and osteoclastogenesis in multiple myeloma and othe hematologic tumors by abrogating signaling via Akt and ERK, Blood, 2009, pp. 846-855, vol. 113.

Raffo et al., Overexpression of bcl-2 protects prostate cancer cells from apoptosis in vitro and confers resistance to androgen depletion in vivo, Cancer Res., 1995, pp. 4438-4445, vol. 55(19).

Rocchi, P. et al., Heat shock protein 27 increases after androgen ablation and plays a cytoprotective role in hormone-refractory prostate cancer, Cancer Res., 2004, pp. 6595-6602, vol. 64.

Rosenberg, M. E. et al., Clusterin: physiologic and pathophysiologic considerations, Int. J. Biochem Cell Biol., 1995, pp. 633-645, vol. 27.

Rossi, A. et al., Targeting the heat shock factor 1 by RNA interference: a potent tool to enhance hyperthermochemotherapy efficacy in cervical cancer: a phse 1-2 study, Cancer Research, 2006, pp. 7678-7685, vol. 66.

Sensibar et al., Prevention of Cell Death Induced by Tumor Necrosis Factor α in LNCaP Cells by Overexpression of Sulfated Glycoprotein-2 (Clusterin), Cancer Research, 1995, pp. 2431-2437, vol. 55.

Solit, D. B. et al., Inhibition of heat shock protein 90 function down-regulates Akt kinase and sensitizes tumors to Taxol, Cancer Res., 2003, pp. 2139-2144, vol. 63.

Solit, D. B. et al., 17-Allylamino-17-demethoxygeldanamycin induces the degradation of androgen receptor and HER-2/neu and inhibits the growth of prostate cancer xenografts, Clin Cancer Res, 2002, pp. 986-993, vol. 8.

Song, H. et al., Loss of Nkx3.1 leads to the activation of discrete downstream target genes during prostate tumorigenesis, Oncogene, 2009, pp. 3307-3319, vol. 28.

Sowery, R. D. et al., Clusterin knockdown using the antisense oligonucleotide OGX-011 re-sensitizes docetaxelrefractory prostate cancer PC-3 cells to chemotherapy, BJU Int., 2008, pp. 389-397, vol. 102.

Steinberg, J. et al., Intracellular levels of SGP-2 (Clusterin) correlate with tumor grade in prostate cancer, Clin Cancer Res., 1997, pp. 1707-1711, vol. 3.

Sydor, J. R. et al., Development of 17-allylamino-17-demethoxygeldanamycin hydroquinone hydrochloride (IPI-504), an anticancer agent directed against Hsp90, Pro. Natl Acad Sci, USA, 2006, pp. 17408-17413, vol. 103.

Takayama, S. et al., Heat-shock proteins as regulators of apoptosis, Oncogene, 2003, pp. 9041-9047, vol. 22.

English translation of Japanese Office Action dated Dec. 22, 2015 from corresponding Japanese Patent Application No. 2013-558527.

Rubenstein et al., Treatment of prostate and breast tumors employing mon0- and bi-specific antisense oligonucleotides targeting apoptosis inhibitory proteins clusterin and bcl-2, Med Oncol, 2010, pp. 592-599, vol. 27.

Lamoureux, F. et al., Clusterin Inhibition Using OGX-011 Synergistically Enhances Hsp90 Inhibitor Activity by Suppressing the Heat Shock Response in Castrate-Resistant Prostate Cancer, Cancer Research, 2011, pp. 5838-5849, vol. 71, No. 17, XP055131307.

Lamoureux, F. et al, Downregulation of Hsp27 using OGX-427 induces ER stress and potentiates Hsp90 inhibitors to delay castrate resistant prostate cancer, European Urology Supplements, Feb. 2012, p. e245, vol. 11, No. 1, XP055131325.

(56) References Cited

OTHER PUBLICATIONS

Lamoureux, F. et al, Downregulation of Hsp27 using OGX-427 induces ER stress and -potentiates Hsp90 inhibitors to delay castrate resistant prostate cancer, Feb. 2012, XP002727737, Retrieved from the Internet: URL: http://files.shareholder.com/downloads/SNUS/0x0x545858/1996cc0-5b39-4d6f-a2ab-bdc3fa2cfd1c/Poster%20OGX-427%20Hsp90%20inhibitors.pdf.

Extended European Search Report dated Aug. 14, 2014 from related European Patent Application No. 12757133.9.

* cited by examiner

A

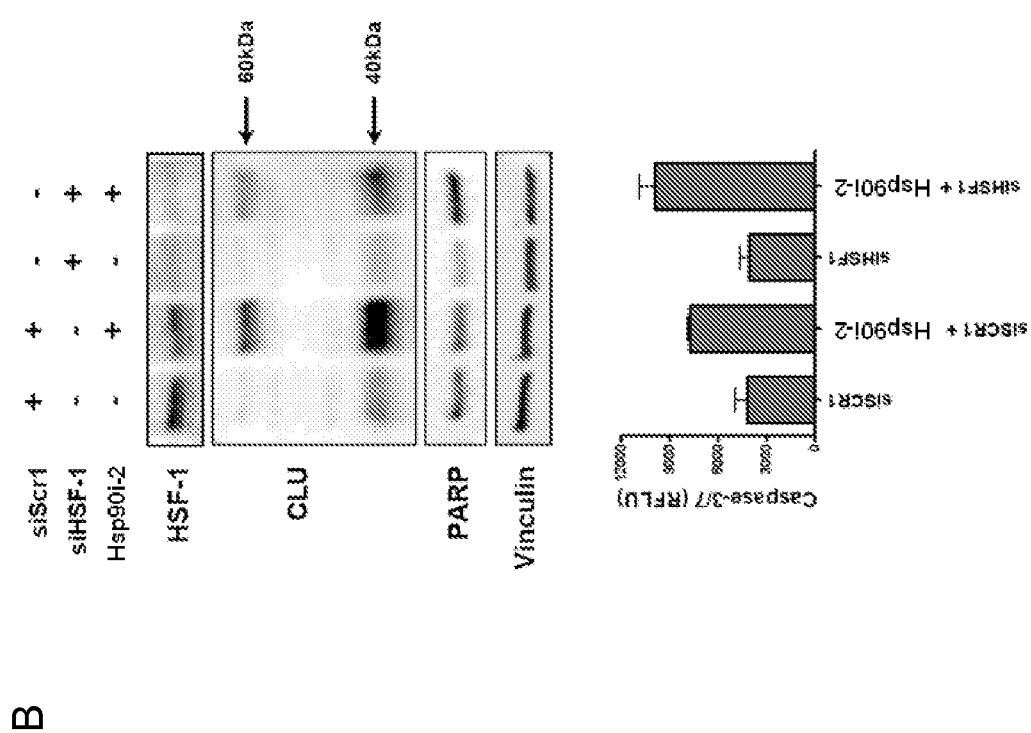

COMBINATION OF ANTI-CLUSTERIN OLIGONUCLEOTIDE WITH HSP90 INHIBITOR FOR THE TREATMENT OF PROSTATE CANCER

This application is a §371 national stage of PCT International Application No. PCT/IB2012/000696, filed Mar. 12, 2012, claiming the benefit of U.S. Provisional Application No. 61/453,102, filed Mar. 15, 2011, the contents of each of which are hereby incorporated by reference in their entirety.

This application incorporates-by-reference nucleotide and/or amino acid sequences which are present in the file named "131122_2609_82689_C_PCT_US_Substitute_Sequence_Listing_BI.txt," which is 13.2 kilobytes in size, and which was created Nov. 20, 2013 in the IBM-PC machine format, having an operating system compatibility with MS-Windows, which is contained in the text file filed Nov. 22, 2013 as part of this application.

Throughout this application, various publications are referenced, including referenced in parenthesis. Full citations for publications referenced in parenthesis may be found listed in alphabetical order at the end of the specification immediately preceding the claims. The disclosures of all referenced publications in their entireties are hereby incorporated by reference into this application in order to more fully describe the state of the art to which this invention pertains.

FIELD OF THE INVENTION

The subject invention relates to combination therapy for treating prostate cancer.

BACKGROUND OF THE INVENTION

Prostate cancer (PCa) is the most common cancer and the third most common cause of cancer related mortality in men in the United States (Jemal et al., 2006). Androgen ablation remains the standard effective therapy for patients with advanced PCa, inhibiting proliferation and inducing apoptosis in tumor cells (Kyprianou et al., 1990). Unfortunately, after short-term remissions, surviving tumor cells recur with castrate resistant prostate cancer (CRPC) and death usually within 3 years in most men (Gleave et al., 1999). CRPC progression results from mechanisms attributed to re-activation of androgen receptor axis (Knudsen et al., 2009), alternative mitogenic growth factor pathways (Miyake et al., 2000; Culig et al., 2004), and stress-induced prosurvival gene (Gleave et al., 1999; Miyake et al., 1999) and cytoprotective chaperone networks (Rocchi et al., 2004; Miyake et al., 2000). To significantly improve survival in men with PCa, new therapeutic strategies to inhibit the appearance of this phenotype must be developed. It has been observed that numerous proteins are expressed in increased amounts by prostate tumor cells following androgen withdrawal. At least some of these proteins are assumed to be associated with the observed apoptotic cell death which is observed upon androgen withdrawal. (Raffo et al., 1995; Krajewska et al., 1996; McDonnell et al., 1992). The functions of many of the proteins, however, is not completely understood. Clusterin (also known as sulfated glycoprotein-2 (SGP-2) or TRPM-2) is within this latter category.

Clusterin

Clusterin is a cytoprotective chaperone protein that promotes cell survival and confers broad-spectrum resistance to cancer treatments (Chi et al. 2005). In Sensibar et al., Cancer Research 55: 2431-2437, 1995, the authors reported on LNCaP cells transfected with a gene encoding clusterin, and watched to see if expression of this protein altered the effects of tumor necrosis factor α (TNFα), to which LNCaP cells are very sensitive. Treatment of the transfected LNCaP cells with TNFα was shown to result in a transient increase in clusterin levels for a period of a few hours, but these levels had dissipated by the time DNA fragmentation preceding cell death was observed.

As described in U.S. Pat. No. 7,534,773, the contents of which are incorporated by reference, enhancement of castration-induced tumor cell death and delay of the progression of androgen-sensitive cancer cells to androgen-independence may be achieved by inhibiting the expression of clusterin by the cells.

Custirsen

Custirsen is a second-generation antisense oligonucleotide that inhibits clusterin expression. Custirsen is designed specifically to bind to a portion of clusterin mRNA, resulting in the inhibition of the production of clusterin protein. The structure of custirsen is available, for example, in U.S. Pat. No. 6,900,187, the contents of which are incorporated herein by reference. A broad range of studies have shown that custirsen potently regulates the expression of clusterin, facilitates cancerous apoptosis, and sensitizes cancerous human prostate, breast, ovarian, lung, renal, bladder, and melanoma cells to chemotherapy (Miyake et al. 2005), see also, U.S. Patent Application Publication No. 2008/0119425 A1. In a clinical trial for androgen-dependent prostate cancer, the drugs flutamide and buserelin were used together in combination with custirsen, increasing prostate cancer cell apoptosis (Chi et al. 2004; Chi et al., 2005).

Hsp90

Heat shock protein 90 (Hsp90) is an ATPase-dependent molecular chaperone required for protein folding, maturation and conformational stabilization of many "client" proteins (Young et al., 2000; Kamal et al., 2003). Hsp90 interacts with several proteins involved in CRPC, including growth factor receptors, cell cycle regulators and signaling kinases like Akt, androgen receptor (AR) or Raf-1, (Whitesell et al., 2005; Takayama et al., 2003). Tumor cells express higher Hsp90 levels compared with benign cells (Kamal et al., 2003; Chiosis et al., 2003), and Hsp90 inhibition has emerged as an exciting target in CRPC and other cancers. Many Hsp90 inhibitors were developed targeting its ATP-binding pocket, including natural compounds such as geldanamycin and its analogs, or synthetic compounds. These agents have been shown to inhibit Hsp90 function and induce apoptosis in preclinical studies of colon, breast, PCa and other cancers (Kamal et al., 2003; Solit et al., 2003; Solit et al., 2002).

Combination Therapy

The administration of two drugs to treat a given condition, such as prostate cancer, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry. In vivo drug metabolism/drug interaction studies—study design, data analysis, and recommendations for dosing and labeling). Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry. In vivo drug metabolism/drug interaction studies—study design, data analysis, and recommendations for dosing and labeling). The interaction may also heighten or lessen the side effects of each drug. Hence, upon administration of two drugs to treat a disease, it is unpredictable what change will occur in the profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry. In vivo drug metabolism/drug interaction studies—study design, data analysis, and recommendations for dosing and labeling).

Thus, the success of one drug or each drug alone in an in vitro model, an animal model, or in humans, may not correlate into efficacy when both drugs are administered to humans.

SUMMARY OF THE INVENTION

The present invention provides a method for treating a mammalian subject affected by prostate cancer comprising administering to the mammalian subject i) an oligonucleotide which reduces clusterin expression and ii) a Heat Shock Protein 90 (Hsp90) inhibitor having the structure:

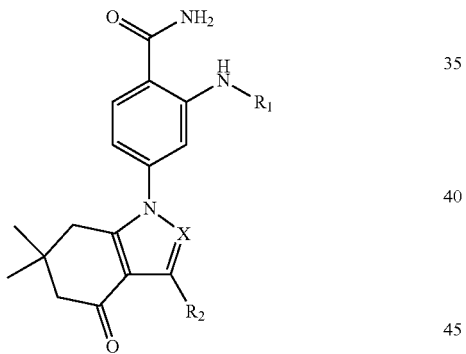

or a pharmaceutically acceptable salt thereof, wherein
$R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-$(C_1$-$C_6)$alkylamino, nitro, halo$(C_1$-$C_6)$alkyl, halo$(C_1$-$C_6)$alkoxy, or carboxamide, wherein
when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, SO$_2$, or SO, with the proviso that two O atoms, two S atoms, or an O and S atom are not immediately adjacent each other, wherein
$R_4$ is
(i) heteroaryl,
(ii) aryl,
(iii) saturated or unsaturated $C_3$-$C_{10}$ cycloalkyl, or
(iv) saturated or unsaturated $C_2$-$C_{10}$ heterocycloalkyl,
wherein
each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—$(C_1$-$C_6)$ alkyl, —SO$_2$$(C_1$-$C_6)$ alkyl, —SO$_2$-aryl, —SO—$(C_1$-$C_6)$alkyl, —SO-aryl, —SO$_2$NH$_2$, —SO$_2$NH—$(C_1$-$C_6)$alkyl, —SO$_2$NH-aryl, $(C_1$-$C_6)$alkoxy, or mono- or di-$(C_1$-$C_{10})$alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$haloalkyl, $C_2$-$C_{10}$alkenyl, $C_2$-$C_{10}$alkynyl, hydroxy, carboxy, carboxamido, oxo, halo, amino, cyano, nitro, —SH, —S—$(C_1$-$C_6)$alkyl, —SO$_2$—$(C_1$-$C_6)$alkyl, —SO$_2$NH$_2$, —SO$_2$NH$(C_1$-$C_6)$alkyl, —SO$_2$NH-aryl, —SO-aryl, —SO—(C1-C6)alkyl, —SO$_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $C_1$-$C_{10}$ alkyl-Z, —O$C_1$-$C_{10}$ alkyl-Z, or $R_5$,
wherein
Z is OR$_o$ or —N(R$_6$)$_2$, wherein
each R$_6$ is independently —H or $C_1$-$C_6$ alkyl, or N(R$_6$)$_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di$(C_1$-$C_6)$alkylamino, $C_1$-$C_6$ alkoxy, or halogen, and
R$_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and
R$_5$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl,
and
the R$_5$ groups are optionally substituted at least one group which is independently hydroxy, oxo, halo, amino, cyano, nitro, —SH, —S—$(C_1$-$C_6)$alkyl, —SO$_2$—$(C_1$-$C_6)$alkyl, —SO$_2$-aryl, —SO—$(C_1$-$C_6)$ alkyl, —SO-aryl, —SO$_2$NH$_2$, —SO$_2$NH—$(C_1$-$C_6)$ alkyl, —SO$_2$NH-aryl, $(C_1$-$C_6)$alkoxy, or mono- or di-$(C_1$-$C_{10})$alkylamino;
$R_2$ is H, Cl, halogen, CF$_3$, CHF$_2$, CH$_3$, $C_1$-$C_{10}$ alkyl, or halo$(C_1$-$C_6)$alkyl; and
X is N or CR$_3$, wherein
R$_3$ is H, halogen, or CH$_3$,
or a prodrug thereof, each in an amount that when in combination with the other is effective to treat the mammalian subject.

Hsp90 inhibitors having structure above are described in U.S. Pat. No. 7,928,135, the entire contents of which are hereby incorporated herein by reference.

The present invention provides a method for treating a mammalian subject affected by prostate cancer comprising administering to the mammalian subject i) an oligonucleotide which reduces clusterin expression and ii) a Hsp90 inhibitor, which inhibitor is other than Hsp90i-1, each in an amount that when in combination with the other is effective to treat the mammalian subject.

The present invention provides a method for treating a mammalian subject affected by prostate cancer comprising administering to the mammalian subject i) an oligonucleotide which reduces clusterin expression and ii) a Hsp90 inhibitor which binds to Hsp90α and Hsp90β with a $K_a$ of less than 50 nmol/L, or a prodrug thereof, each in an amount that when in combination with the other is effective to treat the mammalian subject.

The present invention provides a pharmaceutical composition comprising an amount of an oligonucleotide which reduces clusterin expression, and a Hsp90 inhibitor having the structure:

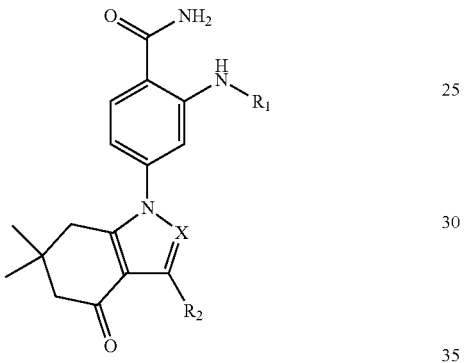

or a pharmaceutically acceptable salt thereof, wherein
$R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein
when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein
$R_4$ is
(i) heteroaryl,
(ii) aryl,
(iii) saturated or unsaturated $C_3$-$C_{10}$ cycloalkyl, or
(iv) saturated or unsaturated $C_2$-$C_{10}$ heterocycloalkyl,
wherein
each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$($C_1$-$C_6$) alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH($C_1$-$C_6$)alkyl, —$SO_2$NH-aryl, —$SO_2$-aryl, —SO—($C_1C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$C_1$-$C_{10}$ alkyl-Z, —$OC_1$-$C_{10}$ alkyl-Z, or $R_5$, wherein
Z is $OR_o$ or —$N(R_6)_2$, wherein
each $R_6$ is independently —H or $C_1$-$C_6$ alkyl, or $N(R_6)_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and
$R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and
$R_5$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl,
and
the $R_5$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NR_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino;
$R_2$ is H, Cl, halogen, $CF_3$, $CHF_2$, $CH_3$, $C_1$-$C_{10}$ alkyl, or halo($C_1$-$C_6$)alkyl; and
X is N or $CR_3$, wherein
$R_3$ is H, halogen, or $CH_3$,
or a prodrug thereof, for use in treating a mammalian subject affected by prostate cancer.

Hsp90 inhibitors having structure above are described in U.S. Pat. No. 7,928,135, the entire contents of which are hereby incorporated herein by reference.

The present invention provides a pharmaceutical composition comprising an amount of an oligonucleotide which reduces clusterin expression, and a Hsp90 inhibitor, which inhibitor is other than Hsp90i-1, for use in treating a mammalian subject affected by prostate cancer.

The present invention provides a pharmaceutical composition comprising an amount of an oligonucleotide which reduces clusterin expression, and a Hsp90 inhibitor which binds to Hsp90α and Hsp90β with a $K_a$ of less than 50 nmol/L, or a prodrug thereof, for use in treating a mammalian subject affected by prostate cancer.

The present invention provides an oligonucleotide which reduces clusterin expression for use in combination with a Hsp90 inhibitor having the structure:

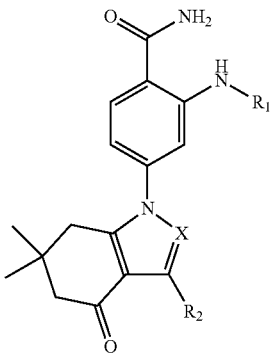

or a pharmaceutically acceptable salt thereof, wherein
  $R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein
    when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein
    $R_4$ is
      (i) heteroaryl,
      (ii) aryl,
      (iii) saturated or unsaturated $C_3$-$C_{10}$ cycloalkyl, or
      (iv) saturated or unsaturated $C_2$-$C_{10}$ heterocycloalkyl,
      wherein
        each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$($C_1$-$C_6$) alkyl, —$SO_2$-aryl, —SO—($C_1$-$C_6$)alkyl, —SO-aryl, —$SO_2NH_2$, —$SO_2NH$—($C_1$-$C_6$)alkyl, —$SO_2NH$-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and
  $R_1$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH(C_1$-$C_6$)alkyl, —$SO_2NH$-aryl, —SO-aryl, —SO—(C1-C6)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, $C_1$-$C_{10}$ alkyl-Z, —O$C_1$-$C_{10}$ alkyl-Z, or $R_5$,
    wherein
    Z is $OR_o$ or —$N(R_6)_2$, wherein
      each $R_6$ is independently —H or $C_1$-$C_6$ alkyl, or $N(R_6)_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and
      $R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and
    $R_5$ is
      (1) heteroaryl,
      (2) aryl,
      (3) saturated or unsaturated $C_5$-$C_{10}$ cycloalkyl, or
      (4) saturated or unsaturated $C_5$-$C_{10}$ heterocycloalkyl,
      and
      the $R_5$ groups are optionally substituted at least one group which is independently hydroxy, oxo, halo, amino, cyano, nitro, —SH, S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NR_2$, —$SO_2NH$—($C_1$-$C_6$)alkyl, —$SO_2NH$-aryl, ($C_1$-$C_6$)alkoxy, or mono- or di-($C_1$-$C_{10}$)alkylamino;
  $R_2$ is H, Cl, halogen, $CF_3$, $CHF_2$, $CH_3$, $C_1$-$C_{10}$ alkyl, or halo($C_1$-$C_6$)alkyl; and
  X is N or $CR_3$, wherein
    $R_3$ is H, halogen, or $CH_3$,
or a prodrug thereof, in treating a mammalian subject affected by prostate cancer.

Hsp90 inhibitors having structure above are described in U.S. Pat. No. 7,928,135, the entire contents of which are hereby incorporated herein by reference.

The present invention provides an oligonucleotide which reduces clusterin expression for use in combination with a Hsp90 inhibitor, which inhibitor is other than Hsp90i-1, in treating a mammalian subject affected by prostate cancer.

The present invention provides an oligonucleotide which reduces clusterin expression for use in combination with a Hsp90 inhibitor which binds to Hsp90α and Hsp90β with a $K_a$ of less than 50 nmol/L, or a prodrug thereof, in treating a mammalian subject affected by prostate cancer.

The present invention provides a composition for treating a mammalian subject affected by prostate cancer comprising i) an oligonucleotide which reduces clusterin expression and ii) a Hsp90 inhibitor having the structure:

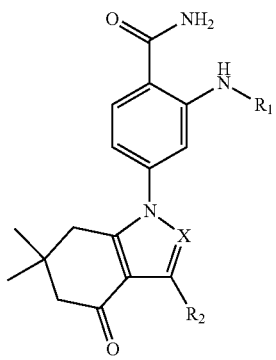

or a pharmaceutically acceptable salt thereof, wherein
$R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein $R_4$ is
(i) heteroaryl,
(ii) aryl,
(iii) saturated or unsaturated $C_3$-$C_{10}$ cycloalkyl, or
(iv) saturated or unsaturated $C_2$-$C_{10}$ heterocycloalkyl,
wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$($C_1$-$C_6$) alkyl, —$SO_2$-aryl, —SO—($C_1$-$C_6$)alkyl, —SO-aryl, —$SO_2NH_2$, —$SO_2NH$—($C_1$-$C_6$)alkyl, —$SO_2NH$-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$ haloalkyl, $C_2$-$C_{10}$alkenyl, $C_2$-$C_{10}$alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$($C_1$-$C_6$)alkyl, —$SO_2NH$-aryl, —SO-aryl, —SO—(C1-C6)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, $C_1$-$C_{10}$ alkyl-Z, —O$C_1$-$C_{10}$ alkyl-Z, or $R_5$,
wherein Z is $OR_o$ or —$N(R_6)_2$, wherein
each $R_6$ is independently —H or $C_1$-$C_6$ alkyl, or $N(R_6)_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and $R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and $R_5$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl,
and the $R_5$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2NH$—($C_1$-$C_6$) alkyl, —$SO_2NH$-aryl, ($C_1$-$C_6$)alkoxy, or mono- or di-($C_1$-$C_{10}$)alkylamino;

$R_2$ is H, Cl, halogen, $CF_3$, $CHF_2$, $CH_3$, $C_1$-$C_{10}$ alkyl, or halo($C_1$-$C_6$)alkyl; and X is N or $CR_3$, wherein
$R_3$ is H, halogen, or $CH_3$, or a prodrug thereof, each in an amount that when in combination with the other is effective to treat the mammalian subject.

The present invention provides a composition for treating a mammalian subject affected by prostate cancer comprising i) an oligonucleotide which reduces clusterin expression and ii) a Hsp90 inhibitor, which inhibitor is other than Hsp90i-1, each in an amount that when in combination with the other is effective to treat the mammalian subject.

The present invention provides a composition for treating a mammalian subject affected by prostate cancer comprising i) an oligonucleotide which reduces clusterin expression and ii) a Hsp90 inhibitor which binds to Hsp90α and Hsp90β with a $K_a$ of less than 50 nmol/L, or a prodrug thereof, each in an amount that when in combination with the other is effective to treat the mammalian subject.

DETAILED DESCRIPTION OF THE INVENTION

Figure 1:
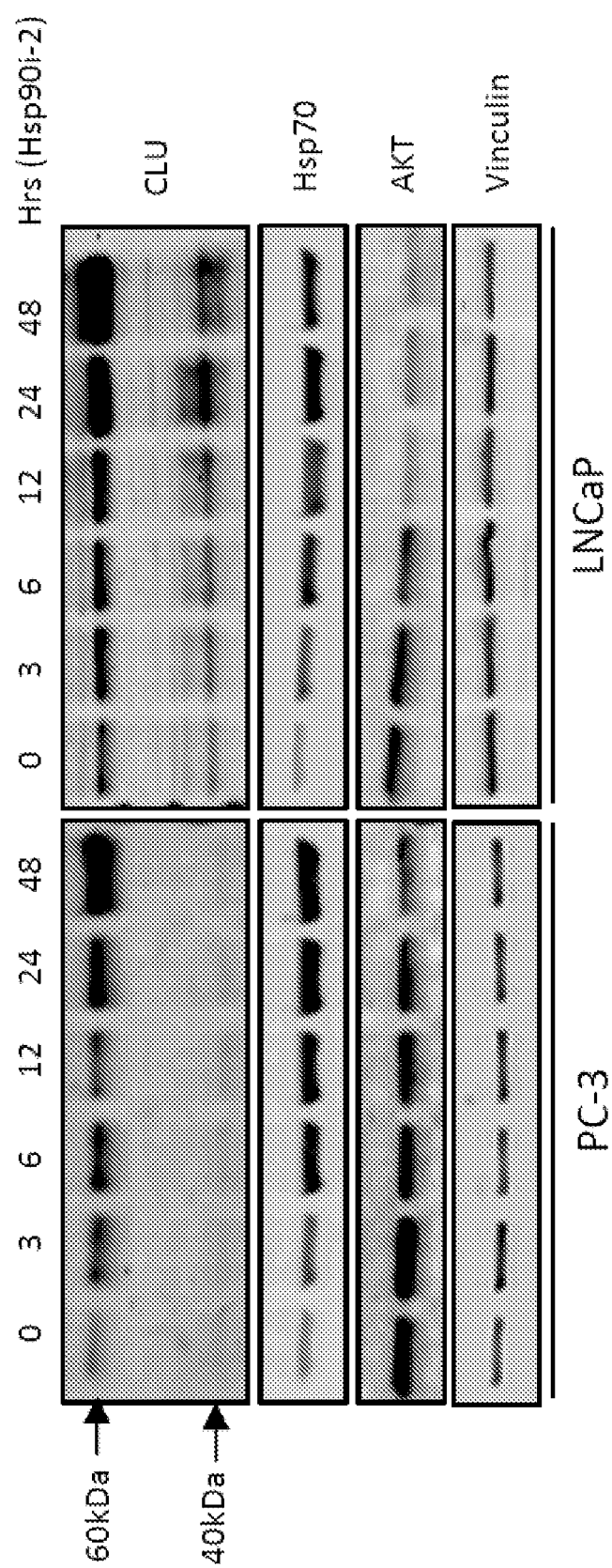
FIG. 1. Hsp90i-1 and Hsp90i-2 induce HSPs and clusterin (CLU) expression in prostate cancer (PCa) cells in vitro. PC-3 and LNCaP cells were treated with 1 μM Hsp90i-2 (A) or 1 μM Hsp90i-1 (C) for the indicated time points. In parallel, PC-3 and LNCaP cells were treated for 48 h with Hsp90i-2 for the indicated doses (B). Protein extracts were analyzed for CLU, Hsp70, Akt and vinculin. Tumor cells were treated for 24 h with 1 μM Hsp90i-2 or 1 μM Hsp90i-1 (D). mRNA extracts were analyzed by real-time PCR for CLU, Hsp90 and Hsp70. ***, p<0.001.
Figure 1:
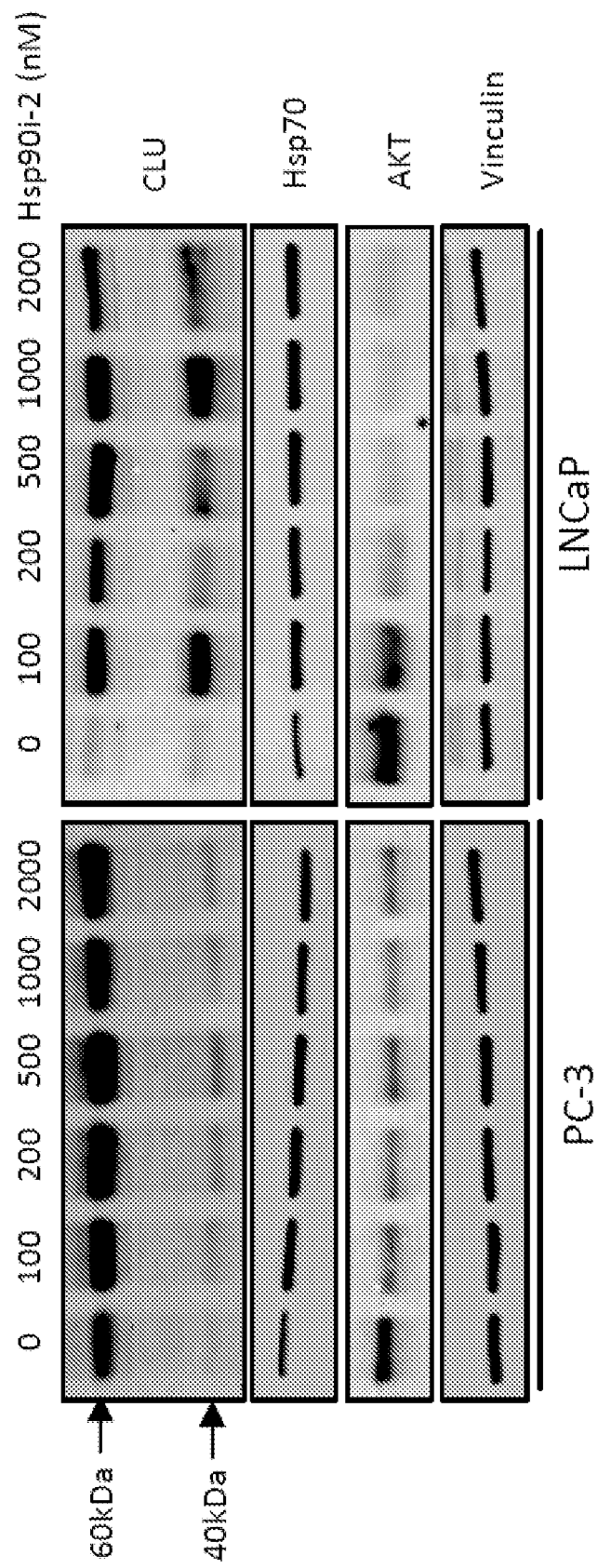
Figure 1:
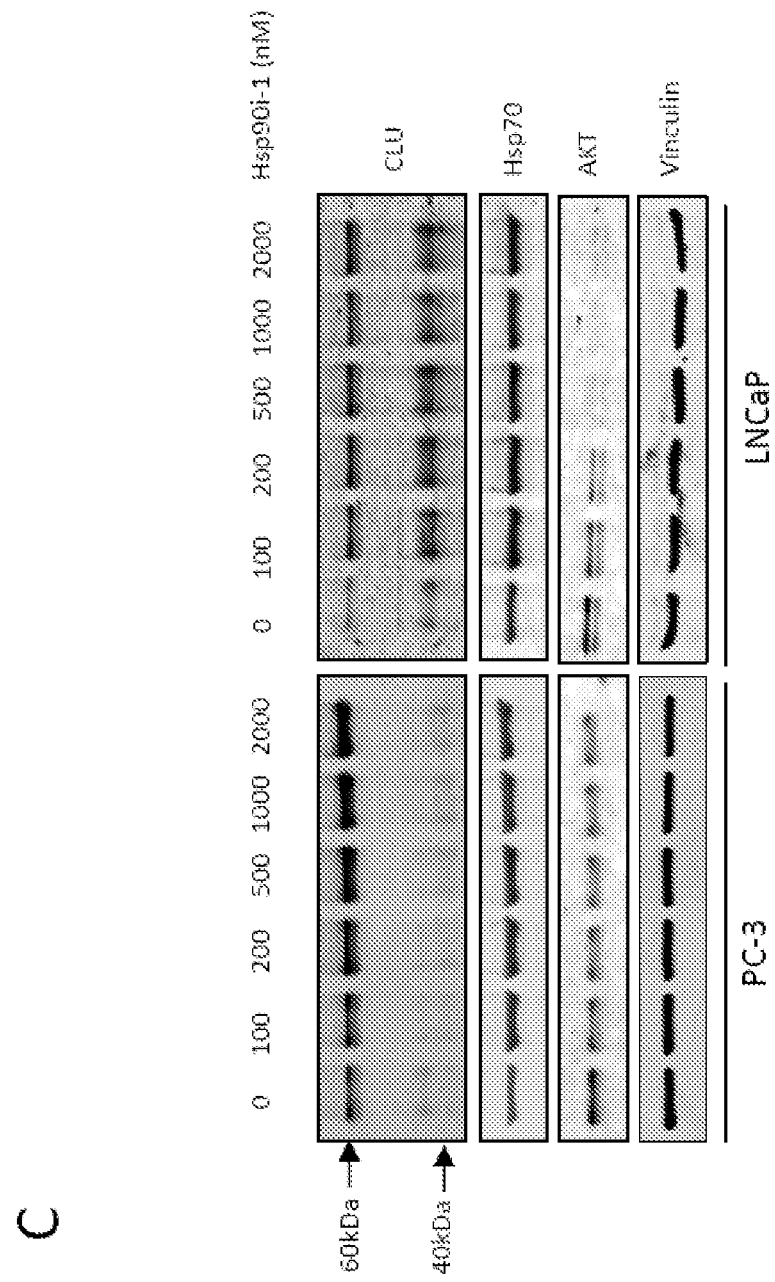
Figure 1:
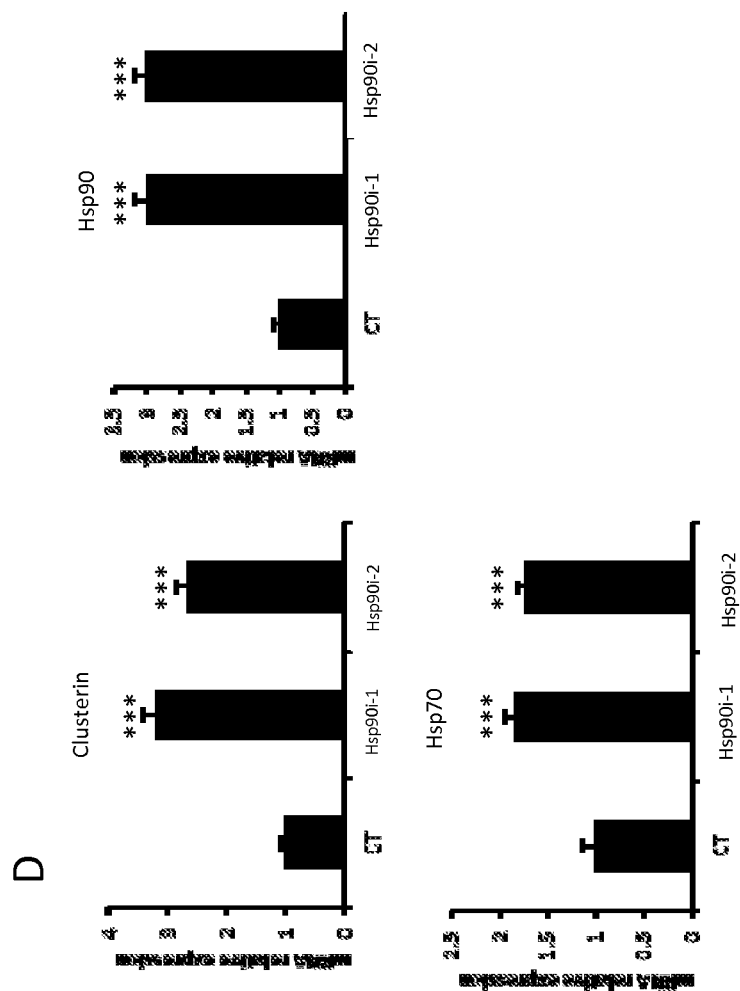

The present invention provides a method for treating a mammalian subject affected by prostate cancer comprising administering to the mammalian subject i) an oligonucleotide which reduces clusterin expression and ii) a Heat Shock Protein 90 (Hsp90) inhibitor having the structure:

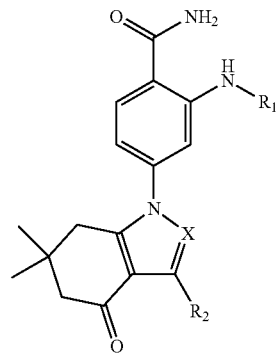

or a pharmaceutically acceptable salt thereof, wherein
$R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein
when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein
$R_4$ is
(i) heteroaryl,
(ii) aryl,
(iii) saturated or unsaturated $C_3$-$C_{10}$ cycloalkyl, or
(iv) saturated or unsaturated $C_2$-$C_{10}$ heterocycloalkyl,
wherein
each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$($C_1$-$C_6$) alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$ haloalkyl, $C_2$-$C_{10}$alkenyl, $C_2$-$C_{10}$alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH($C_1$-$C_6$)alkyl, —$SO_2$NH-aryl, —SO-aryl, —SO—(C1-C6)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$C_1$-$C_{10}$ alkyl-Z, —O$C_1$-$C_{10}$ alkyl-Z, or $R_5$, wherein Z is $OR_o$ or —N($R_6$)$_2$, wherein each $R_6$ is independently —H or $C_1$-$C_6$ alkyl, or N($R_6$)$_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and $R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and $R_5$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl, and the $R_5$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino;

$R_2$ is H, Cl, halogen, $CF_3$, $CHF_2$, $CH_3$, $C_1$-$C_{10}$ alkyl, or halo($C_1$-$C_6$)alkyl; and X is N or $CR_3$, wherein $R_3$ is H, halogen, or $CH_3$, or a prodrug thereof, each in an amount that when in combination with the other is effective to treat the mammalian subject.

The present invention provides a method for treating a mammalian subject affected by prostate cancer comprising administering to the mammalian subject i) an oligonucleotide which reduces clusterin expression and ii) a Hsp90 inhibitor, which inhibitor is other than Hsp90i-1, each in an amount that when in combination with the other is effective to treat the mammalian subject.

The present invention provides a method for treating a mammalian subject affected by prostate cancer comprising administering to the mammalian subject i) an oligonucleotide which reduces clusterin expression and ii) a Hsp90 inhibitor which binds to Hsp90a and Hsp90β with a $K_a$ of less than 50 nmol/L, or a prodrug thereof, each in an amount that when in combination with the other is effective to treat the mammalian subject.

In some embodiments, the Hsp90 inhibitor binds to Hsp90a and/or Hsp90p with a $K_a$ of less than about 70, 60, 50, 40, 35, 30, 25, 20, 15, 10, or 5 nmol/L.

In some embodiments, the cancer is androgen-independent prostate cancer.

In some embodiments, the amount of the oligonucleotide and the amount of the Hsp90 inhibitor when taken together is more effective to treat the subject than when each agent is administered alone.

In some embodiments, the amount of the oligonucleotide in combination with the amount of the Hsp90 inhibitor is less than is clinically effective when administered alone.

In some embodiments, the amount of the Hsp90 inhibitor in combination with the amount of the oligonucleotide is less than is clinically effective when administered alone.

In some embodiments, the amount of the oligonucleotide and the amount of the Hsp90 inhibitor when taken together is effective to reduce a clinical symptom of prostate cancer in the subject.

In some embodiments, the mammalian subject is human.

In some embodiments, the oligonucleotide is an antisense oligonucleotide.

In some embodiments, the antisense oligonucleotide spans either the translation initiation site or the termination site of clusterin-encoding mRNA.

In some embodiments, the antisense oligonucleotide comprises nucleotides in the sequence set forth in SEQ ID NOs: 1 to 11.

In some embodiments, the antisense oligonucleotide comprises nucleotides in the sequence set forth in SEQ ID NO: 3.

In some embodiments, the antisense oligonucleotide is modified to enhance in vivo stability relative to an unmodified oligonucleotide of the same sequence.

In some embodiments, the oligonucleotide is custirsen.

In some embodiments, the amount of custirsen is less than 640 mg.

In some embodiments, the amount of custirsen is less than 480 mg.

In some embodiments, the amount of custirsen is administered intravenously once in a seven day period.

In some embodiments, the amount of the Hsp90 inhibitor is less than 50 mg/kg.

In some embodiments, the amount of the Hsp90 inhibitor is 25 mg/kg or less.

In some embodiments, the Hsp90 inhibitor is Hsp90i-2.

In some embodiments, a prodrug of the Hsp90 inhibitor is administered to the mammalian subject which prodrug is Hsp90i-2-PRO.

In some embodiments, a prodrug of the Hsp90 inhibitor is administered to the mammalian subject which prodrug is Hsp90i-2-PRO2.

In some embodiments, the combination of the oligonucleotide and the Hsp90 inhibitor is effective to inhibit the proliferation of prostate cancer cells.

The present invention provides a pharmaceutical composition comprising an amount of an oligonucleotide which reduces clusterin expression, and a Hsp90 inhibitor having the structure:

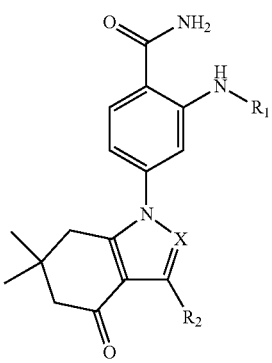

or a pharmaceutically acceptable salt thereof, wherein $R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein $R_4$ is
(i) heteroaryl,
(ii) aryl,
(iii) saturated or unsaturated $C_3$-$C_{10}$ cycloalkyl, or
(iv) saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$ ($C_1$-$C_6$) alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$ haloalkyl, $C_2$-$C_{10}$alkenyl, $C_2$-$C_{10}$alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH($C_1$-$C_6$)alkyl, —$SO_2$NH-aryl, —SO-aryl, —SO—(C1-C6)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$C_1$-$C_{10}$ alkyl-Z, —O$C_1$-$C_{10}$ alkyl-Z, or $R_5$, wherein Z is $OR_o$ or —N($R_6$)$_2$, wherein each $R_6$ is independently —H or $C_1$-$C_6$ alkyl, or N($R_6$)$_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and $R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and $R_5$ is
(1) heteroaryl,
(2) aryl,
(3) saturated or unsaturated cycloalkyl, or
(4) saturated or unsaturated heterocycloalkyl, and the $R_5$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino;

$R_2$ is H, Cl, halogen, $CF_3$, $CHF_2$, $CH_3$, $C_1$-$C_{10}$ alkyl, or halo($C_1$-$C_6$)alkyl; and X is N or $CR_3$, wherein
$R_3$ is H, halogen, or $CH_3$, or a prodrug thereof, for use in treating a mammalian subject affected by prostate cancer.

The present invention provides a pharmaceutical composition comprising an amount of an oligonucleotide which reduces clusterin expression, and a Hsp90 inhibitor, which inhibitor is other than Hsp90i-1, for use in treating a mammalian subject affected by prostate cancer.

The present invention provides a pharmaceutical composition comprising an amount of an oligonucleotide which reduces clusterin expression, and a Hsp90 inhibitor which binds to Hsp90a and Hsp90β with a $K_d$ of less than 50 nmol/L, or a prodrug thereof, for use in treating a mammalian subject affected by prostate cancer.

The present invention provides an oligonucleotide which reduces clusterin expression for use in combination with a Hsp90 inhibitor having the structure:

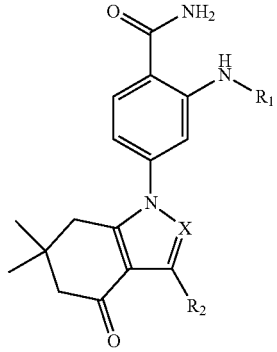

or a pharmaceutically acceptable salt thereof, wherein $R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein $R_4$ is
  (i) heteroaryl,
  (ii) aryl,
  (iii) saturated or unsaturated $C_3$-$C_{10}$ cycloalkyl, or
  (iv) saturated or unsaturated $C_2$-$C_{10}$ heterocycloalkyl,
wherein
each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$($C_1$-$C_6$) alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$ haloalkyl, $C_2$-$C_{10}$alkenyl, $C_2$-$C_{10}$alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH($C_1$-$C_6$)alkyl, —$SO_2$NH-aryl, —SO-aryl, —SO—(C1-C6)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$C_1$-$C_{10}$ alkyl-Z, —O$C_1$-$C_{10}$ alkyl-Z, or $R_5$ wherein Z is $OR_o$ or —$N(R_6)_2$, wherein
each $R_6$ is independently —H or $C_1$-$C_6$ alkyl, or $N(R_6)_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and
$R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and $R_5$ is
  (1) heteroaryl,
  (2) aryl,
  (3) saturated or unsaturated $C_5$-$C_{10}$ cycloalkyl, or
  (4) saturated or unsaturated $C_5$-$C_{10}$ heterocycloalkyl,
and
the $R_5$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino;

$R_2$ is H, Cl, halogen, $CF_3$, $CHF_2$, $CH_3$, $C_1$-$C_{10}$ alkyl, or halo($C_1$-$C_6$)alkyl; and X is N or $CR_3$, wherein
  $R_3$ is H, halogen, or $CH_3$, or a prodrug thereof, in treating a mammalian subject affected by prostate cancer.

The present invention provides an oligonucleotide which reduces clusterin expression for use in combination with a Hsp90 inhibitor, which inhibitor is other than Hsp90i-1, in treating a mammalian subject affected by prostate cancer.

The present invention provides an oligonucleotide which reduces clusterin expression for use in combination with a Hsp90 inhibitor which binds to Hsp90α and Hsp90β with a $K_a$ of less than 50 nmol/L, or a prodrug thereof, in treating a mammalian subject affected by prostate cancer.

The present invention provides a composition for treating a mammalian subject affected by prostate cancer comprising i) an oligonucleotide which reduces clusterin expression and ii) a Hsp90 inhibitor having the structure:

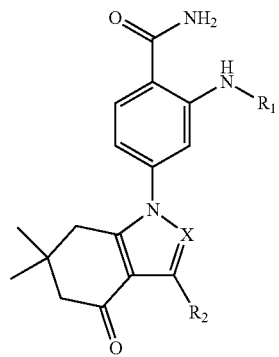

or a pharmaceutically acceptable salt thereof, wherein
$R_1$ is H, $C_1$-$C_{14}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide, wherein when $R_1$ is a $C_1$-$C_{14}$ alkyl group, up to five of the carbon atoms in the alkyl group are optionally replaced independently by $R_4$, carbonyl, ethenyl, ethynyl or a moiety selected from N, O, S, $SO_2$, or SO, with the proviso that two O atoms, two S atoms, or an O and S atom are not immediately adjacent each other, wherein $R_4$ is
  (i) heteroaryl,
  (ii) aryl,
  (iii) saturated or unsaturated $C_3$-$C_{10}$ cycloalkyl, or
  (iv) saturated or unsaturated $C_2$-$C_{10}$ heterocycloalkyl,
wherein
each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$($C_1$-$C_6$) alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and $R_4$ is optionally fused to a $C_6$-$C_{10}$ aryl group, $C_5$-$C_8$ saturated cyclic group, or a $C_4$-$C_{10}$ heterocycloalkyl group; and $R_1$ is optionally substituted at any available position with $C_1$-$C_{10}$ alkyl, $C_1$-$C_{10}$ haloalkyl, $C_2$-$C_{10}$alkenyl, $C_2$-$C_{10}$alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH($C_1$-$C_6$)alkyl, —$SO_2$NH-aryl, —SO-aryl, —SO—(C1-C6)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$C_1$-$C_{10}$ alkyl-Z, —O$C_1$-$C_{10}$ alkyl-Z, or $R_5$,
wherein
Z is O$R_o$ or —N($R_6$)$_2$, wherein
each $R_6$ is independently —H or $C_1$-$C_6$ alkyl, or N($R_6$)$_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen, and
$R_o$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl; and
$R_5$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl,
and
the $R_5$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NR_2$, —$SO_2$NH—($C_1$-$C_6$) alkyl, —$SO_2$NH-aryl, ($C_1$-$C_6$)alkoxy, or mono- or di-($C_1$-$C_{10}$)alkylamino;
$R_2$ is H, Cl, halogen, $CF_3$, $CHF_2$, $CH_3$, $C_1$-$C_{10}$ alkyl, or halo($C_1$-$C_6$)alkyl; and
X is N or $CR_3$, wherein
$R_3$ is H, halogen, or $CH_3$,
or a prodrug thereof, each in an amount that when in combination with the other is effective to treat the mammalian subject.

The present invention provides a composition for treating a mammalian subject affected by prostate cancer comprising i) an oligonucleotide which reduces clusterin expression and ii) a Hsp90 inhibitor, which inhibitor is other than Hsp90i-1, each in an amount that when in combination with the other is effective to treat the mammalian subject.

The present invention provides a composition for treating a mammalian subject affected by prostate cancer comprising i) an oligonucleotide which reduces clusterin expression and ii) a Hsp90 inhibitor which binds to Hsp90α and Hsp90β with a $K_a$ of less than 50 nmol/L, or a prodrug thereof, each in an amount that when in combination with the other is effective to treat the mammalian subject.

In some embodiments, the combination of the oligonucleotide and the Hsp90 inhibitor is effective to inhibit the proliferation of prostate cancer cells.

In some embodiments, Hsp90 inhibitor-mediated induction of clusterin expression is attenuated by custirsen, wherein the combination of the Hsp90 inhibitor and custirsen delays the progression of CRPC. In some embodiments, the combination of the Hsp90 inhibitor and custirsen inhibits tumor growth in the mammalian subject. In some embodiments, the combination of the Hsp90 inhibitor and custirsen prolongs the survival of the mammalian subject.

An aspect of the invention provides pharmaceutical composition comprising an amount of an oligonucleotide which reduces clusterin expression, and a Hsp90 inhibitor for use in treating a mammalian subject affected by prostate cancer.

An aspect of the invention provides oligonucleotide which reduces clusterin expression for use in combination with a Hsp90 inhibitor in treating a mammalian subject affected by prostate cancer.

An aspect of the invention provides a composition for treating a mammalian subject affected by prostate cancer comprising i) an oligonucleotide which reduces clusterin expression and ii) a Hsp90 inhibitor each in an amount that when in combination with the other is effective to treat the mammalian subject.

Aspects of the invention involve the increased potency of a combination treatment comprising an oligonucleotide that targets clusterin expression and an Hsp90 inhibitor compared to oligonucleotide or Hsp90 inhibitor monotherapy. In some embodiments of the invention, the combination of an oligonucleotide that targets clusterin expression and an HSP90 inhibitor increases prostate cancer cell apoptosis and/or decreases prostate cancer cell proliferation compared to oligonucleotide or Hsp90 inhibitor monotherapy. In some embodiments, the combination of an oligonucleotide that targets clusterin expression and an Hsp90 inhibitor decreases the protein expression and/or a function of HSF-1 compared to oligonucleotide or Hsp90 inhibitor monotherapy.

Aspects of the invention provide targeted strategies employing an oligonucleotide which reduces clusterin expression in combination with Hsp90 inhibitors to improve patient outcome in castration-resistant prostate cancer.

The present invention relates to a method for treating a mammalian subject affected by prostate cancer comprising i) an oligonucleotide which reduces clusterin expression and ii) a Heat Shock Protein 90 (Hsp90) inhibitor, each in an amount that when in combination with the other is effective to treat the mammalian subject.

In some embodiments, the Hsp90 inhibitor is Hsp90i-1.

Each embodiment disclosed herein is contemplated as being applicable to each of the other disclosed embodiments. Thus, all combinations of the various elements described herein are within the scope of the invention.

It is understood that where a parameter range is provided, all integers within that range, and tenths thereof, are also provided by the invention. For example, "0.2-5 mg/kg/day" includes 0.2 mg/kg/day, 0.3 mg/kg/day, 0.4 mg/kg/day, 0.5 mg/kg/day, 0.6 mg/kg/day etc. up to 5.0 mg/kg/day.

Terms

As used herein, and unless stated otherwise, each of the following terms shall have the definition set forth below.

As used herein, "about" in the context of a numerical value or range means±10% of the numerical value or range recited or claimed.

As used in the specification and claims of this application, the term "clusterin" refers to a glycoprotein present in mammals, including humans, and denominated as such in the humans. The sequences of numerous clusterin species are known. For example, the sequence of human clusterin is described by Wong et al., Eur. J. Biochem. 221 (3), 917-925 (1994), and in NCBI sequence accession number NM_001831 (SEQ ID NO: 43). In this human sequence, the coding sequence spans bases 48 to 1397.

As used herein, "oligonucleotide which reduces clusterin expression" is an oligonucleotide with a sequence which is effective to reduce clusterin expression in a cell. The oligonucleotide which reduces clusterin expression may be, for example, an antisense oligonucleotide or an RNA interference inducing molecule.

As used herein, "antisense oligonucleotide" refers to a non-RNAi oligonucleotide that reduces clusterin expression and that has a sequence complementary to clusterin mRNA. Antisense oligonucleotides may be antisense oligodeoxynucleotides (ODN). Exemplary sequences which can be employed as antisense molecules in the invention are disclosed in PCT Patent Publication WO 00/49937, U.S. Patent Publication US-2002-0128220-A1, and U.S. Pat. No. 6,383,808, all of which are incorporated herein by reference. Specific antisense sequences are set forth in the present application as SEQ ID NOs: 1 to 11, and may be found in Table 1.

TABLE 1

Sequence Identification Numbers for Antisense Oligonucleotides

| SEQ ID NO: | Sequence |
|---|---|
| 1 | GCACAGCAGG AGAATCTTCA T |
| 2 | TGGAGTCTTT GCACGCCTCG G |
| 3 | CAGCAGCAGA GTCTTCATCA T |
| 4 | ATTGTCTGAG ACCGTCTGGT C |
| 5 | CCTTCAGCTT TGTCTCTGAT T |
| 6 | AGCAGGGAGT CGATGCGGTC A |
| 7 | ATCAAGCTGC GGACGATGCG G |
| 8 | GCAGGCAGCC CGTGGAGTTG T |
| 9 | TTCAGCTGCT CCAGCAAGGA G |
| 10 | AATTTAGGGT TCTTCCTGGA G |
| 11 | GCTGGGCGGA GTTGGGGCC T |

The ODNs employed may be modified to increase the stability of the ODN in vivo. For example, the ODNs may be employed as phosphorothioate derivatives (replacement of a non-bridging phosphoryl oxygen atom with a sulfur atom) which have increased resistance to nuclease digestion. MOE (2'-O-(2-methoxyethyl)) modification (ISIS backbone) is also effective. The construction of such modified ODNs is described in detail in U.S. Pat. No. 6,900,187 B2, the contents of which are incorporated by reference. In some embodiments, the ODN is custirsen.

As used herein, "custirsen" refers to an antisense oligonucleotide that reduces clusterin expression having the sequence CAGCAGCAGAGTCTTCATCAT (SEQ ID NO: 3), wherein the anti-clusterin oligonucleotide has a phosphorothioate backbone throughout, has sugar moieties of nucleotides 1-4 and 18-21 bearing 2'-O-methoxyethyl modifications, has nucleotides 5-17 which are 2' deoxynucleotides, and has 5-methylcytosines at nucleotides 1, 4, and 19. Custirsen is also known as TV-1011, OGX-011, ISIS 112989 and Custirsen Sodium.

As used herein, "RNA inducing molecule" refers to a molecule capable of inducing RNA interference or "RNAi" of clusterin expression. RNAi involves mRNA degradation, but many of the biochemical mechanisms underlying this interference are unknown. The use of RNAi has been described in Fire et al., 1998, Carthew et al., 2001, and Elbashir et al., 2001, the contents of which are incorporated herein by reference.

Isolated RNA molecules can mediate RNAi. That is, the isolated RNA molecules of the present invention mediate degradation or block expression of mRNA that is the transcriptional product of the gene, which is also referred to as a target gene. For convenience, such mRNA may also be referred to herein as mRNA to be degraded. The terms RNA, RNA molecule(s), RNA segment(s) and RNA fragment(s) may be used interchangeably to refer to RNA that mediates RNA interference. These terms include double-stranded RNA, small interfering RNA (siRNA), hairpin RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides Or deoxyribonucleotides. Collectively, all such altered RNAi molecules are referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be affected by the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA.

As noted above, the RNA molecules of the present invention in general comprise an RNA portion and some additional portion, for example a deoxyribonucleotide portion. The total number of nucleotides in the RNA molecule is suitably less than in order to be effective mediators of RNAi. In preferred RNA molecules, the number of nucleotides is 16 to 29, more preferably 18 to 23, and most preferably 21-23. Suitable sequences are set forth in the present application as SEQ ID NOs:19 to 42 (Table 2).

TABLE 2

Sequence Identification Numbers for RNA Interference Inducing Molecules

| SEQ ID NO: | Sequence |
|---|---|
| 19 | CCAGAGCUCG CCCUUCUACT T |
| 20 | GUAGAAGGGC GAGCUCUGGT T |
| 21 | GAUGCUCAAC ACCUCCUCCT T |
| 22 | GGAGGAGGUG UUGAGCAUCT T |
| 23 | UAAUUCAACA AAACUGUTT |
| 24 | GACAGUUUUA UUGAAUUAGT T |
| 25 | UAAUUCAACA AAACUGUTT |
| 26 | ACAGUUUUGU UGAAUUATT |
| 27 | AUGAUGAAGA CUCUGCUGCT T |
| 28 | GCAGCAGAGU CUUCAUCAUT T |
| 29 | UGAAUGAAGG GACUAACCUG TT |
| 30 | CAGGUUAGUC CCUUCAUUCA TT |
| 31 | CAGAAAUAGA CAAAGUGGGG TT |
| 32 | CCCCACUUUG UCUAUUUCUG TT |
| 33 | ACAGAGACUA AGGGACCAGA TT |
| 34 | ACAGAGACUA AGGGACCAGA TT |
| 35 | CCAGAGCUCG CCCUUCUACT T |
| 36 | GUAGAAGGGC GAGCUCUGGT T |
| 37 | GUCCCGCAUC GUCCGCAGCT T |
| 38 | GCUGCGGACG AUGCGGGACT T |
| 39 | CUAAUUCAAU AAAACUGUCT T |
| 40 | GACAGUUUUA UUGAAUUAGT T |
| 41 | AUGAUGAAGA CUCUGCUGC |
| 42 | GCAGCAGAGU CUUCAUCAU |

The siRNA molecules of the invention are used in therapy to treat patients, including human patients, that have cancers or other diseases of a type where a therapeutic benefit is obtained by the inhibition of expression of the targeted protein. siRNA molecules of the invention are administered to patients by one or more daily injections (intravenous, subcutaneous or intrathecal) or by continuous intravenous or intrathecal administration for one or more treatment cycles to reach plasma and tissue concentrations suitable for the regulation of the targeted mRNA and protein.

As used herein, a "mammalian subject affected by prostate cancer" means a mammalian subject who was been affirmatively diagnosed to have prostate cancer.

As used herein, "androgen-independent prostate cancer" encompasses cells and tumors containing cells that are not androgen-dependent (not androgen sensitive); often such cells progress from being androgen-dependent to being androgen-independent. In some embodiments, androgen independent prostate cancer has progressed since the administration of hormone ablation therapy and/or hormone blockade therapy. In some embodiments, there is increased AR expression in the androgen-independent prostate cancer compared to prostate cancer that is not androgen-independent.

As used herein, "castration-resistant prostate cancer" encompasses any androgen-independent prostate cancer that is resistant to hormone ablation therapy and/or hormone blockade therapy. In some embodiments, castration-resistant prostate cancer has progressed since the administration of hormone ablation or hormone blockade therapy. In some embodiments, there is increased AR expression in the castration-resistant prostate cancer compared to prostate cancer that is not castration resistant.

As used herein, "Hsp90 inhibitor" refers to an agent that perturbs or reduces a function of Hsp90, including inhibiting a Hsp90-protein interaction, Hsp90 signaling, or Hsp90 protein expression. Hsp90 inhibitors include but are not limited to Hsp90-specific monoclonal antibodies, oligonucleotides that target Hsp90 expression (such as Hsp90 targeting antisense oligonucleotides or RNA inducing molecules), peptide agents specific for Hsp90, and small molecule inhibitors specific for Hsp90. Non-limiting examples of Hsp90 inhibitors are Hsp90i-1, Hsp90i-2, Hsp90i-2-PRO and Hsp90i-2-PRO2.

Hsp90i-1 is a Hsp90 inhibitor. Hsp90i-1 is also known as 17-allylamino-17-demethoxygeldanamycin (17-AAG), Telatinib, Tanespimycin, NSC-330507, CNF-101, KOS-953, GLD-36, and CP 127374. The CAS Registry Number of Hsp90i-1 is 75747-14-7. The Hsp90i-1 used for the experiments described herein is also referred to as 17-AAG and was obtained from the National Institutes of Health (Bethesda, Md., USA). 17-AAG has been discussed in Egorin et al., 1998, and Koga et al., 2009, and is also available for purchase from Invivogen (San Diego, Calif., USA).

Hsp90i-2 is a Hsp90 inhibitor. Hsp90i-2 is also known as PF-04928473, and SNX-2112, and (4-(6,6-Dimethyl-4-oxo-3-trifluoromethyl-4,5,6,7-tetrahydro-indazol-1-yl)-2-(4-hydroxy-cyclohexylamino)-benzamide). The CAS Registry No. for Hsp90i-2 is 908112-43-6. Hsp90i-2 has the following structure:

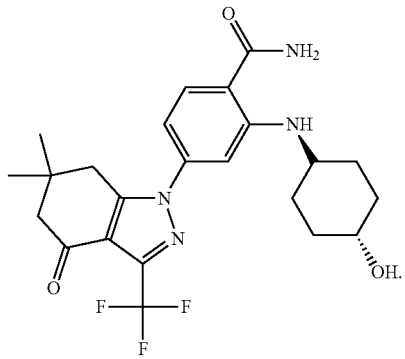

Hsp90i-2 is discussed in Lamoureux et al., 2011, the entire contents of which are incorporated herein by reference.

Hsp90i-2-PRO is a Hsp90 inhibitor. Hsp90i-2-PRO is the prodrug of Hsp90i-2. The CAS Registry No. for Hsp90i-2-PRO is 908115-27-5. Hsp90i-2-PRO is also known as SNX-5422 and PF-04929113. Hsp90i-2-PRO has the following structure:

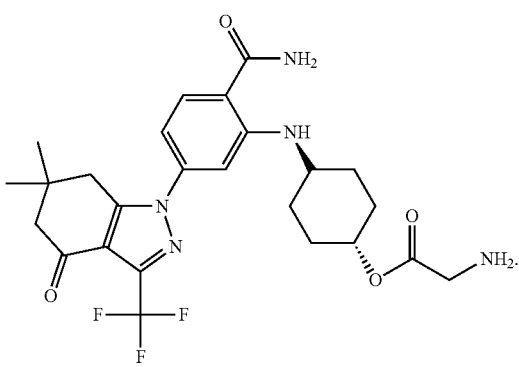

Hsp90i-2-PRO is discussed in Lamoureux et al., 2011, the entire contents of which are incorporated herein by reference.

Hsp90i-2-PRO2 is another prodrug of Hsp90i-2. Hsp90i-2-PRO2 is discussed in Chandarlapaty et al., 2008, the entire contents of which are incorporated herein by reference. Hsp90i-2-PRO2 is also known as SNX-5542.

Methods of synthesis for Hsp90i-2, Hsp90i-2-PRO and Hsp90i-2-PRO2 are described in Huang et al., *J. Med. Chem.* 52:4288-4305 (2009), and U.S. Pat. No. 7,928,135, the entire contents of which are incorporated herein by reference. Alternatively, Hsp90i-2, Hsp90i-2-PRO and Hsp90i-2-PRO2 are available from Pfizer Inc. (New York, N.Y., USA) and Serenex Inc. (Durham, N.C., USA).

Those having ordinary skill in the art of organic synthesis will appreciate that modifications to the general procedures shown in the synthesis schemes of this application can be made to yield structurally diverse compounds. For example, where aryl rings are present, all positional isomers are contemplated and may be synthesized using standard aromatic substitution chemistry. The number and types of substituents may also vary around the aryl rings. Furthermore, where alkyl groups are present, the chain length may be modified using methods well known to those of ordinary skill in the art. Where ester formation is contemplated, lactones may be used wherein the lactone ring is opened by reaction with a nucleophile, such as an ether-containing moiety described hereinabove. Suitable organic transformations are described in March's Advanced Organic Chemistry: Reactions, Mechanisms, and Structure (Wiley-Interscience; 6th edition, 2007), the content of which is hereby incorporated by reference.

Compounds of the subject invention can be converted to prodrugs to optimize absorption and bioavailability. Formation of a prodrug include, but is not limited to, reaction of a free hydroxyl group with a carboxylic acid to form an ester, reaction of a free hydroxyl group with an phosphorus oxychloride followed by hydrolysis to form a phosphate, or reaction of a free hydroxyl group with an amino acid to form an amino acid ester, the process of which has been described previously by Chandran in WO 2005/046575. The substituents are chosen and resulting analogs are evaluated according to principles well known in the art of medicinal and pharmaceutical chemistry, such as quantification of structure-activity relationships, optimization of biological activity and ADMET (absorption, distribution, metabolism, excretion, and toxicity) properties.

Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The alkyl, aryl, and heteroaryl substituents may be substituted or unsubstituted, unless specifically defined otherwise.

The compounds of the instant invention may be in a salt form. As used herein, a "salt" is a salt of the instant compounds which has been modified by making acid or base salts of the compounds. In some embodiments, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The compositions of this invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with additional anticancer agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents.

Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds of the instant invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The inhibition of clusterin expression may be transient, and may occur in combination with a Hsp90 inhibitor. In humans with prostate cancer, this means that inhibition of expression should be effective starting within a day or two of Hsp90 inhibition or administration of an Hsp90 inhibitor, and extending for about 3 to 6 months thereafter. This may require multiple doses to accomplish. It will be appreciated, however, that the period of time may be more prolonged, starting Hsp90 inhibition and extending for substantial time afterwards without departing from the scope of the invention.

Aspects of the invention can be applied to the treatment of androgen-independent prostate cancer, or to prevent prostate cancer from becoming androgen-independent.

Aspects of the invention can be applied to the treatment of castration-resistant prostate cancer, or to prevent prostate cancer from becoming castration-resistant.

"Combination" means either at the same time and frequency, or more usually, at different times and frequencies as an oligonucleotide targeting clusterin expression, as part of a single treatment plan. Aspects of the invention include the administration of the oligonucleotide before, after, and/ or during the administration of a Hsp90 inhibitor. A Hsp90 inhibitor may therefore be used, in combination with an oligonucleotide according to the invention, but yet be administered at different times, different dosages, and at a different frequency, than the oligonucleotide.

As used herein, an "amount" or "dose" of an oligonucleotide measured in milligrams refers to the milligrams of oligonucleotide present in a drug product, regardless of the form of the drug product.

As used herein, "effective" when referring to an amount of oligonucleotide which reduces clusterin expression, a Hsp90 inhibitor, or any combination thereof refers to the quantity of oligonucleotide, Hsp90 inhibitor, or any combination thereof that is sufficient to yield a desired therapeutic response without undue adverse side effects (such as toxicity, irritation, or allergic response) commensurate with a reasonable benefit/risk ratio when used in the manner of this invention.

As used herein, "treating" encompasses, e.g., inhibition, regression, or stasis of the progression of prostate cancer. Treating also encompasses the prevention or amelioration of any symptom or symptoms of prostate cancer.

As used herein, "inhibition" of disease progression or disease complication in a subject means preventing or reducing the disease progression and/or disease complication in the subject.

As used herein, a "symptom" associated with prostate cancer includes any clinical or laboratory manifestation associated with prostate cancer, and is not limited to what the subject can feel or observe.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds and/or combinations to the subject.

The following abbreviations are used herein
PCa prostate cancer
CRPC castrate resistant prostate cancer
HSP heat shock proteins
CLU clusterin
PSA prostate specific antigen
17-AAG 17-allylamino-17-demethoxygeldanamycin
Aso antisense oligonucleotide
Dosage Units Administration of an oligonucleotide that targets clusterin expression can be carried out using the various mechanisms known in the art, including naked administration and administration in pharmaceutically acceptable lipid carriers. For example, lipid carriers for antisense delivery are disclosed in U.S. Pat. Nos. 5,855,911 and 5,417,978, which are incorporated herein by reference. In general, the oligonucleotide is administered by intravenous (i.v.), intraperitoneal (i.p.), subcutaneous (s.c.), or oral routes, or direct local tumor injection. In preferred embodiments, an oligonucleotide targeting clusterin expression is administered by i.v. injection. In some embodiments, the amount of oligonucleotide administered is 640 mg.

The amount of antisense oligonucleotide administered is one effective to inhibit the expression of clusterin in prostate cells. It will be appreciated that this amount will vary both with the effectiveness of the antisense oligonucleotide employed, and with the nature of any carrier used.

The amount of antisense oligonucleotide targeting clusterin expression administered may be from 40 to 640 mg, or 300-640 mg. Administration of the antisense oligonucleotide may be once in a seven day period, 3 times a week, or more specifically on days 1, 3 and 5, or 3, 5 and 7 of a seven day period. In some embodiments administration of the antisense oligonucleotide is less frequent than once in a seven day period. Dosages may be calculated by patient weight, and therefore a dose range of about 1-20 mg/kg, or about 2-10 mg/kg, or about 3-7 mg/kg, or about 3-4 mg/kg could be used. This dosage is repeated at intervals as needed. One clinical concept is dosing once per week with 3 loading doses during week one of treatment. The amount of antisense oligonucleotide administered is one that has been demonstrated to be effective in human patients to inhibit the expression of clusterin in cancer cells.

In some embodiments of the invention, the amount of oligonucleotide targeting the expression of clusterin required for treatment of prostate cancer is less in combination with a Hsp90 inhibitor, than would be required with oligonucleotide monotherapy.

Custirsen may be formulated at a concentration of 20 mg/mL as an isotonic, phosphate-buffered saline solution for IV administration and can be supplied as an 8 mL solution containing 160 mg custirsen sodium in a single vial.

Custirsen may be added to 250 mL 0.9% sodium chloride (normal saline). The dose may be administered using either a peripheral or central indwelling catheter intravenously as an infusion over 2 hours. Additionally, an infusion pump may be used.

Administration of an Hsp90 inhibitor may be oral, nasal, pulmonary, parenteral, i.v., i.p., intra-articular, transdermal, intradermal, s.c., topical, intramuscular, rectal, intrathecal, intraocular, and buccal. One of skill in the art will recognize that higher doses may be required for oral administration than for i.v. injection.

The dose of Hsp90 inhibitor may be 60 mg/kg, 55 mg/kg, 45 mg/kg, 40 mg/kg, 35 mg/kg, 25 mg/kg, 20 mg/kg, 15 mg/kg, 10 mg/kg, 5 mg/kg or less.

A dosage unit of the oligonucleotide which reduces clusterin expression and an Hsp90 inhibitor may comprise one of each singly or mixtures thereof. A combination of an oligonucleotide which reduces clusterin expression and an Hsp90 inhibitor can be administered in oral dosage forms as tablets, capsules, pills, powders, granules, elixirs, tinctures, suspensions, syrups, and emulsions. An oligonucleotide which reduces clusterin expression and/or Hsp90 inhibitor may also be administered in intravenous (bolus or infusion), intraperitoneal, subcutaneous, or intramuscular form, or introduced directly, e.g. by injection or other methods, into or onto a prostate cancer lesion, all using dosage forms well known to those of ordinary skill in the pharmaceutical arts.

An oligonucleotide which reduces clusterin expression and/or Hsp90 inhibitor can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The oligonucleotide and/or Hsp90 inhibitor can be administered alone or mixed with a pharmaceutically acceptable carrier. This carrier can be a solid or liquid, and the type of carrier is generally chosen based on the type of administration being used. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

An oligonucleotide which reduces clusterin expression and/or Hsp90 inhibitor can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

For oral administration in liquid dosage form, an Hsp90 inhibitor may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

In some embodiments of the invention, the amount of Hsp90 inhibitor required for treatment of prostate cancer is less in combination with an oligonucleotide targeting the expression of clusterin, than would be required with Hsp90 monotherapy.

A dosage unit may comprise a single compound or mixtures of compounds. A dosage unit can be prepared for oral or injection dosage forms.

According to an aspect of the invention, there is provided an oligonucleotide which reduces clusterin expression-containing pharmaceutical composition packaged in dosage unit form, wherein the amount of the oligonucleotide in each dosage unit is 640 mg or less. Said pharmaceutical composition may include an Hsp90 inhibitor, and may be in an injectable solution or suspension, which may further contain sodium ions.

According to another aspect of the invention, there is provided the use of an oligonucleotide targeting clusterin expression and a Hsp90 inhibitor in the manufacture of a medicament for the treatment of cancer, where the medicament is formulated to deliver a dosage of 640 mg or less of oligonucleotide to a patient. The medicament may contain sodium ions, and/or be in the form of an injectable solution.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Hsp90 Inhibitors Induce Expression of HSPs in Prostate Cancer (PCa) Cells In Vitro and In Vivo Dose- and time-dependent effects of Hsp90i-1 or Hsp90i-2 on the expression of CLU, Hsp90, Hsp70 and Akt protein and mRNA levels was evaluated in LNCaP and PC-3 cells. Both Hsp90i-1 and Hsp90i-2 increased Hsp70 and CLU protein levels up to 3 fold in a dose- and time-dependent manner (FIGS. 1A, B and C). Hsp90 inhibition induced a dose- and a time dependent decline of Akt expression as previously reported (Lamoureux et al., 2011). mRNA levels of CLU, Hsp70 and Hsp90 also increased after Hsp90 inhibitor treatment (FIG. 1D).

Figure 2:
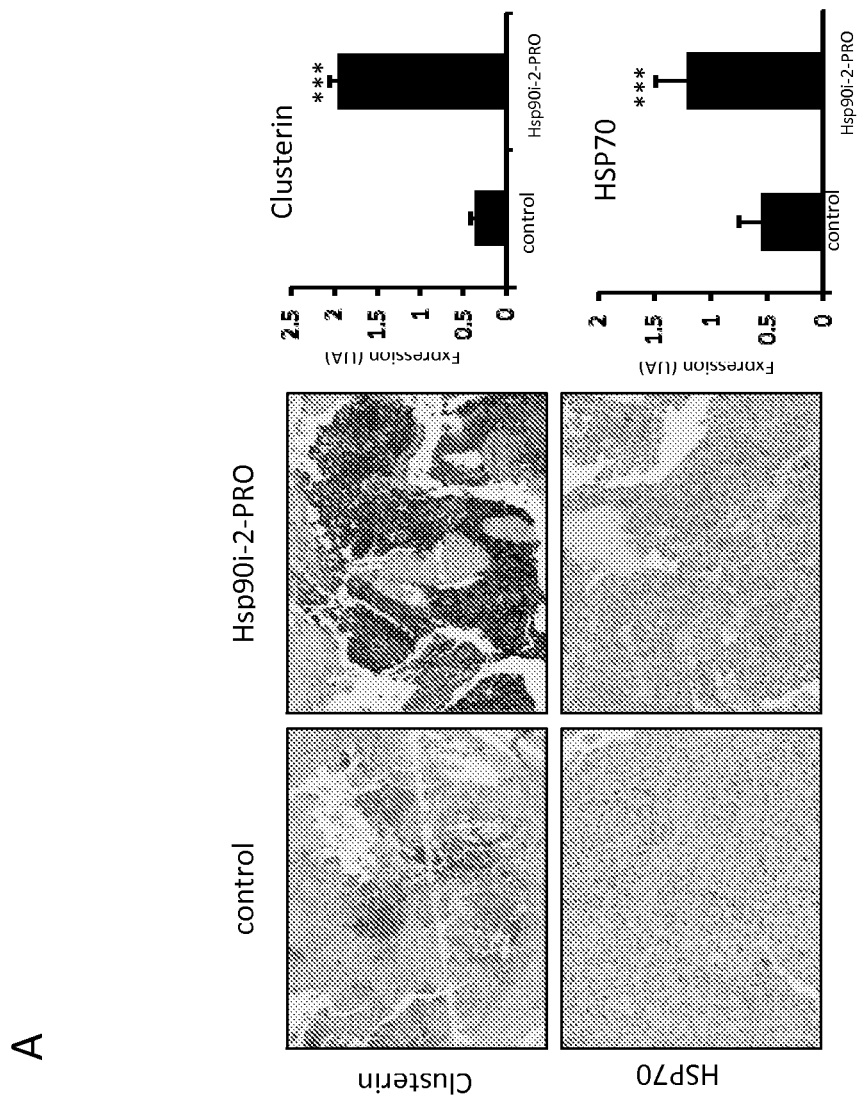
FIG. 2. Hsp90i-2 induces HSP and CLU expression in PCa xenografts. Mice were treated for 6 weeks with 50 mg/kg Hsp90i-2-PRO (the prodrug of Hsp90i-2) or vehicle (Control). A, tumors were collected and CLU and Hsp70 were evaluated by immunohistochemical analysis. B, total proteins were extracted from the xenograft tumors and CLU expression was analyzed by western blotting. The relative levels were normalized with GAPDH and estimated in densitometric units. ***, p<0.001.
Figure 2:
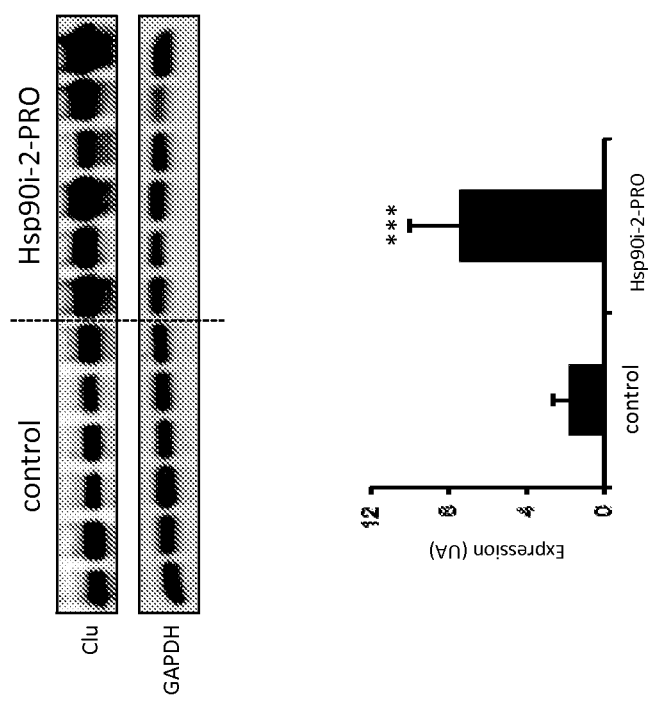

Next the effects of Hsp90i-2 treatment on CLU expression were assessed in vivo in CRPC LNCaP xenografts using immunohistochemistry and western blot (FIG. 2). CLU expression increased 4-fold after treatment with Hsp90i-2-PRO (*, p<0.001) compared with vehicle treated tumor (FIGS. 2A, B). Similarly, Hsp70, which is considered a pharmacodynamic measure of Hsp90 inhibition (Solit et al., 2003; Eccles et al., 2008), increased 2.3-fold after treatment with Hsp90i-2-PRO (*, p<0.001) (FIG. 2A).

Example 2

Treatment-Induced Feed Forward Loop Involving CLU and HSF-1 Activity

Figure 3:
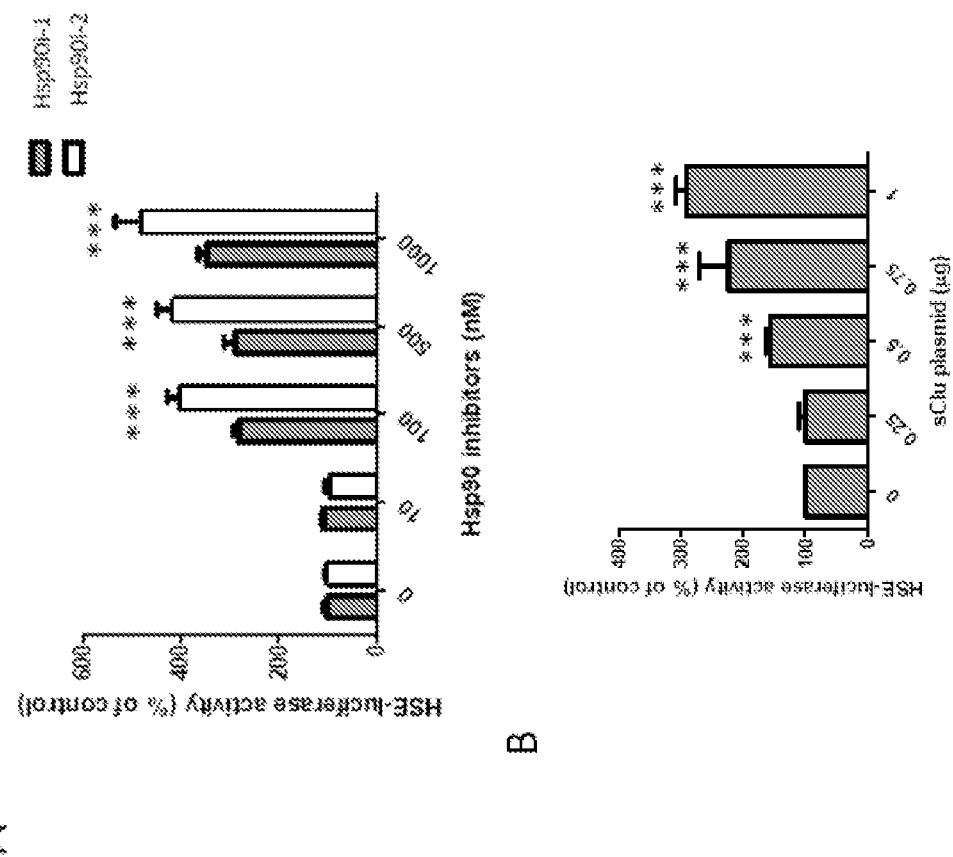
FIG. 3. CLU induction following Hsp90 inhibitor treatment is cytoprotective via an increase of HSF-1 activity. A, LNCaP cells were treated with indicated concentrations of Hsp90i-1 or Hsp90i-2 for 48 h. B, LNCaP cells were transiently transfected with indicated concentrations of CLU-plasmid for 48 h. Total amount of plasmid DNA transfected was normalized to 2 μg per well by the addition of an empty vector. C (Top), LNCaP cells were transfected with 20 nM CLU siRNA or control siScr, followed by Hsp90i-1 or Hsp90i-2 treatment (1 μM) for 48 h. C (bottom), LNCaP cells were treated twice with 300 nM custirsen or control ScrB ASO. D, LNCaP and PC-3 cells were treated twice with 300 nM custirsen or control ScrB ASO, followed by 1 μM of Hsp90i-1 or Hsp90i-2 for 48 h. Cells were harvested, and HSE-luciferase activity or western blotting analyses were performed. Means of at least three independent experiments done in triplicate. ***, p<0.001; *, p<0.05; ns, not significant.
Figure 3:
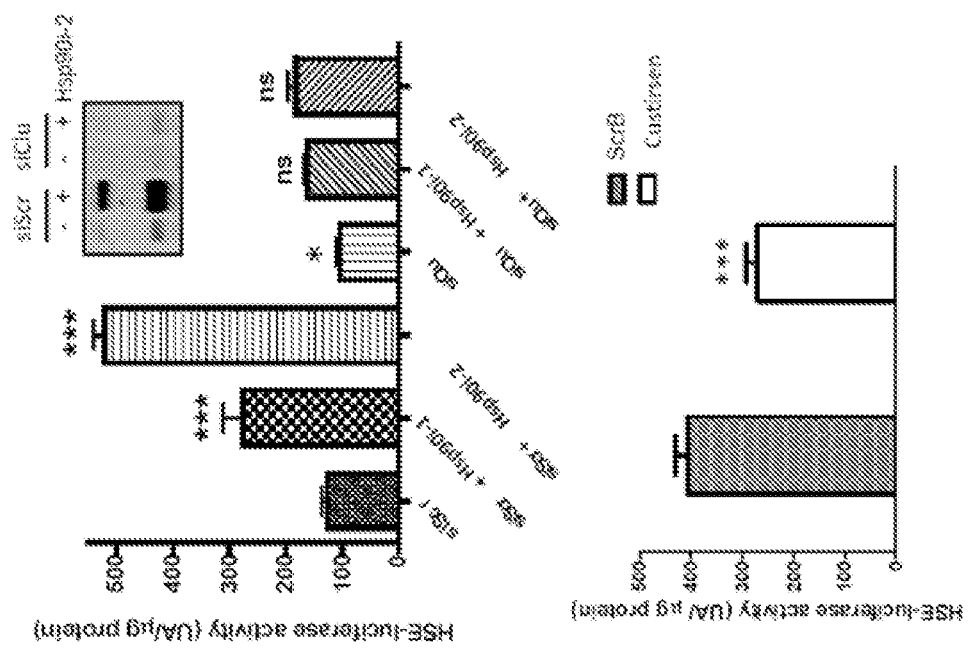
Figure 3:
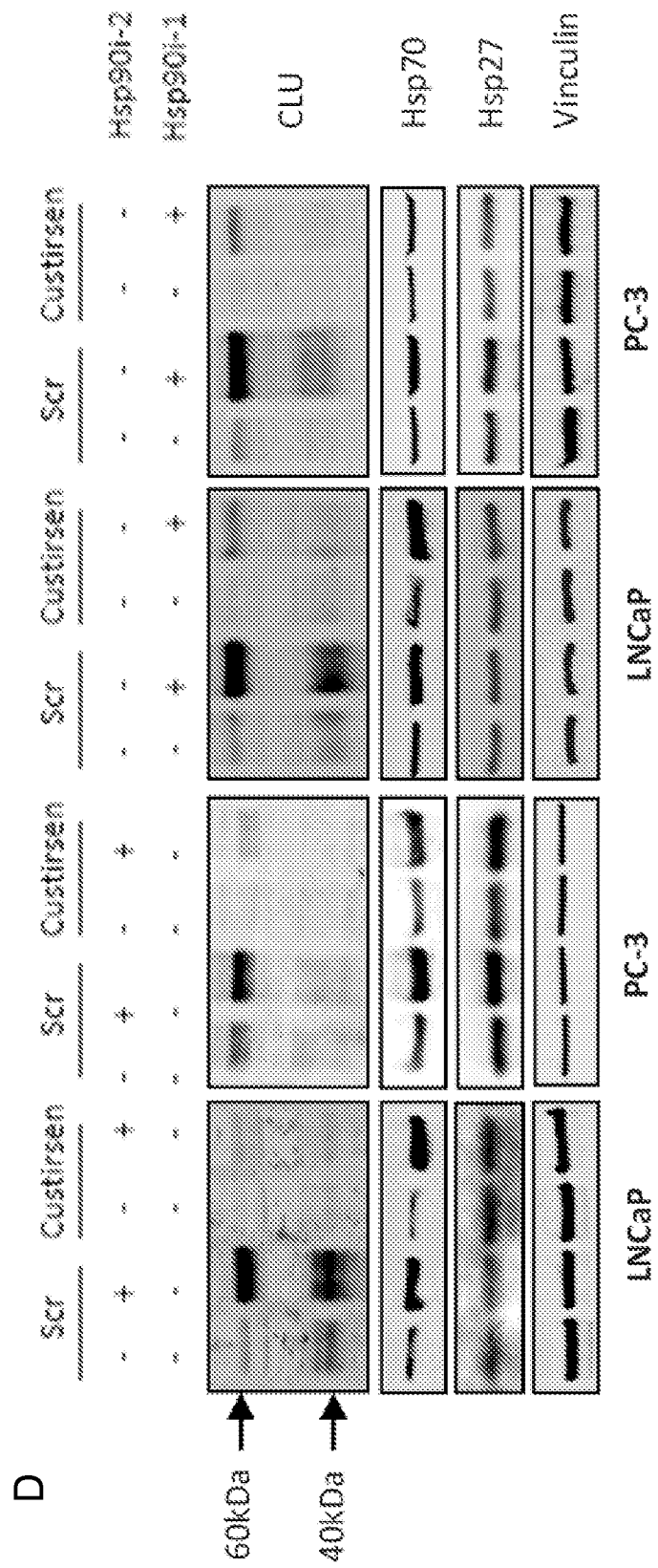
Figure 8:
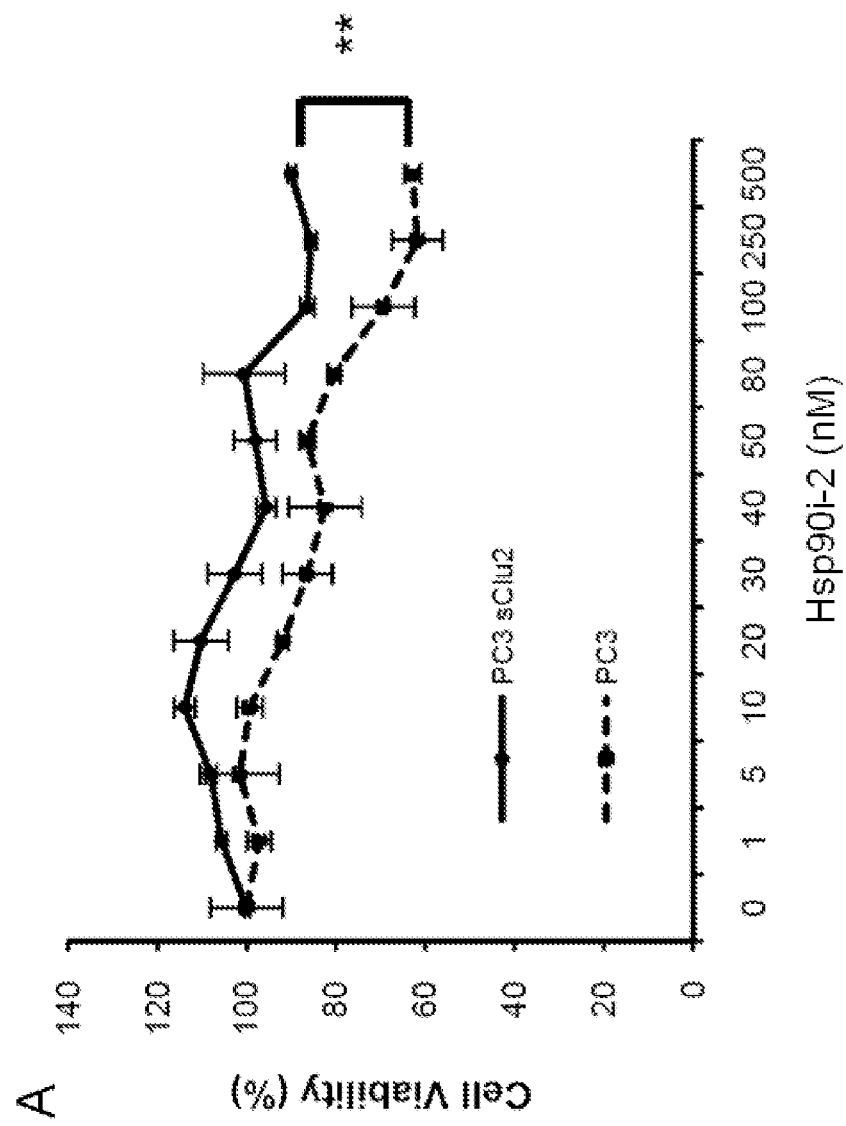
FIG. 8. Clusterin protects tumor cells to Hsp90 inhibitors via a regulation of HSF-1. A, PC-3 cells were transfected to overexpress CLU compared to wt-PC-3 and treated with indicated concentrations of Hsp90i-2 for 48 h. Cell growth was determined by crystal violet and compared with control. **, p≤0.01, tumor cells were treated with 20 nM HSF-1 siRNA vs control Scr siRNA and treated with 1 μM Hsp90i-2 for 48 h. Total proteins were extracted and, western blotting and caspase 3/7 activity were performed. C, PC-3 cells were treated with 20 nM CLU siRNA vs control Scr siRNA and treated with 1 μM Hsp90i-1 for 24 h. HSF-1 localization was assessed by immunofluorescence staining.
Figure 8:
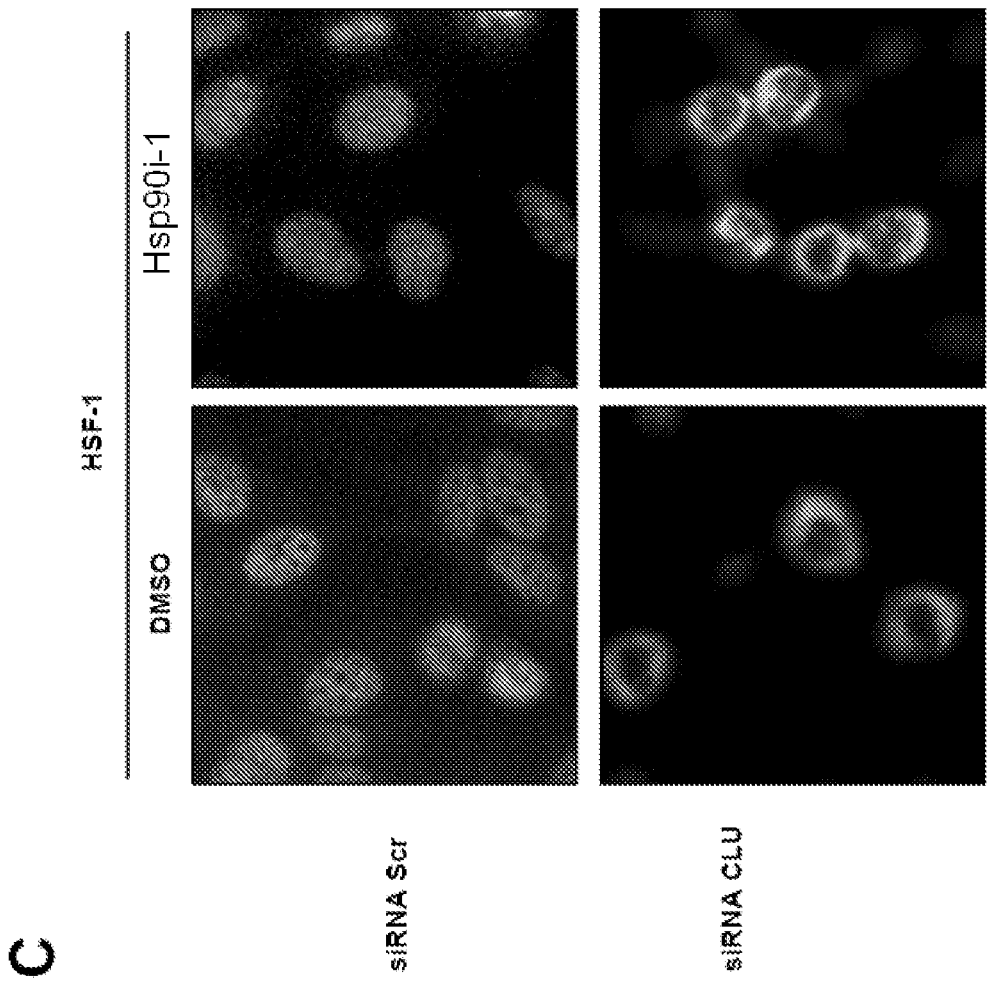
Figure 9:
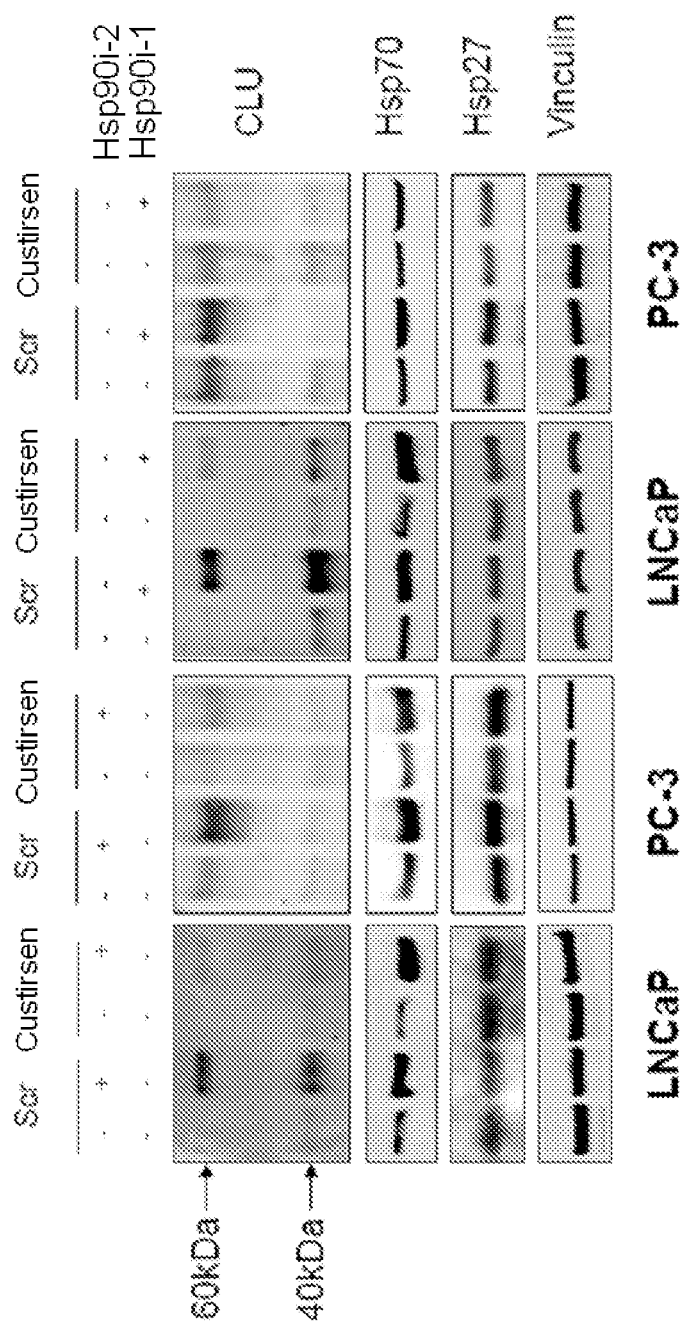
FIG. 9. LNCaP and PC-3 cells were treated twice with 300 nM custirsen or control ScrB ASO, followed by 1 μM of Hsp90i-1 or Hsp90i-2 for 48 h. Cells were harvested, and HSE-luciferase activity or western blotting analyses were performed.

Since HSF-1 is the pre-dominant regulator of the heat shock response (Banerji et al., 2008; Workman et al., 2007), the effect of Hsp90 inhibition on HSF-1-activity and expression of HSPs was evaluated. Hsp90i-1 or Hsp90i-2 significantly induced CLU (FIG. 1) as well as HSF-1 activity in a dose-dependent manner (*, p≤0.001; FIG. 3A). CLU overexpression protected PC-3 tumor cells from Hsp90i-2-induced apoptosis (p≤0.01; FIG. 8A). Moreover, HSF-1 knockdown using siRNA decreases CLU expression, sensitizing tumor cells to apoptosis-induced by Hsp90i-2 (FIG. 8B), confirming that the protective effect of CLU is mediated by HSF-1. Surprisingly, overexpression of CLU also increased HSF-1 activity (***, $p\leq0.001$, FIG. 3B), while CLU knockdown using siRNA or custirsen significantly decreased HSF-1 activity (*, $p\leq0.05$; ***, $p\leq0.001$; FIG. 3C), identifying novel feed-forward regulation of HSF-1 by CLU. Indeed, silencing of CLU inhibited HSF-1 transcriptional activity-induced by Hsp90i-1 or Hsp90i-2 (FIG. 3C), as well as HSF-1 regulated genes such as Hsp27 and Hsp70 (FIG. 3D). This effect can be explained by the ability of CLU knockdown to sequester HSF-1 in the cytoplasm (FIG. 8B).

Example 3

Figure 4:
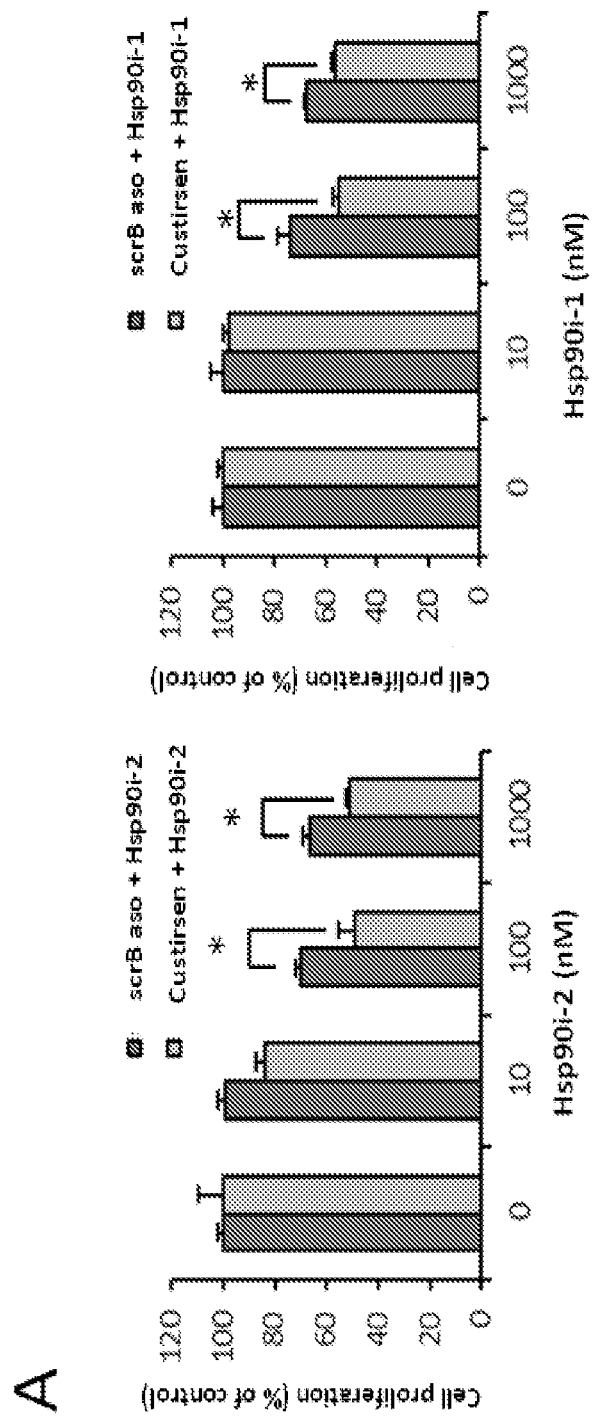
FIG. 4. Increased potency of CLU knockdown and Hsp90 inhibitor combination treatment in PCa cells. A, LNCaP cells were treated twice with 300 nM custirsen or control ScrB ASO, followed by the indicated concentration of Hsp90i-1 or Hsp90i-2 for 48 h. Cell growth was determined by crystal violet and compared with control. B, dose dependent effects and combination index (CI) values calculated by CalcuSyn software were assessed in LNCap cells treated for 48 h with custirsen alone, Hsp90i-2 alone or combined treatment at indicated concentration with constant ratio design between both drugs. The CI for $ED_{50}$ and $ED_{75}$ was 0.4 and 0.75, respectively, indicative of a combination effect of this combined treatment. C and D, LNCaP cells were treated twice with 300 nM custirsen or control ScrB, followed by 1 μM Hsp90i-1 or Hsp90i-2 for 48 h. Cells were harvested, and western blotting analyses were performed (C). The proportion of cells in subG1, G0-G1, S, G2-M was determined by propidium iodide staining and caspase-3 activity was determined on the cell lysates and the results are expressed in arbitrary units and corrected for protein content (D). All experiments were repeated at least thrice. $$$, p<0.001; *, p<0.001; , p<0.01 *, p<0.05.
Figure 4:
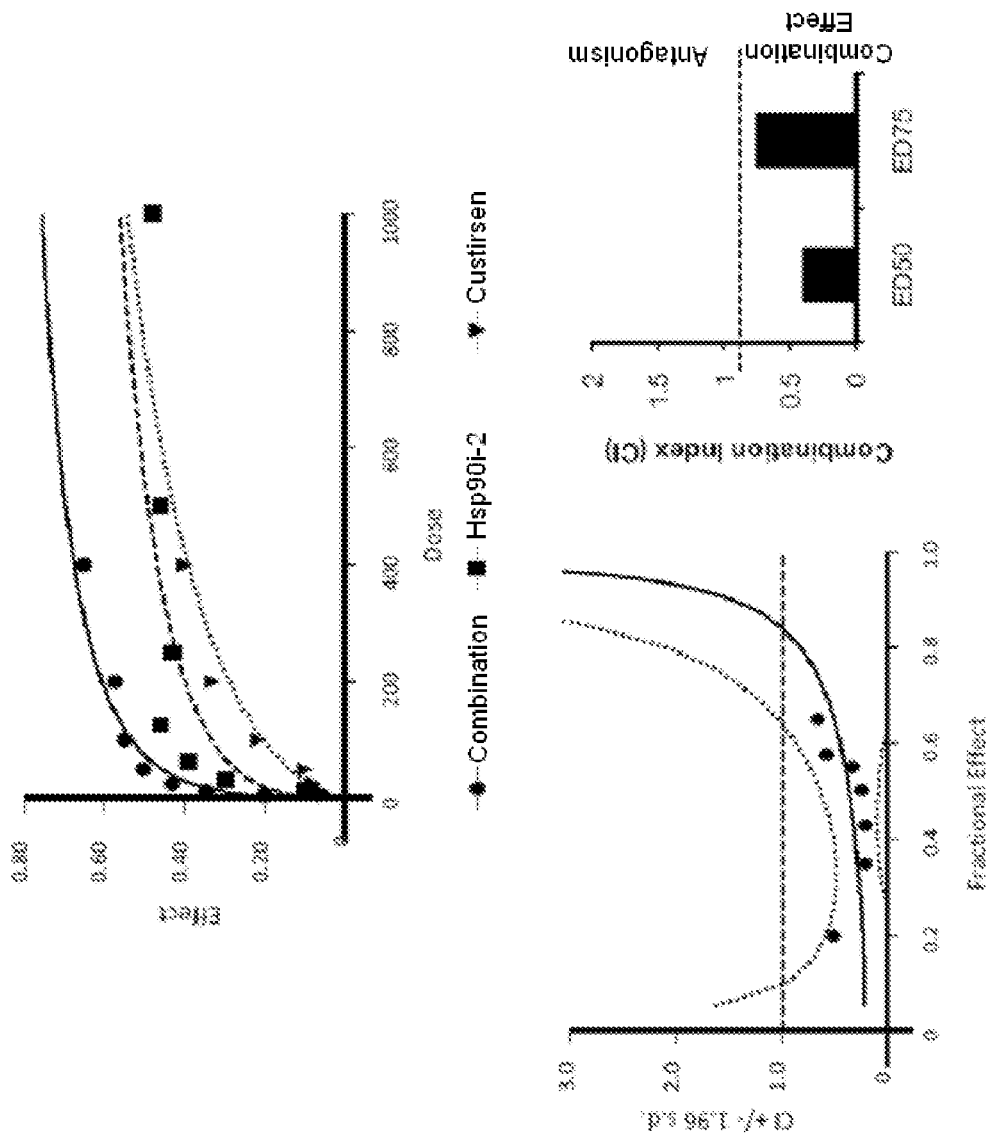
Figure 4:
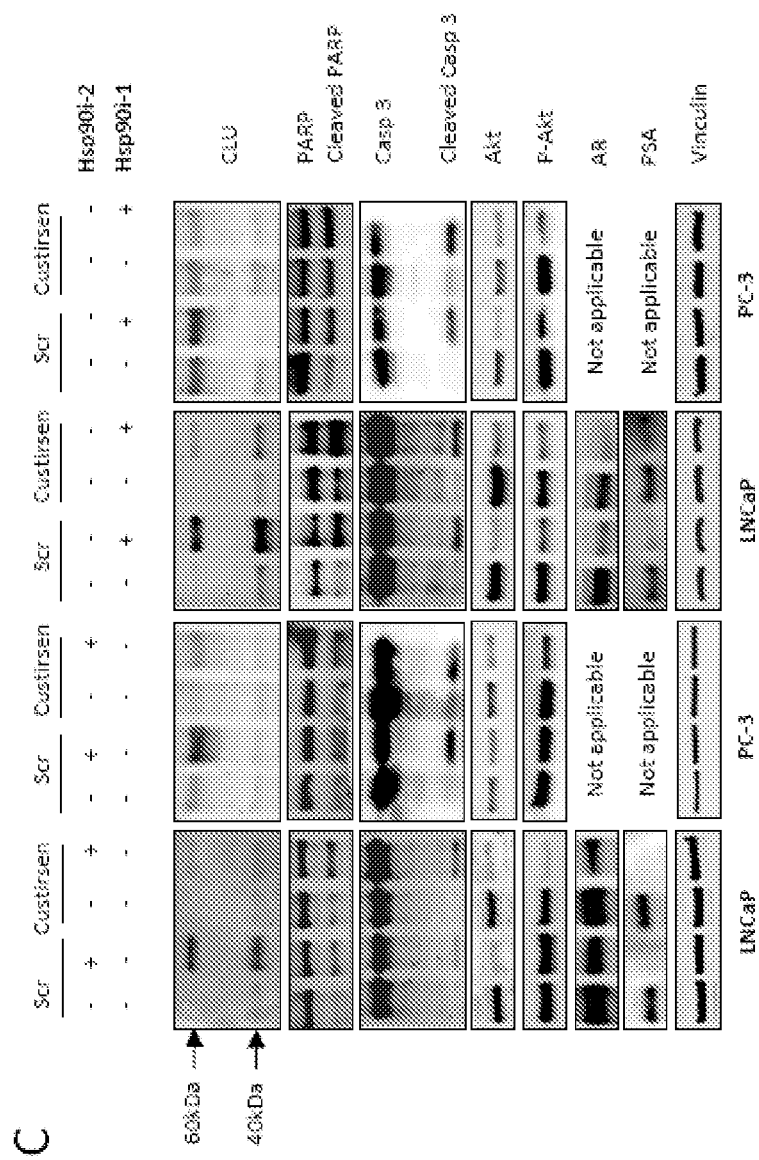
Figure 4:
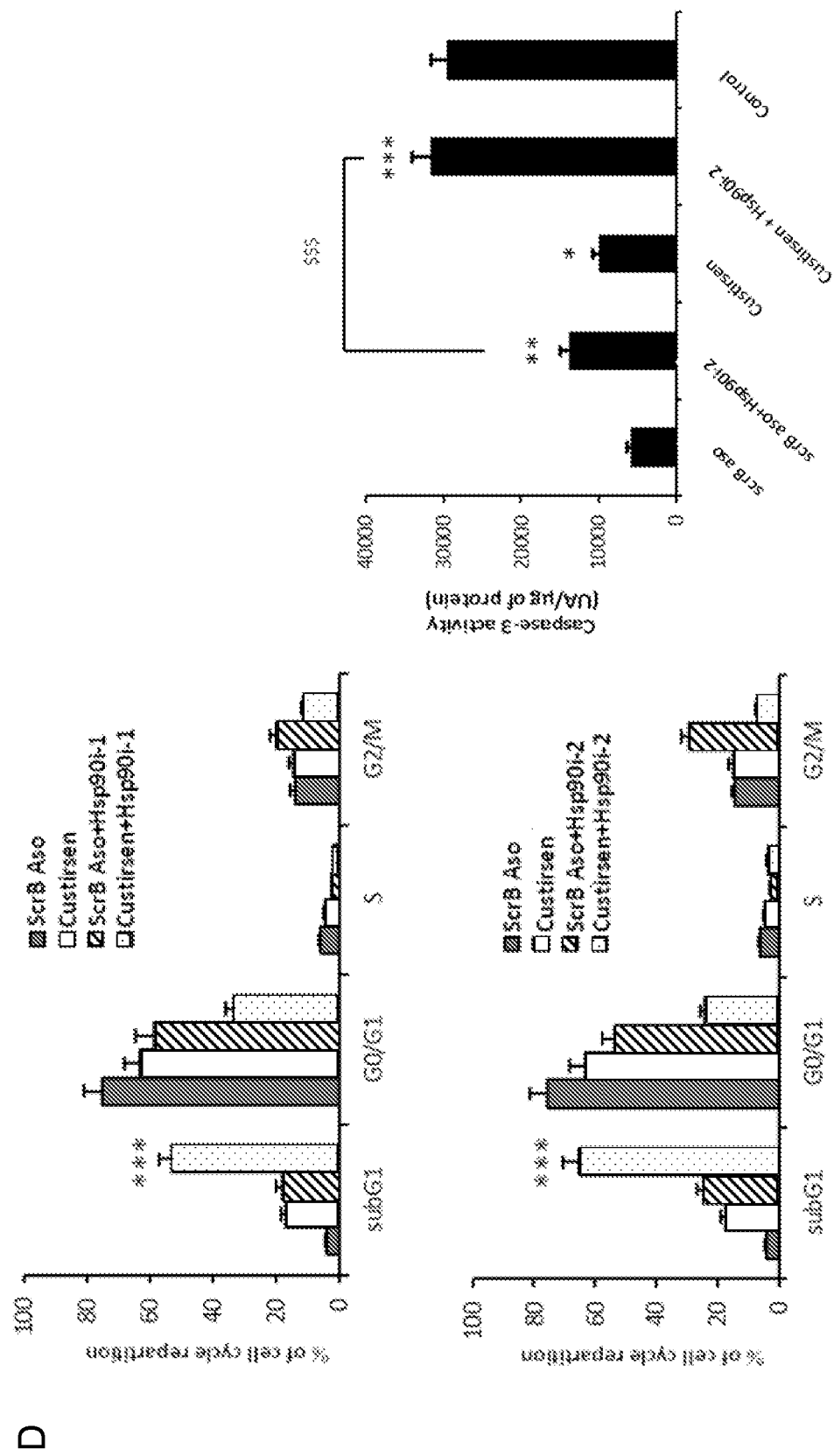

Increased Potency of Combination Treatment Comprising Custirsen and Hsp90 Inhibitor in Increasing Apoptosis in Prostate Tumor Cell Lines Compared to Monotherapy Since Hsp90 inhibitors induce up-regulation of CLU and functions as a mediator in treatment resistance (Zoubeidi et al. 2010; Gleave et al., 2005; Zellweger et al., 2003), it was next evaluated if CLU knockdown combined with Hsp90 inhibition increased treatment effectiveness. LNCaP cells were treated with custirsen and subsequently treated with indicated concentrations of Hsp90i-1 or Hsp90i-2. The combination had significantly enhanced Hsp90i-1 or Hsp90i-2 effectiveness, reducing cell viability by 20% at 100 nM and 1000 nM (*, p<0.05) compared with cells treated with control ScrB ASO and Hsp90 inhibitors (FIG. 4A). To determine whether this effect was additive or a combination effect, the dose-dependent effects
with constant ratio design and the combination index (CI) values was performed and calculated according to the Chou and Talalay median effect principal (Chou et al., 1984). FIG. 4B shows the dose response curve (combination treatment, custirsen or HSP90i-2 monotherapy) and the combination index plots, indicating that custirsen and HSP90i-2 had enhanced combined potency on tumor cell growth compared to custirsen or Hsp90i-2 inhibitor monotherapy.

Moreover, OGX-011 potentiates the effect of Hsp90 inhibitor to induce apoptosis (FIGS. 4C and D). Flow cytometric analysis shows that apoptotic rates (subG1 fraction) increased significantly (p<0.001) when custirsen is combined with Hsp90i-1 (53%) or Hsp90i-2(65.4%), compared to control ScrB ASO (4.2%), custirsen alone (17.4%), control ScrB ASO+Hsp90i-1 (18.3%) or control ScrB ASO+Hsp90i-2 (24.8%; FIG. 4C). Moreover, the combination custirsen with Hsp90i-1 or Hsp90i-2 induced more caspase-dependent apoptosis compared to Hsp90 inhibitor- or custirsen monotherapy, as shown by cleaved PARP and caspase-3 expression (FIG. 4C). The significant increase of caspase-3 activity confirms that custirsen sensitizes cells to Hsp90 inhibition with increased apoptotic rates (FIG. 4D). Reduced cell viability from combined CLU plus Hsp90 inhibition results, in part, from decreases in p-Akt levels in both PC-3 and LNCaP cells, as well as AR (and PSA) expression in LNCaP cells (FIG. 4C).

Example 4

Potent Combination Therapy of Custirsen and Hsp90i-1 in PC-3 Xenografts In Vivo

Figure 5:
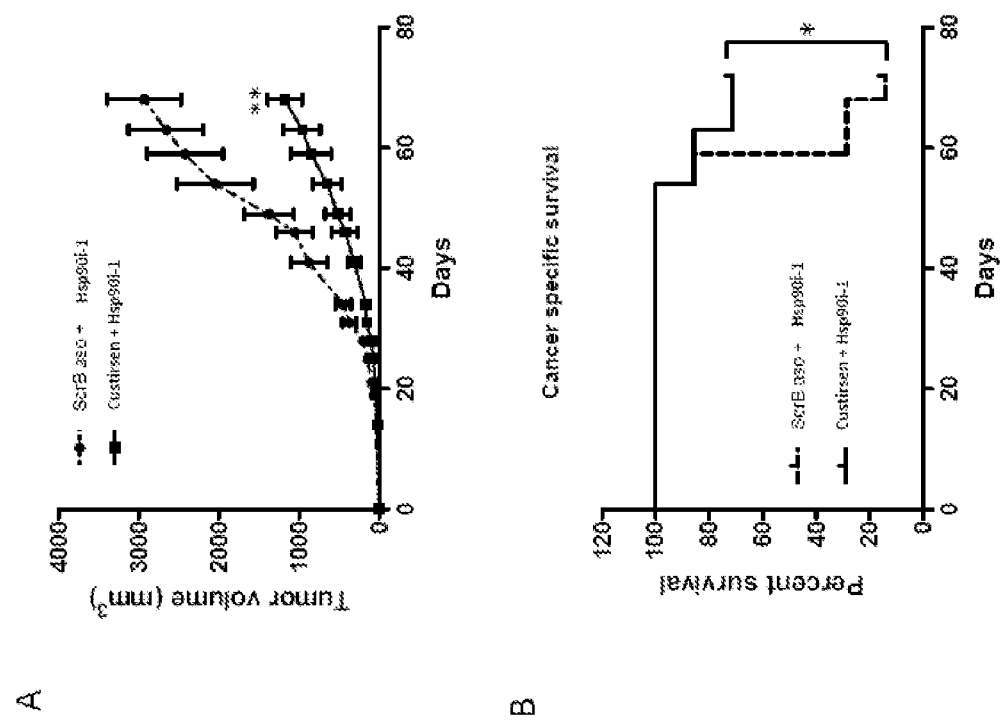
FIG. 5. Increased potency of custirsen+Hsp90i-1 combination in PC-3 xenograft model. Mice were treated IP with 25 mg/kg Hsp90i-1 and 15 mg/kg custirsen starting when tumors reached 300 mm as described in Example 6. A, The mean tumor volume of mice custirsen+Hsp90i-1 was compared with control ScrB ASO+Hsp90i-1±SEM (n=7). **, p<0.01. B, in Kaplan-Meier curve, cancer-specific survival was compared between mice treated with custirsen+Hsp90i-1 and control ScrB ASO+Hsp90i-1 over a 72-d period. *, p<0.05. C, tumors were collected after 72-d and CLU, Ki67 and TUNEL were evaluated by immunohistochemical analysis (original magnification: ×200).
Figure 5:
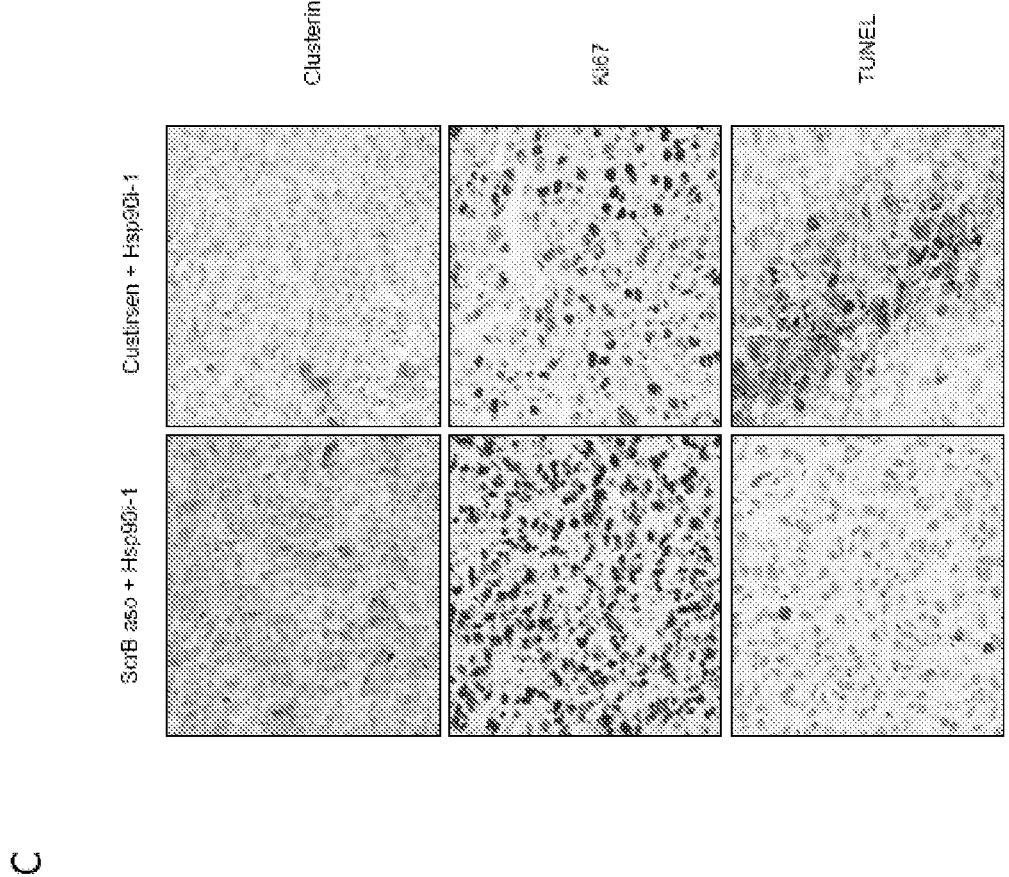

The effects of combining custirsen with Hsp90i-1 was evaluated in PC-3 tumors in vivo. Male nude mice bearing PC-3 xenografts were randomly selected for treatment (custirsen+Hsp90i-1 vs control ScrB+Hsp90i-1; n=7). Custirsen+Hsp90i-1 had significantly enhanced the antitumor effects compared to of ScrB+Hsp90i-1 in vivo, reducing the mean tumor volume from 2935.3 mm$^3$ to 1176.9 mm$^3$ after 68 days (**; $p\leq0.01$), compared to control ScrB (FIG. 5A). Cancer specific survival was significantly prolonged with combined custirsen+Hsp90i-1 compared with controls (71.4% vs 14.3% at day 72, respectively; *; $p\leq0.05$; FIG. 5B. Immunohistochemical analysis reveals decreased CLU, Ki67, and Akt, expression after treatment with custirsen+Hsp90i-1 compared to other groups (FIG. 5C). Additionally, custirsen+Hsp90i-1 treated tumors had higher apoptosis as shown by increased TUNEL staining compared with other groups (FIG. 5C).

Example 5

Figure 6:
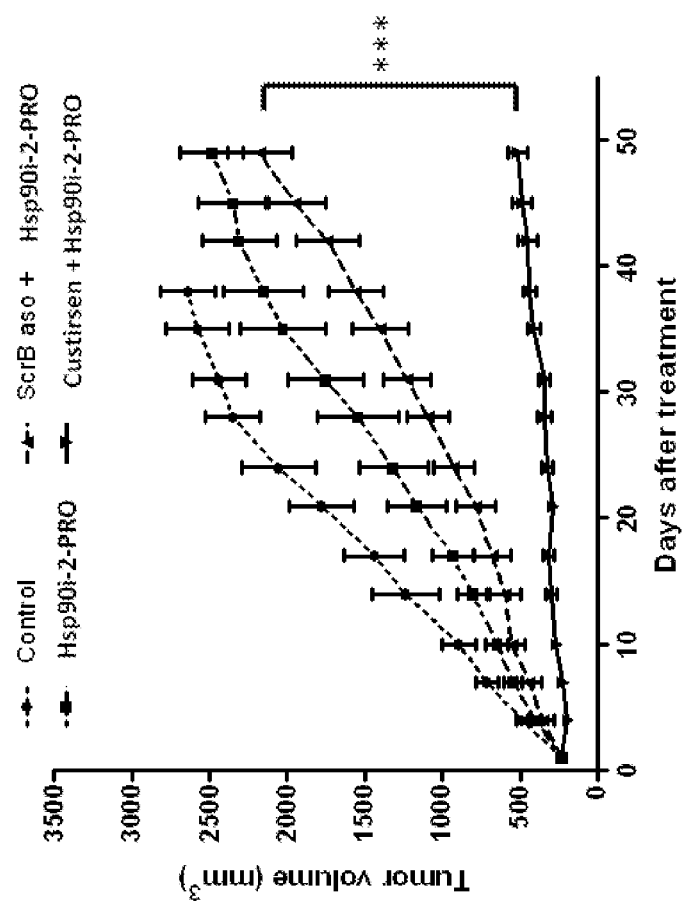
FIG. 6. Increased potency of custirsen+Hsp90i-2-PRO combination in LNCaP xenograft model. Mice were treated with 25 mg/kg Hsp90i-2-PRO and 15 mg/kg custirsen starting when serum PSA values relapsed to pre-castration levels. The mean tumor volume (A) and the serum PSA level (B) were compared between the 4 groups±SEM (n=10). ***, p<0.001. C, PSA doubling time and velocity were calculated as described in Example 6. *, p<0.05. D, in Kaplan-Meier curve, cancer-specific survival was compared between the 4 groups over a 62-d period. ***, p<0.001. Progression-free survival was defined as time for the first tumor volume doubling.
Figure 6:
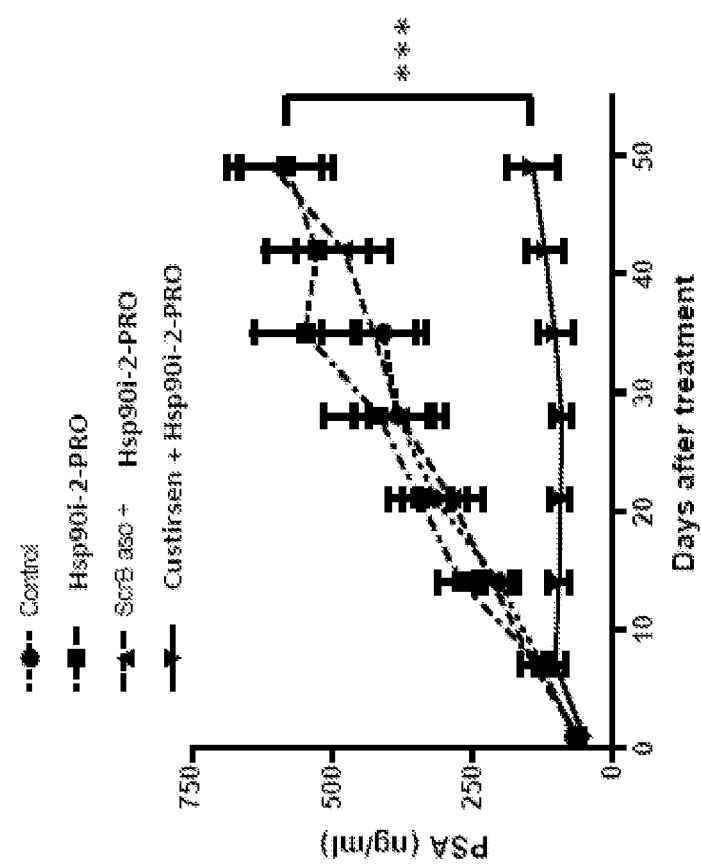
Figure 6:
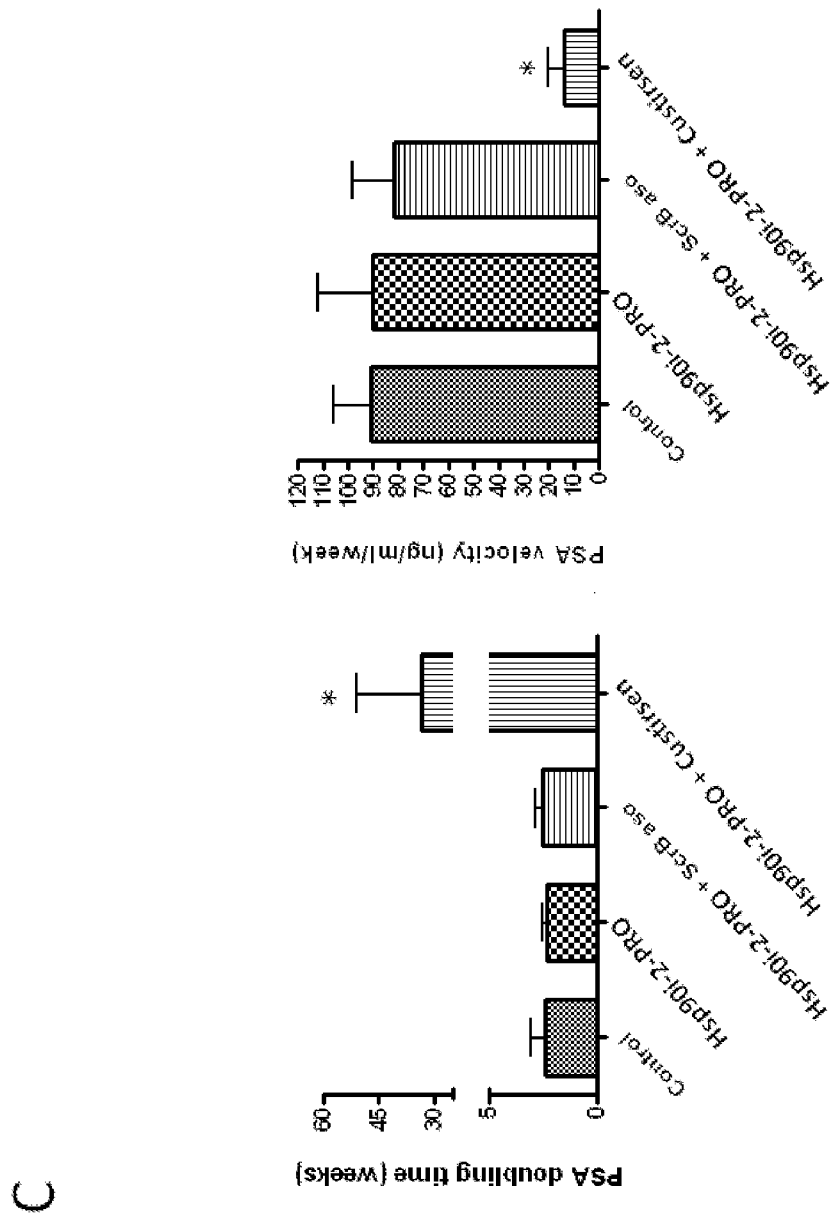
Figure 6:
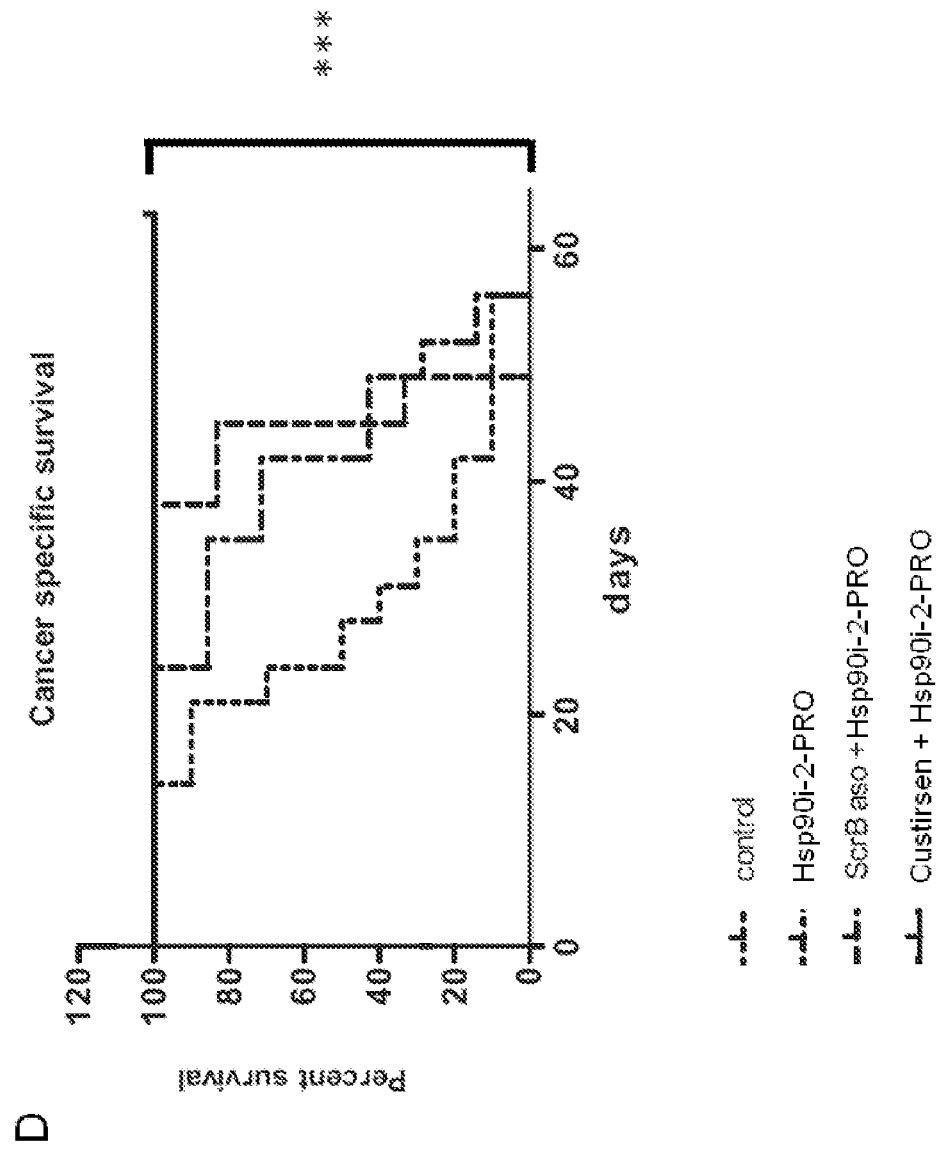

Potent Combination Therapy of Custirsen and Hsp90i-2-PRO in LNCaP CRPC Xenografts In Vivo Next the effects of combined treatment with custirsen and Hsp90i-2-PRO was assessed in castrate resistant LNCaP tumors. Mice bearing LNCaP tumors were castrated when PSA values exceeded 50 ng/ml. Once PSA levels relapsed above pre-castration levels mice were randomly assigned to vehicle control, Hsp90i-2-PRO alone, Hsp90i-2-PRO+control ScrB, or Hsp90i-2-PRO+custirsen (n=10 in each group). Mice treated with Hsp90i-2-PRO+custirsen had significant delays in tumor growth compared with all other groups (FIG. 6A) (at 10 days, respectively 265.3 mm$^3$, and 892.7 mm$^3$ for control, 646.4 mm$^3$ for Hsp90i-2-PRO alone and 551.56 mm$^3$ for Hsp90i-2-PRO+control ScrB). By 7 weeks post treatment, all mice in the control had been euthanized; tumor volume in the Hsp90i-2-PRO+custirsen group was r517.4 mm$^3$ compared to 2483.6 mm3 for HSP90i-2-PRO alone and 2176.4 mm$^3$ for Hsp90i-2-PRO+control ScrB; ***, p<0.001; FIG. 6A).

Serum PSA levels were also significantly lower (~4-fold) in the mice receiving custirsen+Hsp90i-2-PRO compared with other groups (***, p<0.001; FIG. 6B). The combination custirsen+Hsp90i-2-PRO group had a mean PSA level of 120 ng/ml after 42 days compared to 418.7 ng/ml in vehicle group, 527 ng/ml in Hsp90i-2-PRO alone, or 480.3 ng/ml in scrB+Hsp90i-2-PRO groups. The combination custirsen+Hsp90i-2-PRO group had a significantly increased PSA doubling time (33.6 weeks; *, p<0.05) and decreased PSA velocity (13.78 ng/mL/week; *, p<0.05) compared with other groups (PSA doubling time: ~2.4 weeks; velocity: ~85 ng/mL/week; FIG. 6C).

Overall survival was also significantly longer in mice treated with combined custirsen+Hsp90i-2-PRO (FIG. 6D). By day 57, all mice died or were euthanized due to high tumor burden in control, Hsp90i-2-PRO alone, or control ScrB+Hsp90i-2-PRO groups compared with the combined custirsen+Hsp90i-2-PRO group, where all mice were still alive (p<0.001) after 62 days. These data demonstrate that targeting CLU using custirsen in combination with HSP90i-2-PRO inhibits tumor growth and prolongs survival in human CRPC xenograft model significantly more than monotherapy.

Figure 7:
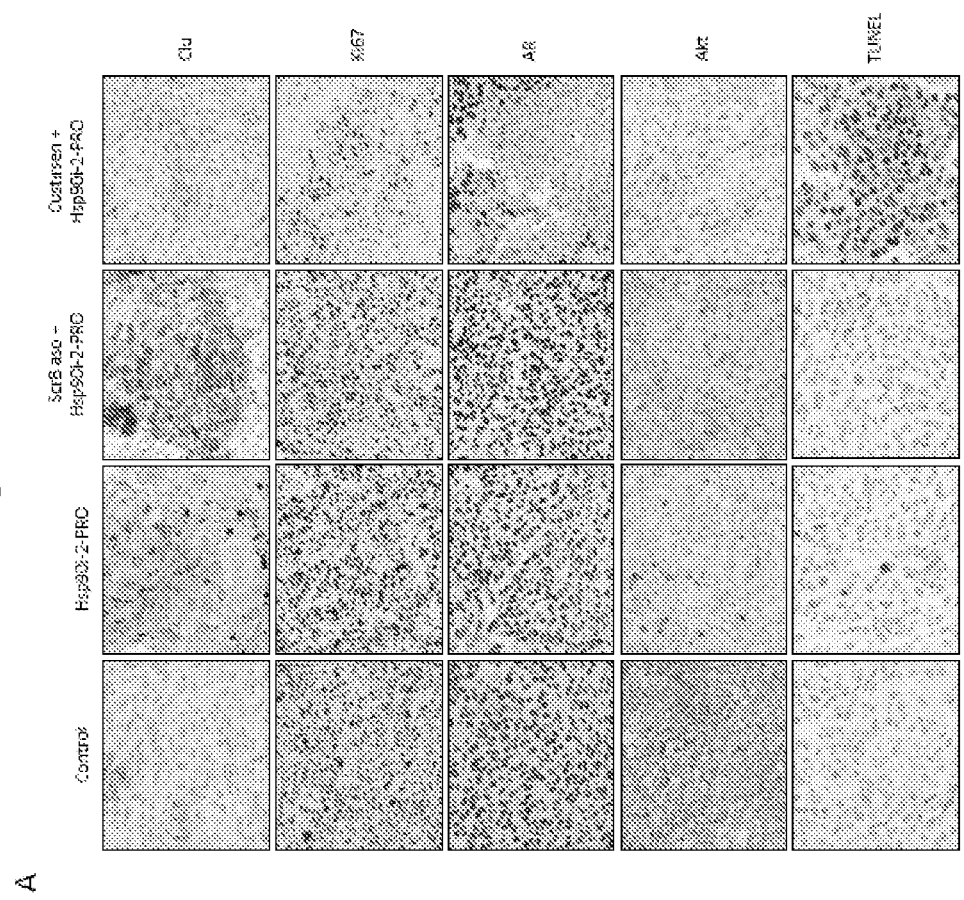
FIG. 7. Increased potency of custirsen+Hsp90i-2-PRO combination treatment apoptosis levels in CRPC LNCaP tumors. A, tumors were collected after 57 days and CLU, Ki67, AR, AKT and TUNEL were evaluated by immunohistochemical analysis (original magnification: ×200). B, total proteins were extracted from the xenograft tumors and CLU, AR, Akt and PSA were analyzed by western blotting. The relative levels were normalized with vinculin and estimated in densitometric units±SEM.
Figure 7B:
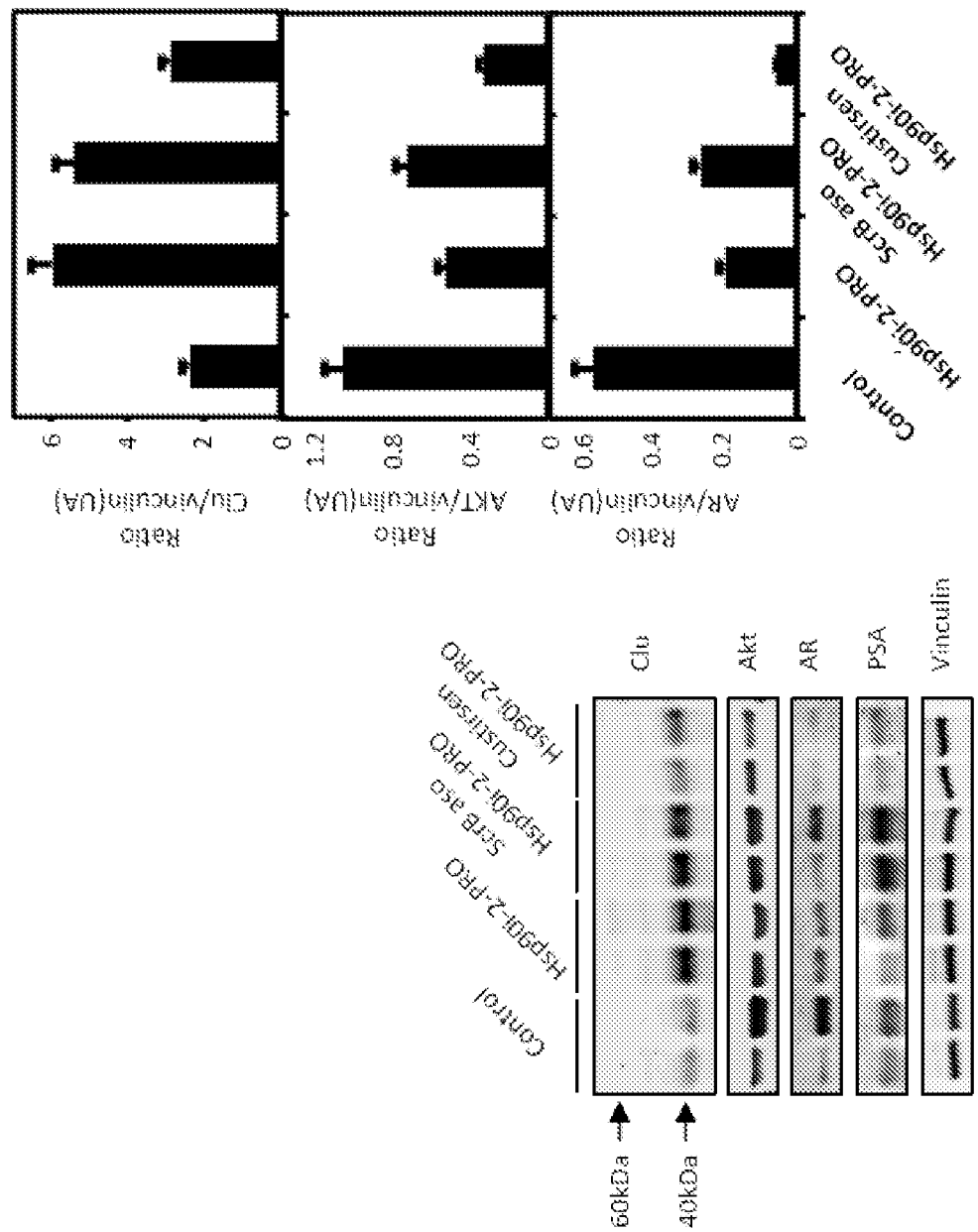

Consistent with in vitro findings, immunohistochemical analysis revealed decreased CLU, Ki67, Akt, and AR expression after treatment with combined custirsen+Hsp90i-2-PRO compared with other groups (FIG. 7A). The immunostaining results were corroborated by western blotting (FIG. 7B). Additionally, tumors treated with combination custirsen+Hsp90i-2-PRO had higher apoptosis rates compared with other groups as shown by increased TUNEL staining (FIG. 7A). These data suggest that decreases in tumor progression custirsen+Hsp90i-2-PRO treated tumors result from both reduced proliferation rates as well as increased apoptosis rates.

Example 6

Materials and Methods for Examples 1-5

Tumor Cell Lines and Reagents:

The human PCa cell line PC-3 was purchased from the American Type Culture Collection (2008, ATCC-authentication by isoenzymes analysis) and maintained in DMEM (Invitrogen-Life Technologies, Inc.) supplemented with 5% fetal bovine serum and 2 mmol/L Lglutamine. LNCaP cells were kindly provided by Dr. Leland W. K. Chung (1992, MDACC, Houston Tx) and tested and authenticated by whole-genome and whole-transcriptome sequencing on Illumina Genome Analyzer IIx platform in July 2009. LNCaP cells were maintained RPMI 1640 (Invitrogen Life Technologies, Inc.) supplemented with 5% fetal bovine serum and 2 mmol/L L-glutamine. All cell lines were cultured in a humidified 5% $CO_2$/air atmosphere at 37° C. All cell lines were passaged for less than 3 months after resurrection. Western blotting and/or real time PCR was performed for AR and PSA each time when LNCaP cells were resurrected.
Therapeutic Agents:

Hsp90 inhibitor, HSP90i-2 (4-(6,6-Dimethyl-4-oxo-3-trifluoromethyl-4,5,6,7-tetrahydro-indazol-1-yl)-2-(4-hydroxy-cyclohexylamino)-benzamide) and its prodrug HSP90i-2-PRO were used respectively for in vitro and in vivo studies. These compounds are novel synthetic small molecular weight inhibitors that bind the N-terminal adenosine triphosphate binding site of Hsp90 and HSP90i-2-PRO is orally bioavailable. For the in vitro studies, HSP90i-2 was dissolved in dimethyl sulfoxide (DMSO) at 10 mM stock solutions and stored at −20° C. For the in vivo studies, HSP90i-2-PRO was dissolved in PBS 1% carboxymethylcellulose and 0.5% Tween 80 (Invitrogen-Life Technologies, Inc.) at 15 mg/ml and stored at 4° C.

HSP90i-1 (17-allylamino-17-demethoxygeldanamycin (17-AAG)) was used for in vitro and in vivo studies. For the studies, 17-AAG was dissolved in dimethyl sulfoxide (DMSO) at 10 mM stock solutions and stored at −20° C.
Clusterin siRNA and Antisense Oligonucleotides siRNAs were purchased from Dharmacon Research, Inc. (Lafayette, Colo.) using the siRNA sequence corresponding to the human CLU initiation site in exon 2 and a scramble control as previously described (Sowery et al., 2008). Second-generation antisense (custirsen) and scrambled (ScrB) oligonucleotides with a 2'-O-(2-methoxy)ethyl modification were supplied by OncoGenex Pharmaceuticals (Vancouver, British Columbia, Canada). Custirsen sequence (5'-CAGCAGCAGAGTCTTCATCAT-3'), SEQ ID NO:3 corresponds to the initiation site in exon II of human CLU. The ScrB control sequence was 5'-CAGCGCTGACAACAGTTTCAT-3' (SEQ ID NO: 44). Prostate cells were treated with siRNA or oligonucleotides using protocols described previously (Sowery et al., 2008).
Cell Proliferation and Apoptosis Assays:

Prostate cells lines were plated in appropriate media (DMEM or RPMI) with 5% FBS and treated with Hsp90i-2-PRO or Hsp90i-1 at indicated concentration and time and cell growth was measured using the crystal violet assay as described previously (Leung et al., 2000). Detection and quantitation of apoptotic cells were done by flow-cytometry (described below) and western blotting analysis. Each assay was repeated in triplicate.

The combination index (CI) was evaluated using CalcuSyn dose effect analysis software (Biosoft, Cambridge, UK). This method, based on the multiple drug effect equation of Chou-Talalay (Chou et al., 1984), is suitable for calculating combined drug activity over a wide range of growth inhibition: CI=1, additivity; CI>1, antagonism; CI<1, combination effect. CI was calculated at $ED_{50}$ and $ED_{75}$.

Caspase-3 activity was assessed 3 days after treatment using the kit CaspACE Assay System, Fluorometric (Promega, Madison, Wis., USA). Fifty µg of total cell lysate were incubated with caspase-3 substrate AC-DEVD-AMC at room temperature for 4 h and caspase-3 activity was quantified in a fluorometer with excitation at 360 nm and emission 460 nm.
Cell Cycle Analysis:

Prostate cancer cell lines were incubated in the absence or the presence of 1 µM Hsp90i-2 or Hsp90i-1 for 72 h, trypsinized, washed twice and incubated in PBS containing 0.12% Triton X-100, 0.12 mM EDTA and 100 µg/ml ribonuclease A; 50 µg/ml propidium iodide was then added to each sample for 20 min at 4° C. Cell cycle distribution was analyzed by flow cytometry (Beckman Coulter Epics Elite, Beckman, Inc., Miami, Fla.), based on 2N and 4N DNA content. Each assay was done in triplicate.
Western Blotting Analysis:

Samples containing equal amounts of protein (depending on the antibody, 5-50 µg) from lysates of cultured tumor prostate cell lines underwent electrophoresis on SDS-polyacrylamide gel and were transferred to nitrocellulose filters. The filters were blocked in Odyssey Blocking Buffer (LI-COR Biosciences) at room temperature for 1 h and blots were probed overnight at 4° C. with primary antibodies to detect proteins of interests. After incubation, the filters were washed 3 times with washing buffer (PBS containing 0.1% Tween) for 5 min. Filters were then incubated for 1 h with 1:5,000 diluted Alexa Fluor secondary antibodies (Invitrogen) at room temperature. Specific proteins were detected using ODYSSEY IR imaging system (LI-COR Biosciences) after washing.
Quantitative Reverse Transcription-PCR:

Total RNA was extracted from cultured cells after 48 h of treatment using TRIzol reagent (Invitrogen Life Technologies, Inc.). Two µg of total RNA was reversed transcribed using the Transcriptor First Strand cDNA Synthesis Kit (Roche Applied Science). Real-time monitoring of PCR amplification of complementary DNA (cDNA) was performed using DNA primers (supplemental table S1) on ABI PRISM 7900 HT Sequence Detection System (applied Biosystems) with SYBR PCR Master Mix (Applied Biosystems). Target gene expression was normalized to GAPDH levels in respective samples as an internal standard, and the comparative cycle threshold (Ct) method was used to calculated relative quantification of target mRNAs. Each assay was performed in triplicate.
Luciferase Assay:

LNCaP and C4-2 cells ($2.5 \times 10^5$) were plated on six-plates and transfected using lipofectin (6 µL per well; Invitrogen Life Technologies, Inc.). The total amount HSE plasmids DNA used were normalized to 1 µg per well by the addition of a control plasmid. One µM HSP90i-2 or Hsp90i-1 was added 4 h after the transfection and for 48 h. HSE-luciferase activity was measured using Dual-Luciferase Reporter Assay System (Promega) with the aid of a microplate luminometer (EG&G Berthold). All experiments were carried out in triplicate wells and repeated 3 times using different preparations of plasmids.

Immunofluorescence:

Tumor cells were grown on coverslips and treated with different concentration of Hsp90i-2 or Hsp90i-1 for 48 h. After treatment, cells were fixed in ice-cold methanol completed with 3% acetone for 10 min at −20° C. Cells were the washed thrice with PBS and incubated with 0.2% Triton/PBS for 10 min, followed by washing and 30 min blocking in 3% nonfat milk before the addition of antibody overnight to detect HSF-1 (1:250). Antigens were visualized using anti-mouse antibody coupled with FITC (1:500; 30 min). Photomicrographs were taken at 20× magnification using Zeiss Axioplan II fluorescence microscope, followed by analysis with imaging software (Northern Eclipse, Empix Imaging, Inc.).

Animal Treatment:

Male athymic nude mice (Harlan Sprague-Dawley, Inc.) were injected s.c. with $2 \times 10^6$ LNCaP cells (suspended in 0.1 mL Matrigel; BD Biosciences). The mice were castrated once tumors reach between 300 and 500 $mm^3$ or the PSA level increased above 50 ng/mL. Once tumors progressed to castrate resistance, mice were randomly assigned to vehicle, Hsp90i-2-PRO alone, Hsp90i-2-PRO+ScrB ASO or Hsp90i-2-PRO+custirsen. Hsp90i-2-PRO (Prodrug, 25 mg/kg; formulation in 0.5% CMC+0.5% Tween-80) is orally administered three times per week and custirsen or ScrB ASO (15 mg/kg) was injected intra-peritoneally once daily for the first week and then three times per week. Each experimental group consisted of 10 mice. Tumor volume was measured twice weekly (length×width×depth×0.5432). Serum PSA was determined weekly by enzymatic immunoassay (Abbott IMX, Montreal, Quebec, Canada). PSA doubling time (PSAdt) and velocity were calculated by the log-slope method (PSAt=PSAinitial×emt). Data points were expressed as average tumor volume±SEM or average PSA concentration±SEM.

To establish PC-3 tumors, $2 \times 10^6$ PC-3 cells were inoculated s.c. in the flank region of 6-8 week-old male athymic mice (Harlan Sprague-Dawley, Inc.). When tumors reached $100^{-3}$, usually 3-4 weeks after injection, mice were randomly selected for treatment with Hsp90i-1 (25 mg/kg)+ control ScrB ASO (15 mg/kg) or Hsp90i-1+custirsen (15 mg/kg). Hsp90i-1 was injected i.p. three times per week, and custirsen or ScrB were injected i.p. once/day for the first week and then three times per week. For each experimental group consisted of 7 mice. Tumor volume was measured twice weekly. Data points were expressed as average tumor volume±SEM.

When tumor volume reached 10% of body weight, mice were sacrificed and tumors harvested for evaluation of protein expression by western blotting analyses and immunohistochemistry. All animal procedures were performed according to the guidelines of the Canadian Council on Animal Care and appropriate institutional certification.

Immunohistochemistry:

Immunohistochemical stains were performed on formalin-fixed and paraffin-embedded 4 μm sections of tumor samples using adequate primary antibody, and the Ventana autostainer Discover XT (Ventana Medical System) with enzyme labeled biotin streptavidin system and solvent resistant 3,3'-diaminobenyidine Map kit. All comparisons of staining intensities were made at 200× magnifications.

Statistical Analysis:

All in vitro data were assessed using the Student t test and Mann-Whitney test. Tumor volumes of mice were compared using Kruskal-Wallis test. Overall survival was analyzed using Kaplan-Meier curves and statistical significance between the groups was assessed with the log-rank test (Graphpad Prism). Levels of statistical significance were set at $P < 0.05$.

Antibodies used for western blotting:

PARP (1/1000) Caspase 3 (1/1000), Akt (1/1000), p-Akt (1/500), are from cell signaling. Cyclin D1 (1/1000), HSP90 (1/1000), HSP70 (1/1000), clusterin (1/1000), AR (1/1000), PSA (1/1000) HSF-1 (1/1000) are from Santa Cruz. HSP27 (1/5000) is from Assays Designs.

TABLE 3

Primers used for quantitative real-time PCT

| Sequence name | Sequence 5' to 3' forward | Sequence 5' to 3' reverse |
|---|---|---|
| Clusterin | GAGCAGCTGAACGAGCAGTTT (SEQ ID NO: 45) | CTTCGCCTTGCGTGAGGT (SEQ ID NO: 46) |
| Hsp70 | TGCCCTATCCAGATCCTGCTA (SEQ ID NO: 47) | GAGCCATCAGACTGAGGAGTGA (SEQ ID NO: 48) |
| Hsp90 | TTCAGGCCCTTCCCGAAT (SEQ ID NO: 49) | TCACTCCTTCCTTGGCAACAT (SEQ ID NO: 50) |

Discussion

Prostate cancer responds initially to anti-androgen therapies, however, progression of castration resistant disease frequently occurs. Small molecule inhibitors of Hsp90 show promise in the treatment of castration-resistant prostate cancer (CRPC) and other cancers, however these inhibitors trigger a heat shock response that attenuates drug effectiveness. In prostate cancer, treatment resistance emerges early due to compensatory mechanisms involving activation of heat shock factor 1 (HSF-1). Once released from Hsp90, HSF-1 translocates to the nucleus, binds to heat shock elements (HSE) of Hsp genes and increases Hsp transcription activity (Whitesell et al., 2005). Therefore, Hsp90 inhibition induces a heat shock response with increased expression of several Hsps including Hsp90, Hsp70, Hsp27 and clusterin (CLU), which enhance tumor cell survival and treatment resistance. The up-regulation of these molecular chaperones has been reported to play a role in cellular recovery from stress by restoring protein homeostasis, promoting thermotolerance, cell survival, and treatment resistance (Takayama et al., 2003; Zoubeidi et al., 2010). The data herein show that preventing CLU induction in this response would enhance Hsp90 inhibitor-induced CRPC cell death in vitro and in vivo. As disclosed herein, CRPC was treated with Hsp90 inhibitor HSP90i-2-PRO or HSP90i-1 in the absence or presence of custirsen, an antisense drug that targets CLU. Treatment with either Hsp90 inhibitor alone increased nuclear translocation and transcriptional activity of the heat shock factor HSF-1, which stimulated dose- and time-dependent increases in heat shock protein expression, including especially CLU expression. Treatment-induced increases in CLU were blocked by custirsen, such that the combination of custirsen and either Hsp90 inhibitor had enhanced inhibition activity on CRPC cell growth and apoptosis compared to custirsen or Hsp90 inhibitor monotherapy. Accompanying these effects was a decrease in HSF-1 transcriptional activity as well as expression of HSPs, Akt, PSA and androgen receptor. In vivo evaluation of the Hsp90 inhibitors with custirsen in xenograft models of human CRPC demonstrated that custirsen markedly potentiated anti-tumor efficacy, leading to an 80% inhibition of tumor growth with prolonged survival compared to Hsp90 inhibitor monotherapy. Together, the findings herein indicate that Hsp90 inhibitor-induced activation of the heat shock response and CLU is attenuated by custirsen, with combination therapy having increased potency on delaying CRPC progression.

Development of treatment resistance is a common feature of most malignancies and the underlying basis for most cancer deaths. Treatment resistance evolves, in part, from selective pressures of treatment that collectively increase the apoptotic rheostat of cancer cells. Survival proteins up-regulated after treatment stress include anti-apoptotic members of the bcl-2 protein family, survivin, and molecular chaperones like CLU and other HSPs (Zellweger et al. 2003).

Molecular chaperones help cells cope with stress-induced protein aggregation, and play prominent roles in cell signaling and transcriptional regulatory networks. Chaperones act as genetic buffers stabilizing the phenotype of various cells and organisms at times of environmental stress, and enhance Darwinian fitness of cells during cancer progression and treatment resistance (Whitesell et al., 2005). Heat shock chaperones are key components of the heat shock response, a highly conserved stress-activated protective mechanism also associated with oncogenic transformation and thermo-tolerance (Dai et al., 2007). Chaperones are particularly important in regulating misfolded protein and endoplasmic reticular (ER) stress responses, an emerging area of interest in treatment stress and resistance. A growing enthusiasm for therapeutic modulation of this proteostasis network highlights Hsp's and CLU as rational targets because of their multifunctional roles in signaling and transcriptional networks associated with cancer progression and treatment resistance. Cancer cells express higher levels of molecular chaperones and pirate the protective functions of HSF1 to support their transformation (Dai et al., 2007). Indeed, inhibitors of Hsp90, Hsp70, Hsp27 or CLU have all been reported to induce cancer cell death and sensitize chemotherapy (Lamoureux et al., 2011; Guo et al., 2005).

Increased expression of clusterin (CLU) has been associated with chemoresistance, radioresistance, and hormone resistance (Zellweger et al., 2003; July et al., 2004). CLU is a stress-induced cytoprotective chaperone that inhibits protein aggregation in a manner analogous to small HSPs, and its promoter contains a 14-bp element recognized by the transcription factor HSF-1 (Humphreys et al., 1999). In human PCa, CLU levels are low in Gleason grade 3 untreated hormone-naive tissues, but increase with higher Gleason score (Steinberg et al., 1997) and within weeks after androgen deprivation (July et al., 2002). CLU expression correlates with loss of the tumor suppressor gene NRx3.1 during the initial stages of prostate tumorigenesis in NRx3.1 knockout mice (Song et al., 2009). Experimental and clinical studies associate CLU with development of treatment resistance, where CLU suppresses treatment-induced cell death in response to androgen withdrawal, chemotherapy or radiation (Miyake et al., 2000a; July et al., 2002; Miyake et al., 2000b; Miyake et al., 2000c). Over-expression of CLU in human prostate LNCaP cells accelerates progression after hormone- or chemo-therapy (Miyake et al., 2000a; Miyake et al., 2000c), identifying CLU as an anti-apoptotic gene up-regulated by treatment stress that confers therapeutic resistance. Custirsen is a second-generation phosphorothioate antisense oligonucleotide currently in late stage clinical development that potently inhibits CLU expression and enhances the efficacy of anticancer therapies in various human cancers including PCa (Zoubeidi et al., 2010, Gleave et al., 2005). While targeting CLU enhances the cytotoxic effects of chemotherapy and delays tumor growth in various human cancers including PCa (Miyake et al., 2005), a role for CLU has not been characterized in the context of Hsp90 inhibitor treatment and resistance. As shown herein, Hsp90 inhibition induces a heat shock response with increased HSF-1 activity and CLU expression, which functions to inhibit treatment-induced apoptosis and enhance emergence of treatment resistance. Knockdown of CLU using custirsen potentiates the effect of Hsp90 inhibitors in CRPC.

Aspects of the present invention relate to the unexpected discovery that an oligonucleotide targeting clusterin expression such as custirsen, together with a Hsp90 inhibitor is a potent combination for treatment of prostate cancer. The discovery that an ant-clusterin therapy combined with Hsp90 is so potent is particularly surprising because Hsp90 is known to increase the expression of multiple cytoprotective proteins.

Several Hsp90 inhibitors including HSP90i-2 have potent anti-tumor activity in various preclinical models (Lamoureux et al., 2001; Chandarlapaty et al., 2008; Okawa et al., 2009) and are in clinical trials (Lamoureux et al., 2011; Sydor et al., 2006). Consistent with prior reports (Lamoureux et al., 2011; Cervantes-Gomez et al., 2009), the data herein show that Hsp90 inhibitors induce a stress response with activation of the transcription factor HSF-1 and subsequent increased levels of Hsp90 itself, Hsp70 and CLU. This heat shock response likely enhance emergence of treatment resistance, as inhibition of transcription using Actinomycin D attenuates HSP90i-1-mediated Hsp70 and Hsp27 expression and potentiates the effect of HSP90i-1 in vitro (Cervantes-Gomez et al., 2009). Additionally, inhibition of the stress response by silencing HSF-1 also increases the activity of Hsp90 inhibitors (Bagatell et al., 2000). The experiments disclosed herein evaluated the role of CLU in this heat shock response since CLU is dramatically induced by Hsp90 inhibitor treatment and CLU inhibitors are in late stage clinical development.

CLU is associated with many varied patho-physiological processes including reproduction, lipid transport, complement regulation and apoptosis (Zoubeidi et al. 2010; Rosenberg et al., 1995). CLU expression is rapidly upregulated in various tissues undergoing apoptosis, including normal and malignant prostate and breast tissues following hormone withdrawal (Kyprianou et al., 1990; Kyprianou et al., 1991). Previous studies have also linked CLU expression with induction and progression of many cancers, including CRPC (Zoubeidi et al., 2010). Furthermore, CLU up-regulation following androgen ablation in xenograft tumor models accelerates progression to castrate resistance and renders cells resistant to other apoptotic stimuli, including taxane chemotherapy (Miyake et al., 2000; Miyake et al., 2001). Consistent with these accumulated findings (Miyake et al., 2001), inhibition of CLU using custirsen synergistically enhances conventional as well as molecular targeted therapies in PCa preclinical models (Sowery et al., 2008). Indeed, custirsen is now in Phase III trials as Phase II studies reported >90% inhibition of CLU in human prostate cancer tissues (Chi et al., 2005), and 7 months prolonged survival when OGX-011 is combined with docetaxel in CRPC (Chi et al., 2008; Chi et al., 2010).

The data herein show that Hsp90 inhibitors increase CLU levels both in vitro and in vivo, while clusterin inhibits HSP90i-2 or HSP90i-1 induced CLU. As expected (Cervantes-Gomez et al., 2009; Bagatell et al., 2000), HSP90i-2 or HSP90i-1 induces HSF-1 transcriptional activity leading to up-regulation of HSPs expression. Surprisingly, the experiments described herein found that CLU silencing abrogates, while CLU overexpression enhances, Hsp90 inhibitor-induced HSF-1 transcription activity, identifying a role for CLU in the regulation of HSF-1 and the heat shock response itself. CLU knockdown blocks the translocation to HSF-1 to the nucleus following treatment with Hsp90 inhibitors. This effect of CLU on HSF-1 activity is biologically relevant since CLU overexpression protects, while CLU silencing enhances, cytotoxicity of Hsp90 inhibitors. Consistent with these in vitro results, synergistic effects were also observed in vivo in PC-3 and LNCaP models when custirsen was combined with Hsp90 inhibitors. Combination custirsen plus Hsp90 inhibitor significantly delay CRPC tumor growth and prolonged survival in PC-3 and LNCaP models. Increased apoptotic rates with combined Hsp90 and CLU inhibition suggests that delayed tumor progression resulted from enhanced treatment-induced apoptosis. Systemic administration of an oligonucleotide which reduces clusterin expression plus a Hsp90 inhibitor decreases tumor growth compared with control ScrB ASO plus an Hsp90 inhibitor in PC-3 model and LNCaP castration-resistant prostate cancer, respectively. This inhibition of tumor progression is accompanied with a prolongation of survival in both prostate cancer models. Detection of increased apoptosis after combined clusterin plus Hsp90 inhibition by detection of TUNEL using immunohistochemistry suggests that delayed tumor progression after combined therapy results from enhanced Hsp90 inhibitor-induced apoptosis. Collectively, these results highlight, for the first time, a biologically relevant feed-forward regulation loop of CLU on HSF-1 and the heat shock response.

The effect of an oligonucleotide which reduces clusterin expression in combination with an Hsp90 inhibitor on PSA level was examined in the LNCaP castration-resistant prostate cancer model as disclosed herein above. As shown herein, targeting CLU using siRNA or the antisense drug, custirsen, suppressed treatment-induced CLU induction and enhanced Hsp90 inhibitor-induced cell death in prostate cancer cells. Serum PSA level is an established and useful biomarker regulated by androgen receptor (AR) in the presence of androgens (Magklara et al., 2002), and a valuable tool in the follow-up of patients to assess the efficacy of chemotherapy. In addition to the effects of CLU inhibition on the heat shock response, observations in the castrate-sensitive, AR-positive LNCaP model highlight another possible benefit of combined CLU and Hsp90 suppression involving AR activity. Hsp90 inhibition is known to destabilize and degrade the AR with decreased PSA expression (Solit et al., 2002; Georget et al., 2002). In vivo, serum PSA levels as well as PSA doubling time and velocity, were significantly reduced with combination OGX-011 therapy compared with PF-04929113 monotherapy. Serum PSA level is an established and useful AR-regulated biomarker (Kim et al., 2004) and a valuable tool in assessing efficacy of chemotherapy. Interestingly, at the low doses of Hsp90 inhibitor used in this in vivo study, no effect on serum PSA level was apparent. Lower PSA levels with combination therapy correlated with lower AR levels. This correlation between CLU inhibition and lower AR levels may involve the regulation loop of CLU on HSF-1 and the role of HSF-1 in regulating expression of other AR chaperones (eg. Hsp27, Hsp70, Hsp90, FKBP5.2) and we are actively exploring the molecular basis in ongoing experiments. While CLU is known to be transcriptionally activated by HSF-1 (Zoubeidi et al., 2010), the data herein also show that CLU exerts a feed forward loop that in turn activates HSF-1. CLU knockdown decreases HSF-1 transcriptional activity and abrogates its nuclear translocation, which subsequently leads to decreased Hsp27, Hsp70 and Hsp90 expression, similar to that observed after HSF-1 knockdown (Rossi et al., 2006). Consequently, AR stability is reduced because of lowered chaperone levels.

In addition to increased potency of anti-tumor activity, combination therapy may also allow dose reduction strategies to reduce toxicity. For example, HSP90i-1 induced hepatotoxicity as monotherapy at 60 mg/kg/day (Glaze et al., 2005), while HSP90i-2-PRO caused body weight loss at 50 mg/kg/day. In a previous study, 50 mg/kg HSP90i-2-PRO as monotherapy inhibited LNCaP CRPC tumor progression (Lamoureux et al., 2011). At sub-therapeutic doses of 25 mg/kg/day used in the present study, HSP90i-2-PRO monotherapy showed marginal, non-significant decreases in tumor volume and no effect on serum PSA levels; however, significant delays in tumor progression were seen at this lower dose when HSP90i-2-PRO was combined with custirsen, with no toxicity observed.

The data disclosed herein help define how stress induced by Hsp90 inhibitors regulates CLU by induction of HSF-1 activity and, in turn, how CLU regulates HSF-1 activity, cell survival, and treatment resistance. As demonstrated herein, for the first time, that CLU inhibition abrogates the heat shock response induced Hsp90 inhibitors. These observations are clinically relevant since CLU inhibitors are in phase III clinical trials, and provide a framework for building new drug combinations based on mechanism-based interventions to overcome drug resistance. The present invention relates to the development of targeted strategies employing custirsen in combination with Hsp90 inhibitors to improve patient outcome in CRPC.

References

Bagatell R, Paine-Murrieta G D, Taylor C W, Pulcini E J, Akinaga S, Benjamin I J, et al. Induction of a heat shock factor 1-dependent stress response alters the cytotoxic activity of hsp90-binding agents. Clin Cancer Res. 2000; 6:3312-8.

Banerji U., de Bono J., Judson I., Kaye S., Workman P., Biomarkers in early clinical trials: the committed and the skeptics. Clin Cancer Res 2008, 14, 2512; author reply 2513-2514.

Carthew, R. W., Gene silencing by double-stranded RNA. Current Opinion in Cell Biology; 2001, 13:244-248;

Cervantes-Gomez F, Nimmanapalli R, Gandhi V. Transcription inhibition of heat shock proteins: a strategy for combination of 17-allylamino-17-demethoxygeldanamycin and actinomycin d. Cancer Res. 2009; 69:3947-54.

Chandarlapaty S, Sawai A, Ye Q, Scott A, Silinski M, Huang K, et al. SNX2112, a synthetic heat shock protein 90 inhibitor, has potent antitumor activity against HER kinasedependent cancers. Clin Cancer Res. 2008; 14:240-8.

Chi K N, Siu L L, Hirte H, Hotte S J, Knox J, Kollmansberger C, et al. A phase I study of OGX-011, a 2'-methoxyethyl phosphorothioate antisense to clusterin, in combination with docetaxel in patients with advanced cancer. Clin Cancer Res. 2008; 14:833-9.

Chi K N, Hotte S J, Yu E Y, Tu D, Eigl B J, Tannock I, et al. Randomized phase II study of docetaxel and prednisone with or without OGX-011 in patients with metastatic castrationresistant prostate cancer. J Clin Oncol. 2010; 28:4247-54.

Chi et al., A Phase I Pharmacokinetic and Pharmacodynamic Study of custirsen, a 2'-Methoxyethyl antisense Oligonucleotide to Clusterin, in Patients with Localized Prostate Cancer. Journal of the National Cancer Institute; 2005, 97(17)1287-1296;

Chi et al., A phase I pharmacokinetic (PK) and pharmacodynamic (PD) study of custirsen, a 2' methoxyethyl phosphorothioate antisense to clusterin, in patients with prostate cancer prior to radical prostatectomy. Journal of Clinical Oncology; 2004 ASCO Annual Meeting Proceedings, vol. 22, no. 14S:3033;

Chiosis G., Huezo H., Rosen N., Mimnaugh E., Whitesell L., Neckers L., 17AAG: low target binding affinity and potent cell activity—finding an explanation. Mol Cancer Ther 2003, 2, 123-129.

Chou T C, Talalay P. Quantitative analysis of dose-effect relationships: the combined effects of multiple drugs or enzyme inhibitors. Adv Enzyme Regul. 1984; 22:27-55.

Culig Z. Androgen receptor cross-talk with cell signalling pathways. Growth Factors. 2004; 22:179-84.

Dai C., Whitesell L., Rogers A. B., Lindquist S., Heat shock factor 1 is a powerful multifaceted modifier of carcinogenesis. Cell 2007, 130, 1005-1018.

Eccles S. A., Massey A., Raynaud F. I. et al., NVP-AUY922: a novel heat shock protein 90 inhibitor active against xenograft tumor growth, angiogenesis, and metastasis. Cancer Res 2008, 68, 2850-2860.

Egorin et al., Metabolism of 17-(Allyamino)-17-dementhoxygeldanamycin (NSC 330507) by Murine and Human Hepatic Preparations. Cancer Research, 1998, 58:2385-2396.

Elbashir et al., Duplexes of 21-nucleotide RNAs mediate RNA interference in cultured mammalian cells. Nature; 2001, 411:494-498;

Fire et al., Potent and specific genetic interference by double-stranded RNA in *Caenorhabditis elegans*. Nature; 1998, 391:806-11;

Georget V., Terouanne B., Nicolas J. C., Sultan C., Mechanism of antiandrogen action: key role of hsp90 in conformational change and transcriptional activity of the androgen receptor. Biochemistry 2002, 41, 11824-11831.

Glaze E. R., Lambert A. L., Smith A. C. et al., Preclinical toxicity of a geldanamycin analog, 17-(dimethylaminoethylamino)-17-demethoxygeldanamycin (17-DMAG), in rats and dogs: potential clinical relevance. Cancer Chemother Pharmacol 2005, 56, 637-647.

Gleave M., Chi K. N., Knock-down of the cytoprotective gene, clusterin, to enhance hormone and chemosensitivity in prostate and other cancers. Ann N Y Acad Sci 2005, 1058, 1-15.

Gleave M. E., Monia B. P., Antisense therapy for cancer. Nat Rev Cancer 2005, 5, 468-479.

Gleave M E, Bruchovsky N, Moore M J, Venner P. Prostate cancer: 9. Treatment of advanced disease. CMAJ. 1999; 160:225-32. Gleave M, Tolcher A, Miyake H, Nelson C, Brown B, Beraldi E, et al. Progression to androgen independence is delayed by adjuvant treatment with antisense Bcl-2 oligodeoxynucleotides after castration in the LNCaP prostate tumor model. Clin Cancer Res. 1999; 5:2891-8.

Guo F., Rocha K., Bali P. et al., Abrogation of heat shock protein 70 induction as a strategy to increase antileukemia activity of heat shock protein 90 inhibitor 17-allylaminodemethoxy geldanamycin. Cancer Res 2005, 65, 10536-10544.

Huang et al., Discovery of Novel 2-Aminobenzamine Inhibitors of Heat Shock Protein 90 as Potent, Selective and Orally Active Antitumor Agents. J. Med Chem 2009, 52:4288-4305.

Humphreys D T, Carver J A, Easterbrook-Smith SB, Wilson MR. Clusterin has chaperone-like activity similar to that of small heat shock proteins. J Biol. Chem. 1999; 274: 6875-81.

Jemal A, Siegel R, Ward E, Murray T, Xu J, Smigal C, et al. Cancer statistics, 2006. CA Cancer J. Clin. 2006; 56:106-30.

July L. V., Beraldi E., So A. et al., Nucleotide-based therapies targeting clusterin chemosensitize human lung adenocarcinoma cells both in vitro and in vivo. Mol Cancer Ther 2004, 3, 223-232.

July L V, Akbari M, Zellweger T, Jones E C, Goldenberg S L, Gleave M E. Clusterin expression is significantly enhanced in prostate cancer cells following androgen withdrawal therapy. Prostate. 2002; 50:179-88.

Kamal A., Thao L., Sensintaffar J. et al., A high-affinity conformation of Hsp90 confers tumour selectivity on Hsp90 inhibitors. Nature 2003, 425, 407-410.

Kim J, Coetzee G A. Prostate specific antigen gene regulation by androgen receptor. J Cell Biochem. 2004; 93:233-41.

Knudsen K E, Scher H I. Starving the addiction: new opportunities for durable suppression of AR signaling in prostate cancer. Clin Cancer Res. 2009; 15:4792-8.

Koga et al., Inhibition of Cancer Invasion and Metastasis by Targeting the Molecular Chaperone Heat-shock Protein 90. Anticancer Research 29:797-808.

Krajewska et al., Immunohistochemical analysis of bcl-2, bax, bcl-X, and mcl-1 expression in prostate cancers. Am. J. Pathol; 1996, 148:1567-1576;

Kyprianou N, English H F, Isaacs J T. Programmed cell death during regression of PC-82 human prostate cancer following androgen ablation. Cancer Res. 1990; 50:3748-53.

Kyprianou N, English H F, Davidson N E, Isaacs J T. Programmed cell death during regression of the MCF-7 human breast cancer following estrogen ablation. Cancer Res. 1991; 51:162-6.

Lamoureux F., Thomas C., Yin M. et al., A novel HSP90 inhibitor delays castrate resistant prostate cancer without altering serum PSA levels and inhibits osteoclastogenesis. Clin Cancer Res 2011; 17, 2301-13.

Lassi et al., Update on castrate-resistant prostate cancer: 2010. Current Opinion in Oncology; 2010, 22:263-267;

Leung S. Y., Jackson J., Miyake H., Burt H., Gleave M. E., Polymeric micellar paclitaxel phosphorylates Bcl-2 and induces apoptotic regression of androgen-independent LNCaP prostate tumors. Prostate 2000, 44, 156-163.

Magklara A., Brown T. J., Diamandis E. P., Characterization of androgen receptor and nuclear receptor co-regulator expression in human breast cancer cell lines exhibiting differential regulation of kallikreins 2 and 3. Int J Cancer 2002, 100, 507-514.

McDonnell et al., Expression of the proto-oncogene bcl-2 in the prostate and its association with the emergence of androgen-independent prostate cancer. Cancer Res; 1992, 52:6940-6944; Miyaki et al., Antisense oligodeoxynucleotide therapy targeting clusterin gene for prostate cancer: Vancouver experience from discovery to clinic. International Journal of Urology; 2005, 12: 785-794;

Miyake H, Nelson C, Rennie P S, Gleave M E. Overexpression of insulin-like growth factor binding protein-5 helps accelerate progression to androgen-independence in the human prostate LNCaP tumor model through activation of phosphatidylinositol 3'-kinase pathway. Endocrinology. 2000; 141:2257-65.

Miyake H, Nelson C, Rennie P S, Gleave M E. Testosterone-repressed prostate message-2 is an antiapoptotic gene involved in progression to androgen independence in prostate cancer. Cancer Res. 2000a; 60:170-6.

Miyake H, Tolcher A, Gleave M E. Antisense Bcl-2 oligodeoxynucleotides inhibit progression to androgen-independence after castration in the Shionogi tumor model. Cancer Res. 1999; 59:4030-4.

Miyake H, Hara S, Zellweger T, Kamidono S, Gleave M E, Hara I. Acquisition of resistance to Fas-mediated apoptosis by overexpression of clusterin in human renal-cell carcinoma cells. Mol. Urol. 2001; 5:105-11.

Miyake H, Nelson C, Rennie P S, Gleave M E. Acquisition of chemoresistant phenotype by overexpression of the antiapoptotic gene testosterone-repressed prostate message-2 in prostate cancer xenograft models. Cancer Res. 2000b; 60:2547-54.

Miyake H, Chi K N, Gleave M E. Antisense TRPM-2 oligodeoxynucleotides chemosensitize human androgen-independent PC-3 prostate cancer cells both in vitro and in vivo. Clin Cancer Res. 2000c; 6:1655-63.

Miyaki et al., Antisense oligodeoxynucleotide therapy targeting clusterin gene for prostate cancer: Vancouver experience from discovery to clinic. International Journal of Urology; 2005, 12: 785-794;

Oh et al., Management of hormone refractory prostate cancer: current standards and future prospects. J Urol; 1998, 160(4):1220-9;

Okawa Y, Hideshima T, Steed P, Vallet S, Hall S, Huang K, et al. SNX-2112, a selective Hsp90 inhibitor, potently inhibits tumor cell growth, angiogenesis, and osteoclastogenesis in multiple myeloma and other hematologic tumors by abrogating signaling via Akt and ERK. Blood. 2009; 113:846-55.

Raffo et al., Overexpression of bcl-2 protects prostate cancer cells from apoptosis in vitro and confers resistance to androgen depletion in vivo. Cancer Res; 1995 55(19): 4448-4445;

Rocchi P, So A, Kojima S, Signaevsky M, Beraldi E, Fazli L, et al. Heat shock protein 27 increases after androgen ablation and plays a cytoprotective role in hormone-refractory prostate cancer. Cancer Res. 2004; 64:6595-602.

Rosenberg M E, Silkensen J. Clusterin: physiologic and pathophysiologic considerations. Int J Biochem Cell Biol. 1995; 27:633-45.

Rossi A., Clafre S., Balsamo M., Pierimarchi P., Santoro M. G., Targeting the heat shock factor 1 by RNA interference: a potent tool to enhance hyperthermochemotherapy efficacy in cervical cancer. Cancer Res 2006, 66, 7678-7685.

Scher et al., Antitumour activity of AR1 in castration-resistant prostate cancer: a phase 1-2 study. The Lancet; 2010, 375(9724): 1437-1446;

Sensibar et al., Prevention of Cell Death Induced by Tumor Necrosis Factor α in LNCaP Cells by Overexpression of Sulfated Glycoprotein-2 (Clusterin). Cancer Research; 1995, 55: 2431-2437;

Solit D. B., Basso A. D., Olshen A. B., Scher H. I., Rosen N., Inhibition of heat shock protein 90 function down-regulates Akt kinase and sensitizes tumors to Taxol. Cancer Res 2003, 63, 2139-2144.

Solit D. B., Zheng F. F., Drobnjak M. et al., 17-Allylamino-17-demethoxygeldanamycin induces the degradation of androgen receptor and HER-2/neu and inhibits the growth of prostate cancer xenografts. Clin Cancer Res 2002, 8, 986-993.

Song H, Zhang B, Watson M A, Humphrey P A, Lim H, Milbrandt J. Loss of NRx3.1 leads to the activation of discrete downstream target genes during prostate tumorigenesis. Oncogene. 2009; 28:3307-19.

Sowery R D, Hadaschik B A, So A I, Zoubeidi A, Fazli L, Hurtado-Coll A, et al. Clusterin knockdown using the antisense oligonucleotide OGX-011 re-sensitizes docetaxelrefractory prostate cancer PC-3 cells to chemotherapy. BJU Int. 2008; 102:389-97.

Steinberg J, Oyasu R, Lang S, Sintich S, Rademaker A, Lee C, et al. Intracellular levels of SGP-2 (Clusterin) correlate with tumor grade in prostate cancer. Clin Cancer Res. 1997; 3:1707-11.

Sydor J R, Normant E, Pien C S, Porter J R, Ge J, Grenier L, et al. Development of 17-allylamino-17-demethoxy-geldanamycin hydroquinone hydrochloride (IPI-504), an anticancer agent directed against Hsp90. Proc Natl Acad Sci USA. 2006; 103:17408-13.

Takayama S., Reed J. C., Homma S., Heat-shock proteins as regulators of apoptosis. Oncogene 2003, 22, 9041-9047.

Tran et al. Development of a Second-Generation Antiandrogen for Treatment of Advanced Prostate Cancer. Science; 2009, 324(5928): 787-790;

Whitesell L., Lindquist S. L., HSP90 and the chaperoning of cancer. Nat Rev Cancer 2005, 5, 761-772.

Wong et al., Molecular characterization of human TRPM-2/clusterin, a gene associated with sperm maturation, apoptosis and neurodegeneration. Eur. J. Biochem. 1994, 221 (3):917-925;

Workman P., Burrows F., Neckers L., Rosen N., Drugging the cancer chaperone HSP90: combinatorial therapeutic exploitation of oncogene addiction and tumor stress. Ann N Y Acad Sci 2007, 1113, 202-216.

Yagoda et al., Cytotoxic chemotherapy for advanced hormone-resistant prostate cancer. Cancer; 1993, 71 (Supp. 3): 10981109;

Young J. C., Hartl F. U., Polypeptide release by Hsp90 involves ATP hydrolysis and is enhanced by the co-chaperone p 23. EMBO J. 2000, 19, 5930-5940.

Zellweger T., Kiyama S., Chi K. et al., Overexpression of the cytoprotective protein clusterin decreases radiosensitivity in the human LNCaP prostate tumour model. BJU Int 2003, 92, 463-469.

Zoubeidi A., Chi K., Gleave M., Targeting the cytoprotective chaperone, clusterin, for treatment of advanced cancer. Clin Cancer Res 2010, 16, 1088-1093.

What is claimed is:

1. A method for treating a mammalian subject affected by prostate cancer comprising administering to the mammalian subject i) an oligonucleotide which reduces clusterin expression and ii) a Heat Shock Protein 90 (Hsp90) inhibitor, wherein the oligonucleotide is an antisense or RNAi oligonucleotide that is complementary to the sequence of clusterin of the mammalian subject, and that reduces clusterin expression; and the heat shock protein 90 (Hsp90) inhibitor is 4-(6,6-Dimethyl-4-oxo-3-trifluoromethyl-4,5,6,7-tetrahydro-indazol-1-yl)-2-(4-hydroxy-cyclohexylamino)-benzamide, or a pharmaceutically acceptable salt thereof, or a prodrug that is metabolized to release 4-(6,6-Dimethyl-4-oxo-3-trifluoromethyl-4,5,6,7-tetrahydro-indazol-1-yl)-2-(4-hydroxy-cyclohexylamino)-benzamide following administration, each in an amount that when administered to a mammalian subject in combination with the other is effective to treat prostate cancer in the mammalian subject.

2. The method of claim 1, wherein the oligonucleotide is an antisense oligonucleotide.

3. The method of claim 2, wherein the antisense oligonucleotide comprises one of SEQ ID NOs. 3, 4, and 11.

4. The method of claim 3, wherein the antisense oligonucleotide comprises SEQ ID NO: 3.

5. The method of claim 4, wherein the antisense oligonucleotide is modified to enhance in vivo stability relative to an unmodified oligonucleotide of the same sequence.

6. The method of claim 5, wherein the oligonucleotide is custirsen.

7. The method of claim 6, wherein the Hsp90 inhibitor comprises Hsp90i-2-PRO.

8. The method of claim 1, wherein the Hsp90 inhibitor comprises Hsp90i-2-PRO.

9. The method of claim 1, wherein the mammalian subject is human.

10. The method of claim 9, wherein the oligonucleotide is an antisense oligonucleotide.

11. The method of claim 10, wherein the antisense oligonucleotide comprises one of SEQ ID NOs: 3, 4 or 11.

12. The method of claim 11, wherein the antisense oligonucleotide comprises SEQ ID NO: 3.

13. The method of claim 12, wherein the antisense oligonucleotide is modified to enhance in vivo stability relative to an unmodified oligonucleotide of the same sequence.

14. The method of claim 13, wherein the oligonucleotide is custirsen.

15. The method of claim 14, wherein the Hsp90 inhibitor comprises Hsp90i-2-PRO.

* * * * *

SEQUENCE LISTING

<160> NUMBER OF SEQ ID NOS: 50

<210> SEQ ID NO 1
<211> LENGTH: 21
<212> TYPE: DNA
<213> ORGANISM: Homo sapiens

<400> SEQUENCE: 1
gcacagcagg agaatcttca t                                              21

<210> SEQ ID NO 2
<211> LENGTH: 21
<212> TYPE: DNA
<213> ORGANISM: Homo sapiens

<400> SEQUENCE: 2
tggagtcttt gcacgcctcg g                                              21

<210> SEQ ID NO 3
<211> LENGTH: 21
<212> TYPE: DNA
<213> ORGANISM: Homo sapiens

<400> SEQUENCE: 3
cagcagcaga gtcttcatca t                                              21

<210> SEQ ID NO 4
<211> LENGTH: 21
<212> TYPE: DNA
<213> ORGANISM: Homo sapiens

<400> SEQUENCE: 4
attgtctgag accgtctggt c                                              21

<210> SEQ ID NO 5
<211> LENGTH: 21
<212> TYPE: DNA
<213> ORGANISM: Homo sapiens

<400> SEQUENCE: 5
ccttcagctt tgtctctgat t                                              21

<210> SEQ ID NO 6
<211> LENGTH: 21
<212> TYPE: DNA
<213> ORGANISM: Homo sapiens

<400> SEQUENCE: 6
agcagggagt cgatgcggtc a                                              21

<210> SEQ ID NO 7
<211> LENGTH: 21
<212> TYPE: DNA
<213> ORGANISM: Homo sapiens

<400> SEQUENCE: 7
atcaagctgc ggacgatgcg g                                              21

<210> SEQ ID NO 8
<211> LENGTH: 21
<212> TYPE: DNA
<213> ORGANISM: Homo sapiens

<400> SEQUENCE: 8

-continued gcaggcagcc cgtggagttg t                           21

<210> SEQ ID NO 9
<211> LENGTH: 21
<212> TYPE: DNA
<213> ORGANISM: Homo sapiens

<400> SEQUENCE: 9
ttcagctgct ccagcaagga g                           21

<210> SEQ ID NO 10
<211> LENGTH: 21
<212> TYPE: DNA
<213> ORGANISM: Homo sapiens

<400> SEQUENCE: 10
aatttagggt tcttcctgga g                           21

<210> SEQ ID NO 11
<211> LENGTH: 21
<212> TYPE: DNA
<213> ORGANISM: Homo sapiens

<400> SEQUENCE: 11
gctgggcgga gttgggggcc t                           21

<210> SEQ ID NO 12
<211> LENGTH: 17
<212> TYPE: DNA
<213> ORGANISM: Homo sapiens

<400> SEQUENCE: 12
ggtgtagacg ccgcacg                                17

<210> SEQ ID NO 13
<211> LENGTH: 16
<212> TYPE: DNA
<213> ORGANISM: Homo sapiens

<400> SEQUENCE: 13
gcagcgcagc ccctgg                                 16

<210> SEQ ID NO 14
<211> LENGTH: 22
<212> TYPE: DNA
<213> ORGANISM: Homo sapiens

<400> SEQUENCE: 14
gcagcagccg cagcccggct cc                          22

<210> SEQ ID NO 15
<211> LENGTH: 18
<212> TYPE: DNA
<213> ORGANISM: Homo sapiens

<400> SEQUENCE: 15
agccgcagcc cggctcct                               18

<210> SEQ ID NO 16
<211> LENGTH: 20
<212> TYPE: DNA
<213> ORGANISM: Homo sapiens

```
<400> SEQUENCE: 16
cagcagccgc agcccggctc                                               20

<210> SEQ ID NO 17
<211> LENGTH: 20
<212> TYPE: DNA
<213> ORGANISM: Homo sapiens

<400> SEQUENCE: 17
cagcagccgc agcccggctc                                               20

<210> SEQ ID NO 18
<211> LENGTH: 20
<212> TYPE: DNA
<213> ORGANISM: Homo sapiens

<400> SEQUENCE: 18
agcagccgca gcccggctcc                                               20

<210> SEQ ID NO 19
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 19
ccagagcucg cccuucuact t                                             21

<210> SEQ ID NO 20
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 20
guagaagggc gagcucuggt t                                             21

<210> SEQ ID NO 21
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 21
gaugcucaac accuccucct t                                             21

<210> SEQ ID NO 22
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 22
ggaggaggug uugagcauct t                                             21

<210> SEQ ID NO 23
<211> LENGTH: 19
```

<212> TYPE: DNA
<213> ORGANISM: Artificial
<220> FEATURE:
<223> OTHER INFORMATION: RNAi for human clusterin, the sequence is
      synthesized

<400> SEQUENCE: 23
uaauucaaca aaacugutt                                                      19

<210> SEQ ID NO 24
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 24
gacaguuuua uugaauuagt t                                                   21

<210> SEQ ID NO 25
<211> LENGTH: 19
<212> TYPE: DNA
<213> ORGANISM: Artificial
<220> FEATURE:
<223> OTHER INFORMATION: RNAi for human clusterin, the sequence is
      synthesized

<400> SEQUENCE: 25
uaauucaaca aaacugutt                                                      19

<210> SEQ ID NO 26
<211> LENGTH: 19
<212> TYPE: DNA
<213> ORGANISM: Artificial
<220> FEATURE:
<223> OTHER INFORMATION: RNAi for human clusterin, the sequence is
      synthesized

<400> SEQUENCE: 26
acaguuuugu ugaauuatt                                                      19

<210> SEQ ID NO 27
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 27
augaugaaga cucugcugct t                                                   21

<210> SEQ ID NO 28
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 28
gcagcagagu cuucaucaut t                                                   21

<210> SEQ ID NO 29
<211> LENGTH: 22
<212> TYPE: DNA

```
<213> ORGANISM: Artificial
<220> FEATURE:
<223> OTHER INFORMATION: RNAi for human clusterin, the sequence is
      synthesized

<400> SEQUENCE: 29
ugaaugaagg gacuaaccug tt                                              22

<210> SEQ ID NO 30
<211> LENGTH: 22
<212> TYPE: DNA
<213> ORGANISM: Artificial
<220> FEATURE:
<223> OTHER INFORMATION: RNAi for human clusterin, the sequence is
      synthesized

<400> SEQUENCE: 30
cagguuaguc ccuucauuca tt                                              22

<210> SEQ ID NO 31
<211> LENGTH: 22
<212> TYPE: DNA
<213> ORGANISM: Artificial
<220> FEATURE:
<223> OTHER INFORMATION: RNAi for human clusterin, the sequence is
      synthesized

<400> SEQUENCE: 31
cagaaauaga caaagugggg tt                                              22

<210> SEQ ID NO 32
<211> LENGTH: 22
<212> TYPE: DNA
<213> ORGANISM: Artificial
<220> FEATURE:
<223> OTHER INFORMATION: RNAi for human clusterin, the sequence is
      synthesized

<400> SEQUENCE: 32
ccccacuuug ucuauuucug tt                                              22

<210> SEQ ID NO 33
<211> LENGTH: 22
<212> TYPE: DNA
<213> ORGANISM: Artificial
<220> FEATURE:
<223> OTHER INFORMATION: RNAi for human clusterin, the sequence is
      synthesized

<400> SEQUENCE: 33
acagagacua agggaccaga tt                                              22

<210> SEQ ID NO 34
<211> LENGTH: 22
<212> TYPE: DNA
<213> ORGANISM: Artificial
<220> FEATURE:
<223> OTHER INFORMATION: RNAi for human clusterin, the sequence is
      synthesized

<400> SEQUENCE: 34
acagagacua agggaccaga tt                                              22

<210> SEQ ID NO 35
<211> LENGTH: 21
<212> TYPE: DNA
<213> ORGANISM: Artificial
```

```
<220> FEATURE:
<223> OTHER INFORMATION: RNAi for human clusterin, the sequence is
      synthesized

<400> SEQUENCE: 35
ccagagcucg cccuucuact t                                              21

<210> SEQ ID NO 36
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 36
guagaagggc gagcucuggt t                                              21

<210> SEQ ID NO 37
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 37
gucccgcauc guccgcagct t                                              21

<210> SEQ ID NO 38
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 38
gcugcggacg augcgggact t                                              21

<210> SEQ ID NO 39
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 39
cuaauucaau aaaacuguct t                                              21

<210> SEQ ID NO 40
<211> LENGTH: 21
<212> TYPE: DNA
<213> ORGANISM: Artificial
<220> FEATURE:
<223> OTHER INFORMATION: RNAi for human clusterin, the sequence is
      synthesized

<400> SEQUENCE: 40
gacaguuuua uugaauuagt t                                              21

<210> SEQ ID NO 41
<211> LENGTH: 19
<212> TYPE: DNA
<213> ORGANISM: Artificial
<220> FEATURE:
```

<223> OTHER INFORMATION: RNAi for human clusterin, the sequence is
      synthesized

<400> SEQUENCE: 41
augaugaaga cucugcugc                                                    19

<210> SEQ ID NO 42
<211> LENGTH: 19
<212> TYPE: DNA
<213> ORGANISM: Artificial
<220> FEATURE:
<223> OTHER INFORMATION: RNAi for human clusterin, the sequence is
      synthesized

<400> SEQUENCE: 42
gcagcagagu cuucaucau                                                    19

<210> SEQ ID NO 43
<211> LENGTH: 2877
<212> TYPE: DNA
<213> ORGANISM: Homo sapiens

<400> SEQUENCE: 43
gctttccgcg gcattctttg ggcgtgagtc atgcaggttt gcagccagcc ccaaaggggg         60
tgtgtgcgcg agcagagcgc tataaatacg gcgcctccca gtgcccacaa cgcggcgtcg        120
ccaggaggag cgcgcgggca cagggtgccg ctgaccgagg cgtgcaaaga ctccagaatt        180
ggaggcatga tgaagactct gctgctgttt gtgggctgc tgctgacctg ggagagtggg        240
caggtcctgg gggaccagac ggtctcagac aatgagctcc aggaaatgtc caatcaggga        300
agtaagtacg tcaataagga aattcaaaat gctgtcaacg gggtgaaaca gataaagact        360
ctcatagaaa aaacaaacga gagcgcaag acactgctca gcaacctaga agaagccaag        420
aagaagaaag aggatgccct aaatgagacc agggaatcag agacaaagct gaaggagctc        480
ccaggagtgt gcaatgagac catgatggcc ctctgggaag agtgtaagcc ctgcctgaaa        540
cagacctgca tgaagttcta cgcacgcgtc tgcagaagtg gctcaggcct ggttggccgc        600
cagcttgagg agttcctgaa ccagagctcg cccttctact ctggatgaa tggtgaccgc        660 atcgactccc tgctggagaa cgaccggcag cagacgcaca tgctggatgt catgcaggac        720
cacttcagcc gcgcgtccag catcatagac gagctcttcc aggacaggtt cttcacccgg        780
gagccccagg atacctacca ctacctgccc ttcagcctgc ccaccggag gcctcacttc        840 ttctttccca gtcccgcat cgtccgcagc ttgatgccct tctctccgta cgagcccctg        900
aacttccacg ccatgttcca gcccttcctt gagatgatac acgaggctca gcaggccatg        960
gacatccact ccatagcccc ggccttccag cacccgccaa cagaattcat acgagaaggc       1020
gacgatgacc ggactgtgtg ccgggagatc cgccacaact ccacgggctg cctgcggatg       1080
aaggaccagt gtgacaagtg ccgggagatc ttgtctgtgg actgttccac caacaaccccc       1140 tcccaggcta agctgcggcg ggagctcgac gaatccctcc aggtcgctga gaggttgacc       1200
aggaaataca acgagctgct aaagtcctac cagtggaaga tgctcaacac ctcctccttg       1260
ctggagcagc tgaacgagca gtttaactgg gtgtcccggc tggcaaacct cacgcaaggc       1320
gaagaccagt actatctgcg ggtcaccacg gtggcttccc acacttctga ctcggacgtt       1380
ccttccggtg tcactgaggt ggtcgtgaag ctctttgact ctgatccat cactgtgacg       1440 gtccctgtag aagtctccag gaagaaccct aaatttatgg agaccgtggc ggagaaagcg       1500
ctgcaggaat accgcaaaaa gcaccgggag gagtgagatg tggatgttgc ttttgcacct       1560

```
acgggggcat ctgagtccag ctcccccaa gatgagctgc agcccccag agagagctct    1620 gcacgtcacc aagtaaccag gccccagcct ccaggccccc aactccgccc agcctctccc    1680
cgctctggat cctgcactct aacactcgac tctgctgctc atgggaagaa cagaattgct    1740
cctgcatgca actaattcaa taaaactgtc ttgtgagctg atcgcttgga gggtcctctt    1800
tttatgttga gttgctgctt cccggcatgc cttcattttg ctatgggggg caggcagggg    1860
ggatggaaaa taagtagaaa caaaaaagca gtggctaaga tggtataggg actgtcatac    1920
cagtgaagaa taaagggtg aagaataaaa gggatatgat gacaaggttg atccacttca    1980
agaattgctt gctttcagga agagagatgt gtttcaacaa gccaactaaa atatattgct    2040
gcaaatggaa gcttttctgt tctattataa aactgtcgat gtattctgac caaggtgcga    2100
caatctccta aaggaataca ctgaaagtta aggagaagaa tcagtaagtg taaggtgtac    2160
ttggtattat aatgcataat tgatgttttc gttatgaaaa catttggtgc ccagaagtcc    2220
aaattatcag ttttatttgt aagagctatt gcttttgcag cggttttatt tgtaaaagct    2280
gttgatttcg agttgtaaga gctcagcatc ccaggggcat cttcttgact gtggcatttc    2340
ctgtccaccg ccggtttata tgatcttcat acctttccct ggaccacagg cgtttctcgg    2400
cttttagtct gaaccatagc tgggctgcag taccctacgc tgccagcagg tggccatgac    2460
tacccgtggt accaatctca gtcttaaagc tcaggctttt cgttcattaa cattctctga    2520
tagaattctg gtcatcagat gtactgcaat ggaacaaaac tcatctggct gcatcccagg    2580
tgtgtagcaa agtccacatg taaatttata gcttagaata ttcttaagtc actgtccctt    2640
gtctctcttt gaagttataa acaacaaact taaagcttag cttatgtcca aggtaagtat    2700
tttagcatgg ctgtcaagga aattcagagt aaagtcagtg tgattcactt aatgatatac    2760
attaattaga attatggggt cagaggtatt tgcttaagtg atcataattg taaagtatat    2820
gtcacattgt cacattaatg tcacactgtt tcaaaagtta aaaaaaaaaa aaaaaaa     2877
```

<210> SEQ ID NO 44
<211> LENGTH: 21
<212> TYPE: DNA
<213> ORGANISM: Artificial
<220> FEATURE:
<223> OTHER INFORMATION: Control antisense oligonucleotide sequence,
      the sequence is synthesized

<400> SEQUENCE: 44
cagcgctgac aacagtttca t                                             21

<210> SEQ ID NO 45
<211> LENGTH: 21
<212> TYPE: DNA
<213> ORGANISM: Artificial
<220> FEATURE:
<223> OTHER INFORMATION: Forward primer sequence for clusterin, the
      sequence is synthesized

<400> SEQUENCE: 45
gagcagctga acgagcagtt t                                             21

<210> SEQ ID NO 46
<211> LENGTH: 18
<212> TYPE: DNA
<213> ORGANISM: Artificial
<220> FEATURE:
<223> OTHER INFORMATION: Reverse primer sequence for clusterin, the
      sequence is synthesized

```
<400> SEQUENCE: 46
cttcgccttg cgtgaggt                                                    18

<210> SEQ ID NO 47
<211> LENGTH: 21
<212> TYPE: DNA
<213> ORGANISM: Artificial
<220> FEATURE:
<223> OTHER INFORMATION: Forward primer for Hsp70, the sequence is
      synthesized

<400> SEQUENCE: 47
tgccctatcc agatcctgct a                                                21

<210> SEQ ID NO 48
<211> LENGTH: 22
<212> TYPE: DNA
<213> ORGANISM: Artificial
<220> FEATURE:
<223> OTHER INFORMATION: Reverse primer sequence for Hsp70, the sequence
      is synthesized

<400> SEQUENCE: 48
gagccatcag actgaggagt ga                                               22

<210> SEQ ID NO 49
<211> LENGTH: 18
<212> TYPE: DNA
<213> ORGANISM: Artificial
<220> FEATURE:
<223> OTHER INFORMATION: Forward primer for Hsp90, the sequence is
      synthesized

<400> SEQUENCE: 49
ttcaggccct tcccgaat                                                    18

<210> SEQ ID NO 50
<211> LENGTH: 21
<212> TYPE: DNA
<213> ORGANISM: Artificial
<220> FEATURE:
<223> OTHER INFORMATION: Reverse primer for Hsp90, the sequence is
      synthesized

<400> SEQUENCE: 50
tcactccttc cttggcaaca t                                                21
```